US012595479B2

(12) United States Patent
Park et al.

(10) Patent No.: US 12,595,479 B2
(45) Date of Patent: Apr. 7, 2026

(54) ANTISENSE OLIGONUCLEOTIDE-BASED PROGRANULIN AUGMENTATION THERAPY IN NEURODEGENERATIVE DISEASES

(71) Applicants:PRESIDENT AND FELLOWS OF HARVARD COLLEGE, Cambridge, MA (US); THE CHILDREN'S MEDICAL CENTER CORPORATION, Cambridge, MA (US)

(72) Inventors: Peter Jungsoo Park, Cambridge, MA (US); Jin Kuk Kim, Cambridge, MA (US); Timothy Yu, Cambridge, MA (US); Yu-Han Huang, Cambridge, MA (US)

(73) Assignees: PRESIDENT AND FELLOWS OF HARVARD COLLEGE, Cambridge, MA (US); THE CHILDREN'S MEDICAL CENTER CORPORATION, Cambridge, MA (US)

( * ) Notice: Subject to any disclaimer, the term of this patent is extended or adjusted under 35 U.S.C. 154(b) by 1238 days.

(21) Appl. No.: 17/440,438

(22) PCT Filed: Mar. 19, 2020

(86) PCT No.: PCT/US2020/023663
§ 371 (c)(1),
(2) Date: Sep. 17, 2021

(87) PCT Pub. No.: WO2020/191212
PCT Pub. Date: Sep. 24, 2020

(65) Prior Publication Data
US 2022/0154182 A1    May 19, 2022

Related U.S. Application Data

(60) Provisional application No. 62/838,156, filed on Apr. 24, 2019, provisional application No. 62/821,237, filed on Mar. 20, 2019.

(51) Int. Cl.
| | | |
|---|---|---|
| *C07H 21/02* | (2006.01) | |
| *C12N 15/113* | (2010.01) | |
| *C12Q 1/6809* | (2018.01) | |
| *C12Q 1/6811* | (2018.01) | |
| *C12Q 1/6876* | (2018.01) | |
| *G01N 33/50* | (2006.01) | |

(52) U.S. Cl.
CPC .......... *C12N 15/113* (2013.01); *C12Q 1/6809* (2013.01); *C12Q 1/6811* (2013.01); *C12Q 1/6876* (2013.01); *G01N 33/5023* (2013.01); *C12N 2310/11* (2013.01); *C12N 2310/311* (2013.01); *C12N 2310/315* (2013.01); *C12N 2310/3181* (2013.01); *C12N 2310/321* (2013.01); *C12N 2310/322* (2013.01); *C12N 2310/3231* (2013.01); *C12N 2310/3233* (2013.01); *C12N 2310/334* (2013.01); *C12N 2310/3341* (2013.01); *C12N 2310/3525* (2013.01); *C12N 2320/33* (2013.01); *C12Q 2600/158* (2013.01)

(58) Field of Classification Search
CPC .......................... C12N 15/113; C12N 2310/11
See application file for complete search history.

(56) References Cited

U.S. PATENT DOCUMENTS

| | | | |
|---|---|---|---|
| 5,627,274 A | 5/1997 | Kole et al. | |
| 6,172,216 B1 | 1/2001 | Bennett et al. | |
| 6,210,892 B1 | 4/2001 | Bennett et al. | |
| 6,214,986 B1 | 4/2001 | Bennett et al. | |
| 7,250,496 B2 | 7/2007 | Bentwich | |
| 7,838,657 B2 | 11/2010 | Singh et al. | |
| 8,110,560 B2 | 2/2012 | Singh et al. | |
| 8,361,977 B2 | 1/2013 | Baker et al. | |
| 8,980,853 B2 | 3/2015 | Bennett et al. | |
| 9,976,143 B2 | 5/2018 | Krainer et al. | |
| 10,822,369 B2 | 11/2020 | Crooke et al. | |
| 11,739,325 B2 * | 8/2023 | Vargeese .............. | C12N 15/113 536/23.1 |
| 2016/0319286 A1 | 11/2016 | Youn et al. | |
| 2018/0009837 A1 | 1/2018 | Crooke et al. | |
| 2018/0305689 A1 * | 10/2018 | Sætrom ................ | C12N 15/113 |

FOREIGN PATENT DOCUMENTS

| | | | |
|---|---|---|---|
| EP | 1910395 B1 | 10/2012 | |
| WO | 1994/26887 A1 | 11/1994 | |
| WO | 2010/022175 A1 | 2/2010 | |
| WO | 2012/045451 A1 | 4/2012 | |
| WO | 2017/106382 A1 | 6/2017 | |
| WO | 2019/084050 A1 | 5/2019 | |
| WO | 2019/157531 A1 | 8/2019 | |

OTHER PUBLICATIONS

Nedorezova et al. (Theranostics, 2022, 12, 16, 7132-7157).*
Cooper et al. (Annals of Clinical and Translational Neurology 2018; 5(5): 616-629).*
Alberici et al. "Results from a pilot study on amiodarone administration in monogenic frontotemporal dementia with granulin mutation." Neurological Sciences 35(8): 1215-1219 (2014).
Amado et al. "AAV-mediated progranulin delivery to a mouse model of progranulin deficiency causes T cell-mediated toxicity." Molecular Therapy 27(2): 465-478 (2019).

(Continued)

*Primary Examiner* — Amy Rose Hudson
(74) *Attorney, Agent, or Firm* — Nixon Peabody LLP; David S. Resnick; Mark J. FitzGerald

(57) ABSTRACT

Described herein are methods and compositions related to the modulation of progranulin expression or activity in the brain for the treatment of neurodegenerative diseases.

11 Claims, 35 Drawing Sheets

Specification includes a Sequence Listing.

(56) References Cited

OTHER PUBLICATIONS

Arrant et al. "Progranulin gene therapy improves lysosomal dysfunction and microglial pathology associated with frontotemporal dementia and neuronal ceroid lipofuscinosis." Journal of Neuroscience 38(9): 2341-2358 (2018).

Arrant et al. "Restoring neuronal progranulin reverses deficits in a mouse model of frontotemporal dementia." Brain 140(5): 1447-1465 (2017).

Benussi et al. "Loss of neuroprotective factors in neurodegenerative dementias: the end or the starting point?" Frontiers in neuroscience (11): 1-8 (2017).

Capell et al. "Progranulin transcripts with short and long 5' untranslated regions (UTRs) are differentially expressed via posttranscriptional and translational repression." Journal of Biological Chemistry 289(37): 25879-25889 (2014).

Cartegni et al. "Listening to silence and understanding nonsense: exonic mutations that affect splicing." Nature reviews genetics 3(4): 285-298 (2002).

Chen et al. "Association of progranulin polymorphism rs5848 with neurodegenerative diseases: a meta-analysis." Journal of neurology 262(4): 814-822 (2015).

Culler et al. "Functional selection and systematic analysis of intronic splicing elements identify active sequence motifs and associated splicing factors." Nucleic acids research 38(15): 5152-5165 (2010).

Evrony et al. "Cell lineage analysis in human brain using endogenous retroelements." Neuron 85(1): 49-59 (2015).

Fairbrother et al. "Rescue-ESE identifies candidate exonic splicing enhancers in vertebrate exons." Nucleic acids research 32 (Suppl 2): W187-W190 (2004).

Finkel et al. "Treatment of infantile-onset spinal muscular atrophy with nusinersen: a phase 2, open-label, dose-escalation study." The Lancet 388(10063): 3017-3026 (2016).

Finkel et al. "Nusinersen versus sham control in infantile-onset spinal muscular atrophy." New England Journal Medical 377(18): 1723-1732 (2017).

Grindberg et al. "RNA-sequencing from single nuclei." Proceedings of the National Academy of Sciences 110(49): 19802-19807 (2013).

Hovhannisyan et al. "A novel intronic cis element, ISE/ISS-3, regulates rat fibroblast growth factor receptor 2 splicing through activation of an upstream exon and repression of a downstream exon containing a noncanonical branch point sequence." Molecular and Cellular Biology 25(1): 250-263 (2005).

Hua et al. "Enhancement of SMN2 exon 7 inclusion by antisense oligonucleotides targeting the exon." PLoS biology 5(4): 729-744 (2007).

Kao et al. "Progranulin, lysosomal regulation and neurodegenerative disease." Nature Reviews Neuroscience 18(6): 325-333 (2017).

Khvorova et al. "The chemical evolution of oligonucleotide therapies of clinical utility." Nature biotechnology 35(3): 238-248 (2017).

Kim et al. "Patient-customized oligonucleotide therapy for a rare genetic disease." New England Journal of Medicine 381(17): 1644-1652 (2019).

Kordasiewicz et al. "Sustained therapeutic reversal of Huntington's disease by transient repression of huntingtin synthesis." Neuron 74(6): 1031-1044 (2012).

Krawczak et al., "The mutational spectrum of single base-pair substitutions in mRNA splice junctions of human genes: causes and consequences," Hum. Genet. 90(1-2): 41-54 (1992).

Liang et al. "Translation efficiency of mRNAs is increased by antisense oligonucleotides targeting upstream open reading frames." Nature biotechnology 34(8): 875-880 (2016).

Lodato et al. "Aging and neurodegeneration are associated with increased mutations in single human neurons." Science 359(6375): 555-559 (2018).

Lodato et al. "Somatic mutation in single human neurons tracks developmental and transcriptional history." Science 350(6256): 94-98 (2015).

Lui et al. "Progranulin deficiency promotes circuit-specific synaptic pruning by microglia via complement activation." Cell 165(4): 921-935 (2016).

Mercuri et al. "Nusinersen versus sham control in later-onset spinal muscular atrophy." New England Journal of Medicine 378(7): 625-635 (2018).

Minami et al. "Progranulin protects against amyloid B deposition and toxicity in Alzheimer's disease mouse models." Nature medicine 20(10): 1157-1164 (2014).

Minovitsky et al. "The splicing regulatory element, UGCAUG, is phylogenetically and spatially conserved in introns that flank tissue-specific alternative exons." Nucleic acids research 33(2): 714-724 (2005).

Nguyen et al. "Murine knockin model for progranulin-deficient frontotemporal dementia with nonsense-mediated mRNA decay." Proceedings of the National Academy of Sciences 115(12): E2849-E2858 (2018).

Rosenberg et al. "Learning the sequence determinants of alternative splicing from millions of random sequences." Cell 163(3): 698-711 (2015).

Scamborova et al. "An intronic enhancer regulates splicing of the twintron of *Drosophila melanogaster* prospero pre-mRNA by two different spliceosomes." Molecular and cellular biology 24(5): 1855-1869 (2004).

Sha et al. "An 8-week, open-label, dose-finding study of nimodipine for the treatment of progranulin insufficiency from GRN gene mutations." Alzheimer's & Dementia: Translational Research & Clinical Interventions 3(4): 507-512 (2017).

Taylor et al. "Induction of endogenous Bcl-xS through the control of Bcl-x pre-mRNA splicing by antisense oligonucleotides." Nature biotechnology 17(11): 1097-1100 (1999).

Turner et al. "Genetic screening in sporadic ALS and FTD." Journal of Neurology, Neurosurgery & Psychiatry 88(12): 1042-1044 (2017).

Van Kampen et al. "Progranulin gene delivery protects dopaminergic neurons in a mouse model of Parkinson's disease." PLoS one 9(5): 1-10 (2014).

Van Roon-Mom et al. "Dose-dependent lowering of mutant Huntingtin using antisense oligonucleotides in Huntington disease patients." Nucleic acid therapeutics 28(2): 59-62 (2018).

Wang et al. "Systematic identification and analysis of exonic splicing silencers." Cell 119(6): 831-845 (2004).

Ward et al. "Individuals with progranulin haploinsufficiency exhibit features of neuronal ceroid lipofuscinosis." Science translational medicine 9(385): 1-23 (2017).

Wilke et al. "Cerebrospinal fluid progranulin, but not serum progranulin, is reduced in GRN-negative frontotemporal dementia." Neurodegenerative Diseases 17(2-3): 83-88 (2017).

Wilton et al. "Specific removal of the nonsense mutation from the mdx dystrophin mRNA using antisense oligonucleotides." Neuromuscular disorders 9(5): 330-338 (1999).

Wyss-Coray. "Ageing, neurodegeneration and brain rejuvenation." Nature 539(7628): 180-186 (2016).

Yeo et al. "Variation in sequence and organization of splicing regulatory elements in vertebrate genes." Proceedings of the National Academy of Sciences 101(44): 15700-15705 (2004).

* cited by examiner

BodyMap and GEO datasets

WBC_MC
Thyroid
Testis_M
Prostate
PREC_NPC_f
PREC_NPC_cont
PREC_MSCab
PREC_HFDPC
PlacentaEpic_M
Placenta
Ovary
Muscle
Muscle_c
Melanocytes
Lymphode
Lung
Liver_M
Kidney_M
iPSd
iPSac
Heart_M
GLS_cells_M
Fibr_M
EpithelialCells
Endothelium
EndomStromalc_M
Decidua
Colon
Chorion
Amnion
Adrenal
Adipose_Breast Other

*FIG. 1B (cont.)*

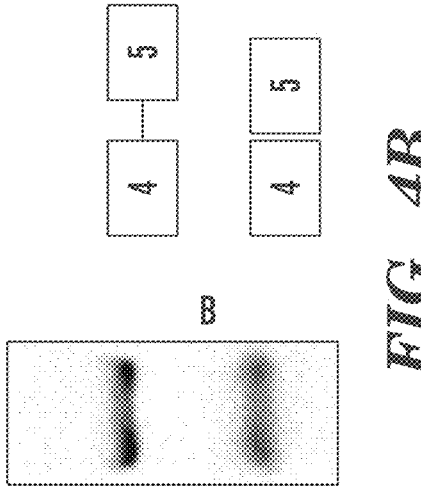
*FIG. 4B*
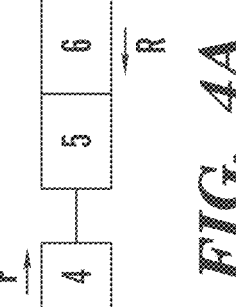
*FIG. 4A*
Forward (F) primer:  5'– GCGATCCTGCTTCCAAAGAT
Reverse (R) primer:  5'– GTGAACCAGGTCGCAGAAG
*FIG. 4C*

GAPDH

Forward (F) primer: 5'– TGCTTCCAAAGATCAGGTAACA

Reverse (R) primer: 5'– GCCACTGCCCTGTTAGTC

Fwd primer: 5' - GCCCTGATCCCTGGCCAATG

Rev primer: 5' - TGGGCCATTTGTCCAGAAG

5'UTR-extended (non-productive) *GRN* transcript level

Relative level

Suppression of non-productive isoform

Controls

Screened ASOs

Ctrl SPIN S01 S02 S03 S04 S05 S06 S07 S08 S09 S10 S11 S12 S13 S14 S15

Transfection (48h, 200nM), qRT-PCR (N=4)

Dose-dependent progranulin protein
upregulation by S37 (top lead ASO)

Increased progranulin protein
secretion by S37 (top lead ASO)

| Group | Dose (mg/dose; human equivalent) | Day 29 necropsy (2 wks after 2nd dose) | Day 57 necropsy (2 wks after 4th dose) | Day 113 necropsy (10 wks after 4th dose) |
|---|---|---|---|---|
| 1 Control | 0, 0, 0, 0 | 1 | 1 | 1 |
| 2 Test article 1 (S37) | 40, 120, 360, 1080 | 1 | 1 | 1 |
| 3 Test article 2 (S10) | 40, 120, 360, 1080 | 1 | 1 | 1 |
| 4 Test article 3 (S7) | 40, 120, 360, 1080 | 1 | 1 | 1 |

Dosing schedule: w0, w2, w4, w6

SEQUENCE LISTING

<160> NUMBER OF SEQ ID NOS: 48

<210> SEQ ID NO 1
<211> LENGTH: 8021
<212> TYPE: DNA
<213> ORGANISM: Homo sapiens

<400> SEQUENCE: 1

```
attctccaat cacatgatcc ctagaaatgg ggtgtggggc gagaggaagc agggaggaga        60
gtgatttgag tagaaaagaa acacagcatt ccaggctggc cccacctcta tattgataag       120
tagccaatgg gagcgggtag ccctgatccc tggccaatgg aaactgaggt aggcgggtca       180
tcgcgctggg gtctgtagtc tgagcgctac ccggttgctg ctgcccaagg accgcggagt       240
cggacgcagg taggagagcg gccgcgcaga cctctcgcct gctcctgccc aggggcccgc       300
cagggccatg tgagcttgag gttcccctgg agtctcagcc ggagacaaca gaagaaccgc       360
ttactgaaac tccttggggg ttctgataca ctaggggag ttttatggga aagaggaagc        420
agtaattgca gtgacgcccc gttagaaggg gctttctacc tccccagcat tcccccaaag       480
cagggaccac accattcttg acccagctcc accctgtcg gtaggtgctg gcttcttccc        540
ctctcctggt ggtggtgggt ggttcccgcg gcggcctgga gccggagggg cgcgcgaccc       600
tgggctggga gctccgaggg cctgggaacg agacctgaga ccttggcttc tcgaaggtag       660
tagggacttg ggagtggtga ctgaacctgg tctggctcct ccttacttcc tcttgttgcg       720
ggtgggacga gctagcttcc gcctctccca gccacttttt cctgctcatt tgcagctagg       780
ttggctcccc ttttgggaat ttcctctccc cttggcactc ggagttgggg ggtgccacct       840
agtggaagat aacggagcta gggtcttgaa gaggctgctg tcccctctgg ctgttttggc       900
ggtgtagggt ggcatgagag actgcgactc gcctcctcat ccctgtttct gtatgcgagt       960
gcttgtattc agtagaagca tacactatac tccctcaatt tagggtaaac aggaggggcc      1020
acatgcacag gtaattcacc agggagccga acactcctgt gcagacagac tccccttccc      1080
agcaagccat ggcagcggac agcctgctga gaacacccag gaagcaggcg gtgccagctg      1140
caggtgcttt gcctgggagc tgtggggctg aggagagggt ccactgtcca ggaccagtga      1200
```

-continued

```
acttcatcct tatctgtcca ggaggtggcc tcttggggat gctgagttag gggaggggca      1260
cttgaggaaa gccaggtgga gcagagagga tgtgagtgac tgggtgggtg agatttcctg      1320
cccctccccc cgcagtggta tccacaccta gactcgtggg gtaactgagg cacagacaga      1380
gagcaacttc tcaggccctc acagttggca attctaggat taggacccaa gtgcgatttt      1440
caggcagtcc ctgtaccctg tttctgttgt acctgttgca ccattcccag gcactgccca      1500
tcgtgccact agtgatatga acccaggtcc aatacgctct ggggccatca aagcctgacg      1560
tcaccatgac ctgatgtgtg acgtgttata ggtgtccctt ggtatcttca cggaactggt      1620
tccaggaccc caaaatctgt gggtgctcaa gcccctgaga taaaatggtg taatatttgc      1680
atataaccta tacatacttt aaatcatttc tagattactt atacctaata caatggaaat      1740
gacatgtcgg ctgggcgtgg tggctcatgc ctgtaatccc accactttgg gaggccgtgg      1800
caggtggatc acctgaggtc tggagtttga gaccagcctg accaacatgg tgaaaccccc      1860
atctctacta aaaatacaaa aattagccag gtgtggtagc gcacacctat aatcccacct      1920
acttgggagg ctgaggcagg agaattgctt gaacctggga ggcggagttc gcagtaagct      1980
gagatcgcgc cactgtacta cagcctgggt gacagagcag gactccatct caaaaaaaaa      2040
agagaaaaag aaaaagaaat gccatgtaaa tagttgtgat cctgaattgt ttagggaata      2100
ataagaaaga actatctgta gatgttcagt atagatgcac ccatcgtaag cctaactaca      2160
ttgtataact cagcaacgat gtaacatttt caggggtttt tttgttttgt tttttgagac      2220
agaatctcag tctcactctg tcacccaggc tggagtatgt tggcgtgatc tctgctcact      2280
gcaacctcca cctcctgggc tcaagcgatt ctcctgcctc agcctcttga gtagctggga      2340
ttgcaggtgt gcgctaccac gcatggctaa ttttttgtatt tttaatagag atggggtttt      2400
accacgttgg tcaggctggt cttgaactcc tgaccttggg atccgcccac ctgggcctcc      2460
caaagtgctg ggattacagg cgttagccac cgcgcccaat atattttgat ccctggttgg      2520
atatggaggc ctgactgtac ttaacatctc taagcttcag tttcctcctt taaaataaag      2580
gtgtggctgg gtgtggtggt tcaagcctgt aatcccagca cttaggaggg ctgaggtggg      2640
tggatcagct gaggtcagga gttcaagacc agcctgacca atatggtgaa accccctctc      2700
tgctaaaaat acaaaaatta gccaggcgtg gtggcgagcg cctgtagtcc cagctacttg      2760
cttgaacttg ggaggcagag gttgcagtga gctgagatcg tgccactgaa ctcgagcatg      2820
ggcaacagag caagactgtc tcaaaaaaaa aaaaaaaaag ggggtgagca gacgtggtgg      2880
cacgctccca cagtcccagc tacttagtag gaggccaagg ttggaggatt gcttgatccc      2940
aggagtctga gtccagcctg ggcaacatgg caatacctca tctctaaaaa taaaataaaa      3000
gtaaaggtat taattactac tttggatggt tgttgcaaag aaatatatat aaaataatgg      3060
agagtcttgt aactggctcc caagaggctc aacagacatt actgtttttg cttcttcatt      3120
atgagttacc tctctggcca ccccactgaa ctagctgggc tagctgagcc tgggagaaga      3180
gttgtttagg aagtgagagg ctgctctcca cagagactca aggctcagtt cctcctggtg      3240
actcagatgg gcagcccagt gggcacacgt ggtctctctc cacatgtggc tgagtttcac      3300
ttccagaata gatggagagg caagggcagg gtttagcatg cttgaggaat ctcagagggc      3360
cctggtggtg tgggggaccc tcagaacaca ggtgtctcaa gggctgaccc agcttctgtg      3420
tccttttctc tgggtgagga ggggacattc atgggcagat ggtgacctct ggggaaggca      3480
gcccagactc cactggccac catatttcct ttttcacaac tttctcaccc ctgtggtttc      3540
ccatgtcatc atgtggccgc ttcccgcaag gccttagcgg ggtgcaggta tgaacatagt      3600
```

-continued

```
gtcaggcaag gaggcatctg gaggggaacc ctggcttttc ctggggggac tccctccctg   3660
caccctagcc ctgtcctctc ccatggctac tgatgccttc ccctcacccc agaggtggcc   3720
cacatctgca cagatcagac ccacaaaaat cacgtcttcc tgactctcat aagcctgccc   3780
agtgaggccc aggcattagg ccatgtgctg gggactcaga cccacacata tacgcatgtc   3840
agcattcatg cttacaggtc cgcacatgct ggggcaagtg tcacacacgg ggcgctgtag   3900
gaagctgact ctcagcccct gcagatttct gcctgcctgg acagggaggt gttgagaagg   3960
ctcaggcagt cctgggccag gaccttggcc tggggctagg gtactgagtg accctagaat   4020
caagggtggc gtgggcttaa gcagttgcca gacgttcctt ggtactttgc aggcagacca   4080
tgtggaccct ggtgagctgg gtggccttaa cagcagggct ggtggctgga acgcggtgcc   4140
cagatggtca gttctgccct gtggcctgct gcctggaccc cggaggagcc agctacagct   4200
gctgccgtcc ccttctggtg agtgcccctc agcctaggca agagctggca gcctgggttt   4260
tcccaaaggg tcatcttgga ttggccagag gaggacgcca ggcacaagtc tgtggtttat   4320
cattttccct gtctttctag gacaaatggc ccacaacact gagcaggcat ctgggtggcc   4380
cctgccaggt tgatgcccac tgctctgccg gccactcctg catctttacc gtctcaggga   4440
cttccagttg ctgccccttc ccagaggtga gcgtgccatc agcccagtgg aggggcttag   4500
gtctgcattt atgcttttcc tgcactctac cacctgcaga taaaagggcc ctgccaatgc   4560
aggtttctct gtgttccaca ggccgtggca tgcggggatg gccatcactg ctgcccacgg   4620
ggcttccact gcagtgcaga cgggcgatcc tgcttccaaa gatcaggtgc agctggggtg   4680
tgggtgcagg gcaggcagac gggcagcatg tggagtctgg aacccaggag cccagctggc   4740 ggggcagcc ctgattcctg cccttgtgcc ctcattcatg tggcatctgt actaagcaac   4800
agccctgctg tggacagagg ggcagcactg gggataggag ggtgcgggag aaagtgcaag   4860
actccaggtc caggcgttgt ggggggtgggg agaggtcgag ctgggccggt ctaataccaa   4920
cccatggtca gtgggtgccc cttccccatg ccatcttgct gagggaggga ctggattgtg   4980
aggagggtga gttaggcctg cctaggagat cactgagcct tagtgtcacc ctcaaacccc   5040
agtagctggg cttgcaggcc ctggtgccac cagctccttg tgtgatgggg gagtcacctt   5100
ccctgagtgg gctggtagta tcctgggtca tcttgtccac aggtaacaac tccgtgggtg   5160
ccatccagtg ccctgatagt cagttcgaat gcccggactt ctccacgtgc tgtgttatgg   5220
tcgatggctc ctgggggtgc tgccccatgc cccaggtaca aatctggggg agatgggggt   5280
atgtggaggg aagtgggggc agagttgggg gccaggggca ggggtgaag acggagtcag   5340 gaccattttt tctcaggctt cctgctgtga agacagggtg cactgctgtc cgcacggtgc   5400
cttctgcgac ctggttcaca cccgctgcat cacacccacg ggcacccacc ccctggcaaa   5460
gaagctccct gcccagagga ctaacagggc aggtgaggag gtgggagagc atcaggccag   5520
gggctggggc ggggcctcat tgactccaag tgtaggaaaa agtttcctcc atcctggctg   5580
cccctcacgt ttgctcctct tccagtggcc ttgtccagct cggtcatgtg tccggacgca   5640
cggtcccggt gccctgatgg ttctacctgc tgtgagctgc ccagtgggaa gtatggctgc   5700
tgcccaatgc ccaacgtgag tgaggggctg gagccagctt ggctgtgtgc ccccagccac   5760
ctggccctga cacgcacctt acaggggctc tgtggcatgg ggctggctgg ctgcttgctg   5820
ggagcctggc tgatgcaggg ttcatgctac cccctagtgg gggattgggg cagtgccagc   5880
catcagcctg gctgctccct gtgtgctact gagcctggaa gtgacaaaga cccacccctg   5940
```

```
tccccactca ggccacctgc tgctccgatc acctgcactg ctgcccccaa gacactgtgt    6000
gtgacctgat ccagagtaag tgcctctcca aggagaacgc taccacggac ctcctcacta    6060
agctgcctgc gcacacaggt accagaggca gggtgcagat acaggggtgg ggcccccttt    6120
cctccctttt aggcctggcc ttaggatcac tgcaaggtgg tgtaagcggt accctccatc    6180
ttcaacacct ggttccagct gtggagccgg caaagggttg atacccctga gggtccccag    6240
tgccacttct gacctgtcct ctctgcttcc ctcacagtgg gggatgtgaa atgtgacatg    6300
gaggtgagct gcccagatgg ctatacctgc tgccgtctac agtcgggggc ctggggctgc    6360 tgcccttttta cccaggtacc caggggtggc gggtggtgg gctgagcaca gtgtggcagg    6420
cagccgggcc ccagtgccca cctgcccttc ttcatctgcc ctaggctgtg tgctgtgagg    6480
accacataca ctgctgtccc gcggggttta cgtgtgacac gcagaagggt acctgtgaac    6540
aggggcccca ccaggtgccc tggatggaga aggccccagc tcacctcagc ctgccagacc    6600
cacaagcctt gaagagagat gtccctgtg ataatgtcag cagctgtccc tcctccgata    6660
cctgctgcca actcacgtct ggggagtggg gctgctgtcc aatcccagag gtatatggga    6720
ggggacagca tcttggcctg ggcaggtggg tggccaagct cctattgctt tctgccctcc    6780
gcatagccca taggtgatac ccagctctga cagattcgtc cccagctgga ggtgctgtaa    6840
gcaggagagg cgggctggag taggtagggg ctcggcactg cgccccacat agtggctacc    6900
tacaacgccc tttcctgccc accccccagg ctgtctgctg ctcggaccac cagcactgct    6960
gcccccaggg ctacacgtgt gtagctgagg ggcagtgtca gcgaggaagc gagatcgtgg    7020
ctggactgga gaagatgcct gcccgccggg cttccttatc ccaccccaga gacatcggct    7080
gtgaccagca caccagctgc ccggtggggc agacctgctg cccgagcctg ggtgggagct    7140
gggcctgctg ccagttgccc catgtgagtg cctccctgcc tgcccctgga tagggggagct    7200 aagcccagtg aggggacagg aacataatgc cattctgtgc tcccttcccc gccaggctgt    7260
gtgctgcgag gatcgccagc actgctgccc ggctggctac acctgcaacg tgaaggctcg    7320
atcctgcgag aaggaagtgg tctctgccca gcctgccacc ttcctggccc gtagccctca    7380
cgtgggtgtg aaggacgtgg agtgtgggga aggacacttc tgccatgata accagacctg    7440
ctgccgagac aaccgacagg ctgggcctg ctgtccctac cgccaggtca gtgccaaccc    7500
ccatcctggg gctgggtatg gccagggacc aggtcccacc tcgtccaacc ctctcgcccc    7560
cctctgacca tccagggcgt ctgttgtgct gatcggcgcc actgctgtcc tgctggcttc    7620
cgctgcgcag ccaggggtac caagtgtttg cgcaggagg ccccgcgctg ggacgcccct    7680
ttgagggacc cagccttgag acagctgctg tgagggacag tactgaagac tctgcagccc    7740
tcgggacccc actcggaggg tgccctctgc tcaggcctcc ctagcacctc cccctaacca    7800
aattctccct ggaccccatt ctgagctccc catcaccatg ggaggtgggg cctcaatcta    7860
aggccttccc tgtcagaagg gggttgtggc aaaagccaca ttacaagctg ccatcccctc    7920
cccgtttcag tggaccctgt ggccaggtgc ttttccctat ccacagggt gtttgtgtgt    7980 gtgcgcgtgt gcgtttcaat aaagtttgta cactttctta a    8021
```

<210> SEQ ID NO 2
<211> LENGTH: 2356
<212> TYPE: DNA
<213> ORGANISM: Homo sapiens

<400> SEQUENCE: 2

```
attctccaat cacatgatcc ctagaaatgg ggtgtggggc gagaggaagc agggaggaga      60
```

```
gtgatttgag tagaaaagaa acacagcatt ccaggctggc cccacctcta tattgataag      120
tagccaatgg gagcgggtag ccctgatccc tggccaatgg aaactgaggt aggcgggtca      180
tcgcgctggg gtctgtagtc tgagcgctac ccggttgctg ctgcccaagg accgcggagt      240
cggacgcagg cagaccatgt ggaccctggt gagctgggtg gccttaacag cagggctggt      300
ggctggaacg cggtgcccag atggtcagtt ctgccctgtg gcctgctgcc tggaccccgg      360
aggagccagc tacagctgct gccgtcccct tctggacaaa tggcccacaa cactgagcag      420
gcatctgggt ggccctgcc aggttgatgc ccactgctct gccggccact cctgcatctt       480
taccgtctca gggacttcca gttgctgccc cttcccagag gccgtggcat gcggggatgg      540
ccatcactgc tgcccacggg gcttccactg cagtgcagac gggcgatcct gcttccaaag      600
atcaggtaac aactccgtgg gtgccatcca gtgccctgat agtcagttcg aatgcccgga      660
cttctccacg tgctgtgtta tggtcgatgg ctcctggggg tgctgcccca tgccccaggc      720
ttcctgctgt gaagacaggg tgcactgctg tccgcacggt gccttctgcg acctggttca      780
cacccgctgc atcacaccca cgggcaccca cccctggca aagaagctcc ctgcccagag      840
gactaacagg gcagtggcct tgtccagctc ggtcatgtgt ccggacgcac ggtcccggtg      900
ccctgatggt tctacctgct gtgagctgcc cagtgggaag tatggctgct gcccaatgcc      960
caacgccacc tgctgctccg atcacctgca ctgctgcccc caagacactg tgtgtgacct     1020
gatccagagt aagtgcctct ccaaggagaa cgctaccacg gacctcctca ctaagctgcc     1080
tgcgcacaca gtgggggatg tgaaatgtga catggaggtg agctgcccag atggctatac     1140
ctgctgccgt ctacagtcgg gggcctgggg ctgctgccct tttacccagg ctgtgtgctg     1200
tgaggaccac atacactgct gtcccgcggg gtttacgtgt gacacgcaga agggtacctg     1260
tgaacagggg ccccaccagg tgccctggat ggagaaggcc ccagctcacc tcagcctgcc     1320
agacccacaa gccttgaaga gagatgtccc ctgtgataat gtcagcagct gtccctcctc     1380
cgatacctgc tgccaactca cgtctgggga gtggggctgc tgtccaatcc cagaggctgt     1440
ctgctgctcg gaccaccagc actgctgccc ccagggctac acgtgtgtag ctgaggggca     1500
gtgtcagcga ggaagcgaga tcgtggctgg actggagaag atgcctgccc gccgggcttc     1560
cttatcccac cccagagaca tcggctgtga ccagcacacc agctgcccgg tggggcagac     1620
ctgctgcccg agcctgggtg ggagctgggc ctgctgccag ttgccccatg ctgtgtgctg     1680
cgaggatcgc cagcactgct gcccggctgg ctacacctgc aacgtgaagg ctcgatcctg     1740
cgagaaggaa gtggtctctg cccagcctgc caccttcctg gcccgtagcc ctcacgtggg     1800
tgtgaaggac gtggagtgtg gggaaggaca cttctgccat gataaccaga cctgctgccg     1860
agacaaccga cagggctggg cctgctgtcc ctaccgccag ggcgtctgtt gtgctgatcg     1920
gcgccactgc tgtcctgctg gcttccgctg cgcagccagg ggtaccaagt gtttgcgcag     1980
ggaggccccg cgctgggacg cccctttgag ggacccagcc ttgagacagc tgctgtgagg     2040
gacagtactg aagactctgc agccctcggg accccactcg gagggtgccc tctgctcagg     2100
cctccctagc acctcccect aaccaaattc tccctggacc ccattctgag ctccccatca     2160
ccatgggagg tggggcctca atctaaggcc ttccctgtca gaagggggtt gtggcaaaag     2220
ccacattaca agctgccatc ccctccccgt ttcagtggac cctgtggcca ggtgcttttc     2280
cctatccaca ggggtgtttg tgtgtgtgcg cgtgtgcgtt tcaataaagt ttgtacactt     2340
tcttaaaaaa aaaaaa                                                     2356
```

-continued

```
<210> SEQ ID NO 3
<211> LENGTH: 593
<212> TYPE: PRT
<213> ORGANISM: Homo sapiens

<400> SEQUENCE: 3

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
            35                  40                  45

Trp Pro Thr Thr Leu Ser Arg His Leu Gly Gly Pro Cys Gln Val Asp
        50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
            115                 120                 125

Ser Gln Phe Glu Cys Pro Asp Phe Ser Thr Cys Cys Val Met Val Asp
        130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
            195                 200                 205

Pro Asp Ala Arg Ser Arg Cys Pro Asp Gly Ser Thr Cys Cys Glu Leu
        210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285

Ser Cys Pro Asp Gly Tyr Thr Cys Cys Arg Leu Gln Ser Gly Ala Trp
        290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

Val Ser Ser Cys Pro Ser Ser Asp Thr Cys Cys Gln Leu Thr Ser Gly
        370                 375                 380
```

```
Glu Trp Gly Cys Cys Pro Ile Pro Glu Ala Val Cys Cys Ser Asp His
385                 390             395                 400

Gln His Cys Cys Pro Gln Gly Tyr Thr Cys Val Ala Glu Gly Gln Cys
                405             410                 415

Gln Arg Gly Ser Glu Ile Val Ala Gly Leu Glu Lys Met Pro Ala Arg
            420             425             430

Arg Ala Ser Leu Ser His Pro Arg Asp Ile Gly Cys Asp Gln His Thr
            435             440             445

Ser Cys Pro Val Gly Gln Thr Cys Cys Pro Ser Leu Gly Gly Ser Trp
        450             455             460

Ala Cys Cys Gln Leu Pro His Ala Val Cys Cys Glu Asp Arg Gln His
465                 470             475                 480

Cys Cys Pro Ala Gly Tyr Thr Cys Asn Val Lys Ala Arg Ser Cys Glu
                485             490             495

Lys Glu Val Val Ser Ala Gln Pro Ala Thr Phe Leu Ala Arg Ser Pro
            500             505             510

His Val Gly Val Lys Asp Val Glu Cys Gly Glu Gly His Phe Cys His
            515             520             525

Asp Asn Gln Thr Cys Cys Arg Asp Asn Arg Gln Gly Trp Ala Cys Cys
        530             535             540

Pro Tyr Arg Gln Gly Val Cys Cys Ala Asp Arg Arg His Cys Cys Pro
545                 550             555                 560

Ala Gly Phe Arg Cys Ala Ala Arg Gly Thr Lys Cys Leu Arg Arg Glu
                565             570             575

Ala Pro Arg Trp Asp Ala Pro Leu Arg Asp Pro Ala Leu Arg Gln Leu
            580             585             590

Leu
```

```
<210> SEQ ID NO 4
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gcaugagcgg gcccugaa                                                          18

<210> SEQ ID NO 5
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gcgagagguc ugcgcggccg                                                        20

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
```
agcaggcgag aggucugcgc                                                        20

<210> SEQ ID NO 7
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gcaggagcag gcgagagguc                                                        20

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
cuccggcuga gacuccaggg                                                        20

<210> SEQ ID NO 9
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gucuccggcu gagacuccag                                                        20

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ucuucuguug ucuccggcug                                                        20

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
guaagcgguu cuucguugu                                                         20

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
aguuucagua agcgguucuu                                                        20

```
<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cgacaggggu ggagcugggu                                              20

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
cuaccgacag ggguggagcu                                              20

<210> SEQ ID NO 15
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gcaccuaccg acaggggugg                                              20

<210> SEQ ID NO 16
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gccagcaccu accgacaggg                                              20

<210> SEQ ID NO 17
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
agaagccagc accuaccgac                                              20

<210> SEQ ID NO 18
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gggaagaagc cagcaccuac                                              20
```

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gccctgatcc ctggccaatg                                              20

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgggccattt gtccagaag                                               19

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcggacgcag gtaggag                                                 17

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cacatggtct gccgacag                                                18

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
ctgggtcaag aatggtgtgg tccctg                                       26

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtcggacgca ggcaga                                                  16

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgggccattt gtccagaag                                                      19

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
ttaacagcag ggctggtggc tggaac                                              26

<210> SEQ ID NO 27
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ccugcaccca cacccca                                                        17

<210> SEQ ID NO 28
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ccugcccugc acccaca                                                        17

<210> SEQ ID NO 29
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gucugccugc ccugcac                                                        17

<210> SEQ ID NO 30
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ugcccgucug ccugccc                                                        17

<210> SEQ ID NO 31

```
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
acaugcugcc cgucugcc                                                     18

<210> SEQ ID NO 32
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
acuccacaug cugcccgu                                                     18

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uuccagacuc cacaugcug                                                    19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
cuggguucca gacuccaca                                                    19

<210> SEQ ID NO 35
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
gcuccugggu uccagacu                                                     18

<210> SEQ ID NO 36
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
cugggcuccu ggguucc                                                      17

<210> SEQ ID NO 37
<211> LENGTH: 17
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
gccagcuggg cuccugg                                                        17

<210> SEQ ID NO 38
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ccccgccagc ugggcu                                                         16

<210> SEQ ID NO 39
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
gcugcccccg ccagcu                                                         16

<210> SEQ ID NO 40
<211> LENGTH: 3944
<212> TYPE: DNA
<213> ORGANISM: Homo sapiens
<220> FEATURE:
<221> NAME/KEY: modified_base
<222> LOCATION: (1242)..(1242)
<223> OTHER INFORMATION: a, c, t, g, unknown or other
<220> FEATURE:
<221> NAME/KEY: modified_base
<222> LOCATION: (1247)..(1247)
<223> OTHER INFORMATION: a, c, t, g, unknown or other
<220> FEATURE:
<221> NAME/KEY: modified_base
<222> LOCATION: (1264)..(1267)
<223> OTHER INFORMATION: a, c, t, g, unknown or other
<220> FEATURE:
<221> NAME/KEY: modified_base
<222> LOCATION: (1279)..(1279)
<223> OTHER INFORMATION: a, c, t, g, unknown or other
<220> FEATURE:
<221> NAME/KEY: modified_base
<222> LOCATION: (1460)..(1463)
<223> OTHER INFORMATION: a, c, t, g, unknown or other
<220> FEATURE:
<221> NAME/KEY: modified_base
<222> LOCATION: (1676)..(1677)
<223> OTHER INFORMATION: a, c, t, g, unknown or other
<220> FEATURE:
<221> NAME/KEY: modified_base
<222> LOCATION: (1689)..(1689)
<223> OTHER INFORMATION: a, c, t, g, unknown or other
<220> FEATURE:
<221> NAME/KEY: modified_base
<222> LOCATION: (1706)..(1706)
<223> OTHER INFORMATION: a, c, t, g, unknown or other
<220> FEATURE:
<221> NAME/KEY: modified_base
<222> LOCATION: (1748)..(1748)
<223> OTHER INFORMATION: a, c, t, g, unknown or other
<220> FEATURE:
<221> NAME/KEY: modified_base
```

-continued

```
<222> LOCATION: (2034)..(2034)
<223> OTHER INFORMATION: a, c, t, g, unknown or other
<220> FEATURE:
<221> NAME/KEY: modified_base
<222> LOCATION: (2150)..(2153)
<223> OTHER INFORMATION: a, c, t, g, unknown or other
<220> FEATURE:
<221> NAME/KEY: modified_base
<222> LOCATION: (2162)..(2162)
<223> OTHER INFORMATION: a, c, t, g, unknown or other
<220> FEATURE:
<221> NAME/KEY: modified_base
<222> LOCATION: (2164)..(2164)
<223> OTHER INFORMATION: a, c, t, g, unknown or other
<220> FEATURE:
<221> NAME/KEY: modified_base
<222> LOCATION: (2728)..(2728)
<223> OTHER INFORMATION: a, c, t, g, unknown or other
<220> FEATURE:
<221> NAME/KEY: modified_base
<222> LOCATION: (2748)..(2748)
<223> OTHER INFORMATION: a, c, t, g, unknown or other
<220> FEATURE:
<221> NAME/KEY: modified_base
<222> LOCATION: (2755)..(2755)
<223> OTHER INFORMATION: a, c, t, g, unknown or other
<220> FEATURE:
<221> NAME/KEY: modified_base
<222> LOCATION: (2768)..(2768)
<223> OTHER INFORMATION: a, c, t, g, unknown or other
<220> FEATURE:
<221> NAME/KEY: modified_base
<222> LOCATION: (2787)..(2787)
<223> OTHER INFORMATION: a, c, t, g, unknown or other
<220> FEATURE:
<221> NAME/KEY: modified_base
<222> LOCATION: (2794)..(2794)
<223> OTHER INFORMATION: a, c, t, g, unknown or other
<220> FEATURE:
<221> NAME/KEY: modified_base
<222> LOCATION: (3141)..(3141)
<223> OTHER INFORMATION: a, c, t, g, unknown or other
<220> FEATURE:
<221> NAME/KEY: modified_base
<222> LOCATION: (3426)..(3426)
<223> OTHER INFORMATION: a, c, t, g, unknown or other
<220> FEATURE:
<221> NAME/KEY: modified_base
<222> LOCATION: (3437)..(3437)
<223> OTHER INFORMATION: a, c, t, g, unknown or other
<220> FEATURE:
<221> NAME/KEY: modified_base
<222> LOCATION: (3460)..(3460)
<223> OTHER INFORMATION: a, c, t, g, unknown or other
<220> FEATURE:
<221> NAME/KEY: modified_base
<222> LOCATION: (3465)..(3465)
<223> OTHER INFORMATION: a, c, t, g, unknown or other
<220> FEATURE:
<221> NAME/KEY: modified_base
<222> LOCATION: (3481)..(3484)
<223> OTHER INFORMATION: a, c, t, g, unknown or other

<400> SEQUENCE: 40
gcagaccatg tggaccctgg tgagctgggt ggccttaaca gcagggctgg tggctggaac      60
gcggtgccca gatggtcagt tctgccctgt ggcctgctgc ctggaccccg gaggagccag     120
ctacagctgc tgccgtcccc ttctggtgag tgccctcagc ctaggcaaga gctggcagct     180
gggtttttcc aaagggtcat cttggattgg ccagaggagg acgccaggca caagtctgtg     240
gtttatcatt ttccctgtct ttctaggaca aatggcccac aacactgagc aggcatctgg     300
gtggcccctg ccaggttgat gcccactgct ctgccggcca ctcctgcatc tttaccgtct     360
cagggacttc cagttgctgc cccttcccag aggtgagcgt gccatcagcc caatggaggg     420
```

-continued

```
gcttaggtct gcatttatgc ttttcctgca ctctaccacc tgcagataaa agggccctgc      480
caatgcaggt ttctctgtgt tccacaggcc gtggcatgcg gggatggcca tcactgctgc      540
ccacggggct tccactgcag tgcagacggg cgatcctgct tccaaagatc aggtgcagct      600
ggggtgtggg tgcagggcag gcagacgggc agcatgtgga gtctggaacc caggagccca      660
gctggcgggg gcagccctga ttcctgccct tgtgccctca ttcatgtggc atctgtacta      720
agcaacagcc ctgctgtgga cagaggggca gcactgggga taggagggtg cgggagaaag      780
tgcaagactc caggtccagg cgttgtgggg gtggggagag gtcgagctgg gccggtctaa      840
taccaaccca tggtcagtgg gtgcccctttt ccccatgcca tcttgctgag ggagggactg      900
gattgtgagg agggtgagtt aggcctccta ggagatcact gagccttagt gtcaccctca      960
aaccccagta gctgggcttg caggcctggt gccaccagct ccttgtgtga tgggggagtc     1020
agtcaccttc cctgagtggg ctggtagtat cctgggtcat cttgtccaca ggtaacaact     1080
ccgtgggtgc catccagtgc cctgatagtc agttcgaatg cccggacttc tccacgtgct     1140
gtgttatggt cgatggctcc tgggggtgct gccccatgcc ccaggtacaa atctggggga     1200 gatgggggata tgtggaggga agtgggggca gagttggggg cnaggcnagg gggtgaagac     1260
ggannnngga ccattttttnc tcaggcttcc tgctgtgaag acagggtgca ctgctgttcc     1320
gcacggtgcc ttctgcgacc tggttcacac ccgctgcatc acacccacgg gcacccaccc     1380
cctggcaaag aagctccctg cccagaggac taacagggca ggtgaggagg tgggagagca     1440
tcaggccagg ggctggggcn nnnctcattg actccaagtg taggaaaaag tttcctccat     1500
cctggctgcc cctcacgttt gctcctcttc cagtggcctt gtccagctcg gtcatgtgtc     1560
cggacgcacg gtcccggtgc cctgatggtt ctacctgctg tgagctgcca gtggaagtat     1620
ggctgctgcc caatgcccaa cgtgagtgag ggctgaacca gcttggctgt gtgccnncag     1680
ccacctganc ctgacacgca ccttanaggg gctctgtggc atggggctgg ctggctgctt     1740
gctgggancc tggctgatgc agggttcatg ctaccccta gtgggggatt ggggcagtgc     1800
cagccatcag cctggctgct ccctgtgtgc tactgagcct ggaagtgaca aagacccacc     1860
cctgtcccca ctcaggccac ctgctgctcc gatcacctgc actgctgccc ccaagacact     1920
gtgtgacctg atccagagta agtgcctctc caaggagaac gctaccacgg acctcctcac     1980
taagctgcct gcgcacacag gtaccagagg caggtgcag atacaggggt gggncccccct     2040 ttcctccctt ttaggcctgg ccttaggatc actgcaaggt ggtgtaagcg gtaccctcca     2100
tcttcaacac ctggttccag ctgtggagcc ggcaaagggt tgatgccccn nnnggtcccc     2160
antnccactt ctgacctgtc ctctctgctt ccctcacagt gggggatgtg aaatgtgaca     2220
tggaggtgag ctgcccagat ggctatacct gctgccgtct acagtcgggg gcctggggct     2280
gctgcccttt tacccaggta ccaggtgcgg cggtggctga gcacagtgtg cagcagccgg     2340
ccccagtgcc cacctgccct tcttcatctg ccctaggctg tgtgctgtga ggaccacata     2400
cactgctgtc ccgcgggggtt tacgtgtgac acgcagaagg gtacctgtga acaggggccc     2460
caccaggtgc cctggtggag aaggccccag ctcacctcag cctgccagac ccacaagcct     2520
tgaagagaga tgtcccctgt gataatgtca gcagctgtcc ctcctccgat acctgctgcc     2580
aactcacgtc tggggagtgg ggctgctgtc caatcccaga ggtatatggg aggggacagc     2640
atcttggcct gggcaggtgg gtggccaagc tcctattgct ttctgccctc cgcatagccc     2700
ataggtgata cccagctctg acagattngt ccccagctgg aggtgctnta agagngagag     2760
gcgggctnga gtaggtaggg gctcggnact tcgncccaca tagtggctac ctacaacgcc     2820
```

```
ctttcctgcc cacccccag gctgtctgct gctcggacca ccagcactgc tgcccccagg      2880
gctacacgtg tgtagctgag gggcagtgtc agcgaggaag cgagatcgtg gctggactgg      2940
agaagatgcc tgcccgccgg gcttccttat cccacccccag agacatcggc tgtgaccagc     3000
acaccagctg cccggtgggg cagacctgct gcccgagcct gggtgggagc tgggcctgct     3060
gccagttgcc ccatgtgagt gcctccctgc ctgcccctgg ataggggagc taagcccagt     3120
gagggagcta agcccagtga nggacaggaa cataatgcca ttctgtgctc ccttcccgcc     3180
aggctgtgtg ctgcgaggat cgccagcact gctgcccggc tggctacacc tgcaacgtga     3240
aggctcgatc ctgcgagaag gaagtggtct ctgcccagcc tgccaccttc ctggcccgta     3300
gccctcacgt gggtgtgaag gacgtggagt gtggggaagg acacttctgc catgataacc     3360
agacctgctg ccgagacaac cgacagggct gggcctgctg tccctacgcc caggtcagtg     3420
ccaacncatc ctggggntgg tatggccagg accaggtccn acctngtcca accctctcgc     3480
nnnnctctga ccatccaggg cgtctgttgt gctgatcggc gccactgctg tcctgctggc     3540
ttccgctgcg cagccagggg taccaagtgt ttgcgcaggg aggccccgcg ctgggacgcc     3600
cctttgaggg acccagcctt gagacagctg cttgtgaggg acagtactga agactctgca     3660
gccctcggga ccccactcgg agggtgccct ctgctcaggc ctccctagca cctcccccta     3720
accaaattct ccctggaccc cattctgagc tccccatcac catgggaggt ggggcctcaa     3780
tctaaggccc ttccctgtca gaaggggggtt gtggcaaaag ccacattaca agctgccatc    3840
ccctccccgt ttcagtggac cctgtggcca ggtgcttttc cctatccaca ggggtgtttg     3900
tgtgtgtgcg cgtgtgcgtt tcaataaagt ttgtacactt tctt                      3944
```

```
<210> SEQ ID NO 41
<211> LENGTH: 250
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(250)
<223> OTHER INFORMATION: This sequence may encompass 200-250 nucleotides

<400> SEQUENCE: 41
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
aaaaaaaaaa aaaaaaaaaa aaaaaaaaaa aaaaaaaaaa aaaaaaaaaa aaaaaaaaaa       180
aaaaaaaaaa aaaaaaaaaa aaaaaaaaaa aaaaaaaaaa aaaaaaaaaa aaaaaaaaaa       240
aaaaaaaaaa                                                             250
```

```
<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gcgatcctgc ttccaaagat                                                   20
```

```
<210> SEQ ID NO 43
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gtgaaccagg tcgcagaag                                                   19

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tgcttccaaa gatcaggtaa ca                                               22

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gccactgccc tgttagtc                                                    18

<210> SEQ ID NO 46
<211> LENGTH: 100
<212> TYPE: DNA
<213> ORGANISM: Homo sapiens

<400> SEQUENCE: 46
gtgcagctgg ggtgtgggtg cagggcaggc agacgggcag catgtggagt ctggaaccca      60
ggagcccagc tggcgggggc agccctgatt cctgcccttg                           100

<210> SEQ ID NO 47
<211> LENGTH: 83
<212> TYPE: DNA
<213> ORGANISM: Homo sapiens

<400> SEQUENCE: 47
gtgcagctgg ggtgtgggtg cagggcaggc agacgggcag catgtggagt ctggaaccca      60
ggagcccagc tggcgggggc agc                                              83

<210> SEQ ID NO 48
<211> LENGTH: 271
<212> TYPE: DNA
<213> ORGANISM: Homo sapiens

<400> SEQUENCE: 48
gtaggagagc ggccgcgcag acctctcgcc tgctcctgcc caggggcccg ccagggccat      60
gtgagcttga ggttcccctg gagtctcagc cggagacaac agaagaaccg cttactgaaa     120
ctccttgggg gttctgatac actaggggga gttttatggg aaagaggaag cagtaattgc     180
agtgacgccc cgttagaagg ggctttctac ctccccagca ttcccccaaa gcagggacca     240
caccattctt gacccagctc cacccctgtc g                                    271
```

ANTISENSE OLIGONUCLEOTIDE-BASED PROGRANULIN AUGMENTATION THERAPY IN NEURODEGENERATIVE DISEASES

CROSS-REFERENCE TO RELATED APPLICATIONS

This application is a 35 U.S.C. § 371 National Phase Entry Application of International Patent Application No. PCT/US2020/023663 filed on Mar. 19, 2020, which designated the U.S., which claims the benefit under 35 U.S.C. § 119(e) of U.S. Provisional Application Nos. 62/821,237 filed Mar. 20, 2019 and 62/838,156 filed Apr. 24, 2019, the content of each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 19, 2020, is named 002806-093760WOPT_SL.txt and is 37,437 bytes in size.

TECHNICAL FIELD

The technology described herein relates to the modulation of progranulin (GRN) expression or activity in the brain for the treatment of neurodegenerative diseases.

BACKGROUND

Neurodegenerative diseases occur when nervous system cells (neurons) in the brain and spinal cord begin to deteriorate. Today, 5.4 million Americans suffer from Alzheimer's disease; 500,000 from Parkinson's disease and 50,000-60,000 from frontotemporal dementia (FTD). Because neurodegenerative diseases strike primarily in mid- to late-life, the incidence is expected to soar as the population ages. By 2030, as many as 1 in 5 Americans will be over the age of 65. If left unchecked 30 years from now, more than 12 million Americans will suffer from neurodegenerative diseases. Finding treatments and cures for neurodegenerative diseases is a goal of increasing urgency.

Granulin (or progranulin) is a phylogenetically ancient, cysteine-rich, secreted protein, encoded by the GRN gene. Progranulin dysfunction, e.g., low activity and/or expression is known to contribute to the development and progression of a number of neurodegenerative diseases. Recent studies have shown that progranulin augmentation may have therapeutic effects in diverse neurodegenerative diseases including Alzheimer's disease (AD), frontotemporal dementia (FTD) and Parkinson's disease (PD). However, no treatment targeting progranulin augmentation in the brain is currently available. Therapeutic approaches that directly target progranulin dysfunction in the brain are necessary in order to provide effective treatment.

SUMMARY

Recent studies have shown that progranulin augmentation may have therapeutic effects in diverse neurodegenerative diseases including Alzheimer's disease (AD), frontotemporal dementia (FTD) and Parkinson's disease (PD). However, increasing the levels of therapeutic proteins including progranulin in vivo remains challenging.

Described herein is a method of targeting progranulin expression or activity in the brain by administering an antisense oligonucleotide (ASO) complementary to progranulin pre-mRNAs. Further described herein are methods of treating neurodegenerative diseases by administering these ASOs.

In one aspect, described herein is an antisense oligonucleotide (ASO) comprising an oligonucleotide of 8 to 40 linked nucleotides or modified nucleotides in length, wherein the ASO comprises a nucleobase sequence targeting a Progranulin (GRN) mRNA to increase GRN expression or activity.

In one embodiment of any of the aspects, the ASO comprises an oligonucleotide of 12 to 40 linked nucleotides in length, which oligonucleotides comprise a sequence:
   a. at least 80% homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and
   b. wherein the oligonucleotide comprises at least one modified nucleotide.

In another embodiment of any of the aspects, the ASO comprises an oligonucleotide of 12 to 40 linked nucleotides in length, which oligonucleotides comprise a sequence:
   a. at least 90% homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and
   b. wherein the oligonucleotide comprises at least one modified nucleotide.

In another embodiment of any of the aspects, the ASO comprises an oligonucleotide of 12 to 40 linked nucleotides nucleotides in length, which oligonucleotides comprise a sequence:
   a. at least 100% homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and
   b. wherein the oligonucleotide comprises at least one modified nucleotide.

In another embodiment of any of the aspects, the ASO increase GRN expression or activity in the central nervous system.

In another embodiment of any of the aspects, the disease or disorder is selected from Alzheimer's disease, Frontotemporal Dementia, Batten disease and Parkinson's disease.

In another embodiment of any of the aspects, said progranulin (GRN) expression or activity in the brain is modulated by splicing of a pre-mRNA target.

In another embodiment of any of the aspects, the ASO comprises an oligonucleotide of 12 to 40 linked nucleotides in length, which oligonucleotides comprise at least one modified nucleotide which comprises a modified sugar moiety.

In another embodiment of any of the aspects, the ASO comprises a 2' modification of its sugar moiety.

In another embodiment of any of the aspects, the ASO comprises a 2'-o-methyl, 2'-methoxyethoxy, 2'-dimethylaminooxyethoxy, 2'-dimethylaminoethoxyethoxy, 2'-fluoro or 2'-acetamide modification on every sugar moiety.

In another embodiment of any of the aspects, the ASO comprises a LNA nucleobase.

In another embodiment of any of the aspects, the ASO comprises at least one modified linkage.

In another embodiment of any of the aspects, the linkage of the ASO comprises a phosphodiester, phosphotrester, or phosphorothioate backbone linkage.

In another embodiment of any of the aspects, the ASO is a morpholino or peptide nucleic acid.

In another embodiment of any of the aspects, the ASO comprises at least one modified base which increases binding affinity for the pre-mRNA target, which increases nuclease resistance of the antisense compound, or which decrease immune-stimulation.

In another embodiment of any of the aspects, the modified base is methyl-C.

In another embodiment of any of the aspects, the ASO is a mixture of one or more steropure molecules with a defined sequence.

In one aspect, described herein is an antisense oligonucleotide (ASO) comprising an oligonucleotide of 8 to 40 linked nucleotides or modified nucleotides in length, wherein the ASO comprises a nucleobase sequence with homology to a 5' untranslated region (5' UTR) of a progranulin (GRN) and wherein the ASO increases GRN expression or activity in the brain.

In one embodiment of any of the aspects, the ASO comprises an oligonucleotide of 8 to 40 linked nucleotides in length, which oligonucleotides comprise a sequence: a. at least 80% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

In another embodiment of any of the aspects, the ASO comprises an oligonucleotide of 8 to 40 linked nucleotides in length, which oligonucleotides comprise a sequence: a. at least 90% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

4

In another embodiment of any of the aspects, the ASO comprises an oligonucleotide of 8 to 40 linked nucleotides in length, which oligonucleotides comprise a sequence:
a. at least 100% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and
b. wherein the oligonucleotide comprises at least one modified nucleotide.

In another embodiment of any of the aspects, the ASO modulates the splicing of the pre-mRNA target.

In another embodiment of any of the aspects, the ASO targets an intron-exon or exon-intron junction of the pre-mRNA target.

In another embodiment of any of the aspects, the ASO targets a splicing enhancer or silencer element in the pre-mRNA target.

In another embodiment of any of the aspects, the ASO increases progranulin expression or activity in the brain by regulating translation efficiency of the pre-mRNA target.

In another embodiment of any of the aspects, the ASO increases progranulin expression or activity in the brain by regulating nuclear export of the pre-mRNA target.

In another embodiment of any of the aspects, the ASO increases progranulin expression or activity in the brain by regulating stability of the pre-mRNA target.

In another embodiment of any of the aspects, the ASO comprises an oligonucleotide of 8 to 40 linked nucleotides in length, which oligonucleotides comprise at least one modified nucleotide which comprises a modified sugar moiety.

In another embodiment of any of the aspects, the ASO comprises a 2' modification of its sugar moiety.

In another embodiment of any of the aspects, the ASO comprises a 2'-O-methyl, 2'-O-methoxyethyl, 2'-dimethylaminooxyethoxy, 2'-dimethylaminoethoxyethoxy, 2'-fluoro or 2'-acetamide modification on every sugar moiety.

In another embodiment of any of the aspects, the ASO comprises a LNA nucleobase.

In another embodiment of any of the aspects, the ASO comprises at least one modified linkage.

In another embodiment of any of the aspects, the linkage of the ASO comprises a phosphodiester, phosphotriester, or phosphorothioate backbone linkage.

In another embodiment of any of the aspects, the ASO is a morpholino or peptide nucleic acid.

In another embodiment of any of the aspects, the ASO comprises at least one modified base which increases binding affinity for the pre-mRNA target, which increases nuclease resistance of the antisense compound, or which decrease immune-stimulation.

In another embodiment of any of the aspects, the ASO comprises 5-methyl-C as a modified base.

In another embodiment of any of the aspects, the ASO is a mixture of one or more stereopure molecules with a defined sequence.

In one aspect described herein is a composition comprising an ASO and a pharmaceutically acceptable carrier.

In one aspect of any of the aspects, described herein is a method of increasing the level of progranulin mRNA in a cell comprising contacting the cell with an ASO, such that the level of progranulin mRNA in the cell is increased.

In one aspect described herein is a method of treating a neurodegenerative disease or disorder, the method comprising administering to a subject in need thereof, a therapeutically effective amount of an ASO thereby treating the disease or disorder.

In one embodiment of any of the aspects, the ASO modulates the splicing of the pre-mRNA target.

In another embodiment of any of the aspects, the ASO targets an intron-exon or exon-intron junction of the pre-mRNA target.

In another embodiment of any of the aspects, the modulation of splicing comprises direct binding of the ASO within 50 nucleobases upstream or downstream of an intron-exon or exon-intron junction, thereby causing a decreased frequency of use of the 5' or 3' splice site region of the pre-mRNA target.

In another embodiment of any of the aspects, the ASO targets a splicing enhancer or silencer element in the pre-mRNA target.

In another embodiment of any of the aspects, the modulation of splicing comprises a preferential inclusion of a segment of the pre-mRNA into a mature mRNA through inclusion of an alternative exon, extension of an exon at either 5' or 3' end, or retention of an intron.

In another embodiment of any of the aspects, the modulation of splicing comprises a preferential exclusion of a segment of the pre-mRNA from a mature mRNA through exclusion of an alternative exon, truncation of an exon at either 5' or 3' end, or enhanced splicing of an intron.

In another embodiment of any of the aspects, the modulation of splicing comprises the direct binding of an ASO at a splicing enhancer or silencer element, thereby causing a decreased effect of the splicing enhancer or silencer element in the pre-mRNA target.

In another embodiment of any of the aspects, the disease or disorder is selected from Alzheimer's disease, frontotemporal dementia, Batten disease and Parkinson's disease.

In one aspect, described herein is a method of screening for an antisense oligonucleotide (ASO) that leads to enhanced gene expression of a selected pre-mRNA target, comprising: a. determining or having determined whether a mammalian pre-mRNA is subject to alternative splicing involving at least part the 5' untranslated region (5' UTR) of the pre-mRNA based on gene annotations from public databases and/or RNA-seq reads obtained from mammalian biological samples, and b. obtaining or having obtained mammalian culturable cells that express the mRNA isoforms that are alternatively spliced in the 5' UTR region; and c. determining or having determined an mRNA isoform that is alternatively spliced in the 5' UTR region that gives rise to higher expression efficiency; by (i) determining or having determined an mRNA isoform with less upstream open reading frames (uORFs) by counting the occurrences of the "AUG" start codon and/or the Kozak consensus sequence; and/or by (ii) determining or having determined an mRNA isoform with higher nuclear export efficiency by obtaining mammalian biological samples, isolating cytoplasmic and nuclear fraction of the mRNA from the samples, and quantifying the amount of the isoforms in cytoplasm compared to nucleus; and/or by (iii) determining or having determined an mRNA isoform with higher stability by treating transcription inhibitor such as Actinomycin D to the said mammalian culturable cells and measuring the level of the 5' UTR splice isoforms at fixed time points post inhibition of transcription. d. designing an ASO targeting the said selected pre-mRNA target that promotes preferential splicing of the pre-mRNA into the isoform with higher expression efficiency, and e. contacting the said cell or animal model with an ASO targeting the said selected pre-mRNA target, which results in preferential splicing of the pre-mRNA into the isoform with higher expression efficiency.

In one aspect, described herein is a composition comprising an ASO and a pharmaceutically acceptable carrier for use in the treatment of a neurodegenerative disease or disorder.

In one embodiment of any of the aspects, comprising an ASO of 8 to 40 linked nucleotides or modified nucleotides in length, wherein the ASO comprises a nucleobase sequence with homology to a 5' untranslated region (5' UTR) of a progranulin (GRN) and wherein the ASO increases GRN expression or activity in the brain.

In another embodiment of any of the aspects, the ASO comprises an oligonucleotide of 8 to 40 linked nucleotides in length, which oligonucleotides comprise a sequence: a. at least 80% homologous to a nucleotide sequence that is selected from the group consisting of SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

In another embodiment of any of the aspects, the ASO comprises an oligonucleotide of 8 to 40 linked nucleotides in length, which oligonucleotides comprise a sequence:

a. at least 90% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

In another embodiment of any of the aspects, the ASO comprises an oligonucleotide of 8 to 40 linked nucleotides in length, which oligonucleotides comprise a sequence:

a. at least 100% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

In another embodiment of any of the aspects, the ASO modulates the splicing of the pre-mRNA target.

In another embodiment of any of the aspects, the ASO targets an intron-exon or exon-intron junction of the pre-mRNA target.

In another embodiment of any of the aspects, the ASO targets a splicing enhancer or silencer element in the pre-mRNA target.

In another embodiment of any of the aspects, the ASO increases progranulin expression or activity in the brain by regulating translation efficiency of the pre-mRNA target.

In another embodiment of any of the aspects, the ASO increases progranulin expression or activity in the brain by regulating nuclear export of the pre-mRNA target.

In another embodiment of any of the aspects, the ASO increases progranulin expression or activity in the brain by regulating stability of the pre-mRNA target.

In another embodiment of any of the aspects, the ASO comprises an oligonucleotide of 8 to 40 linked nucleotides in length, which oligonucleotides comprise at least one modified nucleotide which comprises a modified sugar moiety.

In another embodiment of any of the aspects, the ASO comprises a 2' modification of its sugar moiety.

In another embodiment of any of the aspects, the ASO comprises a 2'-O-methyl, 2'-O-methoxyethyl, 2'-dimethyl-aminooxyethoxy, 2'-dimethylaminoethoxyethoxy, 2'-fluoro or 2'-acetamide modification on every sugar moiety.

In another embodiment of any of the aspects, the ASO comprises a LNA nucleobase.

In another embodiment of any of the aspects, the ASO comprises at least one modified linkage.

In another embodiment of any of the aspects, the linkage of the ASO comprises a phosphodiester, phosphotriester, or phosphorothioate backbone linkage.

In another embodiment of any of the aspects, the ASO is a morpholino or peptide nucleic acid.

In another embodiment of any of the aspects, the ASO comprises at least one modified base which increases binding affinity for the pre-mRNA target, which increases nuclease resistance of the antisense compound, or which decrease immune-stimulation.

In another embodiment of any of the aspects, the ASO comprises 5-methyl-C as a modified base.

In another embodiment of any of the aspects, the ASO is a mixture of one or more stereopure molecules with a defined sequence.

In another embodiment of any of the aspects, the ASO modulates the splicing of the pre-mRNA target.

In another embodiment of any of the aspects, the ASO targets an intron-exon or exon-intron junction of the pre-mRNA target.

In another embodiment of any of the aspects, the modulation of splicing comprises direct binding of the ASO within 50 nucleobases upstream or downstream of an intron-exon or exon-intron junction, thereby causing a decreased frequency of use of the 5' or 3' splice site region of the pre-mRNA target.

In another embodiment of any of the aspects, the ASO targets a splicing enhancer or silencer element in the pre-mRNA target.

In another embodiment of any of the aspects, the modulation of splicing comprises a preferential inclusion of a segment of the pre-mRNA into a mature mRNA through inclusion of an alternative exon, extension of an exon at either 5' or 3' end, or retention of an intron.

In another embodiment of any of the aspects, the modulation of splicing comprises a preferential exclusion of a segment of the pre-mRNA from a mature mRNA through exclusion of an alternative exon, truncation of an exon at either 5' or 3' end, or enhanced splicing of an intron.

In another embodiment of any of the aspects, the modulation of splicing comprises the direct binding of an ASO at a splicing enhancer or silencer element, thereby causing a decreased effect of the splicing enhancer or silencer element in the pre-mRNA target.

In another embodiment of any of the aspects, the disease or disorder is selected from the group of Alzheimer's disease, frontotemporal dementia, Batten disease, and Parkinson's disease.

In another aspect, described herein is a method of treating a neurodegenerative disease or disorder, the method comprising administering to a subject in need thereof, a therapeutically effective amount of an antisense oligonucleotide (ASO) targeting an intron of a Progranulin (GRN) mRNA to increase GRN expression or activity in the brain, thereby treating the disease or disorder.

In one embodiment of any of the aspects, the ASO comprises an oligonucleotide of 12 to 40 linked nucleotides in length, which oligonucleotides comprise a sequence:
   a. at least 80% homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and
   b. wherein the oligonucleotide comprises at least one modified nucleotide.

In another embodiment of any of the aspects, the ASO comprises an oligonucleotide of 12 to 40 linked nucleotides in length, which oligonucleotides comprise a sequence:
   a. at least 90% homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and
   b. wherein the oligonucleotide comprises at least one modified nucleotide.

In another embodiment of any of the aspects, the ASO comprises an oligonucleotide of 12 to 40 linked nucleotides nucleotides in length, which oligonucleotides comprise a sequence:
   a. at least 100% homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and
   b. wherein the oligonucleotide comprises at least one modified nucleotide.

In another embodiment of any of the aspects, the disease or disorder is selected from Alzheimer's disease, Fronto-temporal Dementia, Batten disease and Parkinson's disease.

In another embodiment of any of the aspects, said progranulin (GRN) expression or activity in the brain is modulated by splicing of a pre-mRNA target.

In another embodiment of any of the aspects, the ASO comprises an oligonucleotide of 12 to 40 linked nucleotides in length, which oligonucleotides comprise at least one modified nucleotide which comprises a modified sugar moiety.

In another embodiment of any of the aspects, the ASO comprises a 2' modification of its sugar moiety.

In another embodiment of any of the aspects, the ASO comprises a 2'-o-methyl, 2'-methoxyethoxy, 2'-dimethylaminooxyethoxy, 2'-dimethylaminoethoxyethoxy, 2'-fluoro or 2'-acetamide modification on every sugar moiety.

In another embodiment of any of the aspects, the ASO comprises a LNA nucleobase.

In another embodiment of any of the aspects, the ASO comprises at least one modified linkage.

In another embodiment of any of the aspects, the linkage of the ASO comprises a phosphodiester, phosphotrester, or phosphorothioate backbone linkage.

In another embodiment of any of the aspects, the ASO is a morpholino or peptide nucleic acid.

In another embodiment of any of the aspects, the ASO comprises at least one modified base which increases binding affinity for the pre-mRNA target, which increases nuclease resistance of the antisense compound, or which decrease immune-stimulation.

In another embodiment of any of the aspects, the modified base is methyl-C.

In another embodiment of any of the aspects, the ASO is a mixture of one or more steropure molecules with a defined sequence.

In another aspect, described herein is a pharmaceutical composition comprising an ASO homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39 and a pharmaceutically acceptable carrier for use in a method of treating a neurodegenerative disease or disorder.

Definitions

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, a polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to an assay known in the art or described below herein. A functional fragment can comprise conservative substitutions of the sequences disclosed herein.

In some embodiments, a polypeptide described herein can be a variant of a polypeptide or molecule as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

As used herein, the term "complementary", refers to the capacity for precise pairing between two nucleotides. An antisense oligonucleotide (ASO) may be at least 80% complementary to (optionally one of at least 85%, 90%, 91%, 92%, 93%, 94%, 95%, 96%, 97%, 98%, 99% or 100% complementary to) the consecutive nucleotides of a human progranulin gene. In some embodiments, the ASO may contain 1, 2, or 3 base mismatches compared to the portion of the consecutive nucleotides of a GRN-associated region. In some embodiments the single stranded oligonucleotide may have up to 3 mismatches over 15 bases, or up to 2 mismatches over 10 bases. It is understood in the art that a complementary nucleotide sequence need not be 100% complementary to that of its target to be specifically hybridizable. In some embodiments, a complementary nucleic acid sequence for purposes of the present disclosure is specifically hybridizable when binding of the sequence to the target molecule (e.g., pre-mRNA) interferes with the normal function of the target (e.g., pre-mRNA) to cause a loss of activity and there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency.

As used herein, the term "neurodegenerative diseases or disorder" refers to a group of disease or disorder that affect the structure or function of the brain and/or spinal cord. Neurodegenerative diseases occur as a result of neurodegenerative processes, e.g. the progressive loss of structure or function of neurons, including but not limited to the death of neurons. Neurodegenerative diseases include but are not limited to Amyotrophic lateral sclerosis, Parkinson's disease, Alzheimer's disease, Huntington's disease, and Batten disease.

As used herein, the term "nucleotide" refers to an organic molecule that serves as the monomer unit for forming the nucleic acid polymers deoxyribonucleic acid (DNA) and ribonucleic acid (RNA). Nucleotides are the building blocks of nucleic acids and are composed of three subunit molecules: a nitrogenous base, a five-carbon sugar, and at least one phosphate group. Nucleotides can be modified. The preparation of modified nucleic acids, backbones, and nucleobases described above are well known in the art. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Modified nucleotides can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2—NH—CH2—, —CH2—N(CH3)—O—CH2—[known as a methylene (methylimino) or MMI backbone], —CH2—O—N(CH3)—CH2—, —CH2—N(CH3)—N(CH3)—CH2— and —N(CH3)—CH2—CH2—[wherein the native phosphodiester backbone is represented as —O—P—O—CH2—].

As used herein, an "antisense oligonucleotide (ASO)" refers to a synthesized nucleic acid sequence that is complementary to a target DNA or mRNA sequence. Antisense oligonucleotides are typically designed to increase expression of a DNA or RNA target by binding to the target and modulation the expression or activity at the level of transcription, translation, or splicing. Antisense oligonucleotides are generally designed to hybridize under cellular conditions to a gene, e.g., the progranulin gene, or to its transcript. Thus, oligonucleotides are chosen that are sufficiently complementary to the target, i.e., that hybridize sufficiently well and with sufficient specificity in the context of the cellular environment, to give the desired effect. For example, an antisense oligonucleotide that inhibits progranulin may comprise at least 5, at least 10, at least 15, at least 20, at least 25, at least 30, or more bases complementary to a portion of the coding sequence of the human progranulin gene (e.g., NCBI Gene ID: 2896), respectively.

As used herein, the "5' untranslated region (5' UTR)" refers to a region of an mRNA that is important for the regulation of translation of a transcript by differing mechanisms in viruses, prokaryotes and eukaryotes. The 5' UTR begins at the transcription start site and ends one nucleotide (nt) before the initiation sequence (usually AUG) of the coding region. In eukaryotes, the length of the 5' UTR tends to be tends to be anywhere from at least 10, or at least 20, or at least 30, or at least 40, or at least 50, or at least 60, or at least 70, or at least 80, or at least 90, or at least 100, or at least 200, or at least 400, or at least, 600, or at least 800, or at least 1000, or at least 2000, or at least 3000 or at least 4000 or at least 5000, or at least 6000, or at least 7000, or at least 8000, or at least 9000, or at least 10000, or at least 15000 nucleotides long.

As used herein, an "exon" refers to any part of a gene that will encode a part of the final mature RNA produced by that gene after introns have been removed by RNA splicing. The term exon refers to both the DNA sequence within a gene and to the corresponding sequence in RNA transcripts.

As used herein, an "intron" refers to any nucleotide sequence within a gene that is removed by RNA splicing during maturation of the final RNA product. The term intron refers to both the DNA sequence within a gene and the corresponding sequence in RNA transcripts. Group I and group II introns are found in genes encoding proteins (messenger RNA), transfer RNA and ribosomal RNA in a very wide range of living organisms. Following transcription into RNA, group I and group II introns also make extensive internal interactions that allow them to fold into a specific, complex three-dimensional architecture. These complex architectures allow some group I and group II introns to be self-splicing, that is, the intron-containing RNA molecule can rearrange its own covalent structure so as to precisely remove the intron and link the exons together in the correct order.

As used herein, the term "alternative splicing" refers to a regulated process during gene expression that results in a single gene coding for multiple proteins. In this process, particular exons of a gene may be included within or excluded from the final, processed messenger RNA (mRNA) produced from that gene.

As used herein, the term "exon skipping" refers to an exon that may be spliced out of the primary transcript or retained.

As used herein, the term "mutually exclusive exons" refers to one of two exons that is retained in mRNAs after splicing, but not both.

As used herein, the term "alternative donor site" refers to an alternative 5' splice junction that is used, changing the 3' boundary of the upstream exon.

As used herein, the term "alternative acceptor site" refers to an alternative 3' splice junction that is used, changing the 5' boundary of the downstream exon.

As used herein, an "Exonic splicing enhancer" or "ESE" refers to a DNA sequence motif consisting of 6 bases within an exon that directs, or enhances, accurate splicing of heterogeneous nuclear RNA (hnRNA) or pre-mRNA into messenger RNA (mRNA).

As used herein, an "exonic splicing silencer" or "ESS" is a short region (usually 4-18 nucleotides) of an exon and is a cis-regulatory element. ESSs inhibit or silence splicing of the pre-mRNA and contribute to constitutive and alternate splicing. To elicit the silencing affect, ESSs recruit proteins that will negatively affect the core splicing machinery.

As used herein, the term "Intron retention" refers to a sequence may be spliced out as an intron or simply retained. This is distinguished from exon skipping because the retained sequence is not flanked by introns.

As used herein, the term "gapmer" refers to a chimeric antisense oligonucleotide that contains a central block of deoxynucleotide monomers sufficiently long to induce RNase H cleavage.

The term "therapeutically effective amount" refers to an amount of the ASOs described herein, using the methods as disclosed herein, that is sufficient to provide a particular effect when administered to a typical subject. An effective amount as used herein would also include an amount sufficient to delay the development of a symptom of the disease, alter the course of a symptom of a disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

The terms "increased", "increase", "enhance", or "activate" are all used herein to refer to an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

The term "modulation" refers to stimulation; i.e., an increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects of antisense oligonucleotides of the present invention on progranulin expression can also be determined as taught in the examples of the instant application. Inhibition is presently a preferred form of modulation.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of diseases including TSC. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

As used herein, a "subject in need" of treatment for a particular condition can be a subject having that condition, diagnosed as having that condition, or at risk of developing that condition.

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

BRIEF DESCRIPTION OF THE DRAWINGS

FIG. 1A. Substantial retention of GRN intron 4 (length ~480 bp) in human brain tissues in GTEx. FIG. 1B. BodyMap and GEO RNA-seq datasets. FIG. 1C. ASO-mediated blockage of splicing regulatory elements to reduce intron retention and boost functional protein expression. ISS, intronic splice silencer; ESS, exonic splice silencer.

FIG. 2A. Ranking of 933 CCLE cell lines based on GRN intron retention level. FIG. 2B. Top three and bottom three cell lines with respect to GRN intron 4 retention level. GTEx brain cortex tissue was shown on top for comparison. PIR, percent intron retention.

FIGS. 4A-4C demonstrates a reverse transcription (RT)-PCR assay for measuring the ratio of the intron 4-spliced vs. unspliced form of GRN mRNA. FIG. 4A. A schematic showing the locations of the forward (F) and reverse (R) primers on GRN mRNA/cDNA. FIG. 4B. PCR products corresponding to the intron 4-spliced (lower band, 199 bp) and unspliced (upper band, 675 bp) form. FIG. 4C. Forward and reverse primer sequences (SEQ ID NOS 42 and 43, respectively, in order of appearance).

FIG. 5A. A schematic showing the locations of the forward (F) and reverse (R) primers on GRN mRNA/cDNA. FIG. 5B. PCR products corresponding to the GRN PCR product (upper, 269 bp) and GAPDH PCR product (lower). FIG. 5C. The forward and reverse primer sequences (SEQ ID NOS 44 and 45, respectively, in order of appearance) for the GRN PCR.

FIG. 6A discloses SEQ ID NO: 46. FIG. 6B discloses SEQ ID NO: 47.

FIG. 7A. A schematic showing the locations of the forward and reverse primers on GRN mRNA/cDNA. FIG. 7B. The levels of the intron 4-spliced and unspliced forms of GRN at transfection of respective ASOs. Ctrl and S01 are control ASOs. SPIN is Spinraza. RNAs were prepared 48 hours after transfection (200 nM). FIG. 7C. The percent intensity of each of the upper (E4-I4-E5) and lower (E4-E5) band in the gel image, such as one shown in panel B. Error bars indicate standard errors. N=5, *p<0.05, two-sided t test. FIG. 7D. Fold difference in the ratio of the intron 4-spliced vs. unspliced form of GRN: indicated ASOs vs. Ctrl.

FIG. 8A. The levels of the intron 4-spliced and unspliced forms of GRN mRNA at transfection of indicated ASOs at indicated concentration. RNAs were prepared at indicated time points after transfection. Control (Ctrl), SP, and S01 are control ASOs. SP is Spinraza. Control (Ctrl), SP, and S01 are transfected at 200 nM. FIG. 8B. The fold difference in the ratio of the intron 4-spliced vs. unspliced form of GRN: indicated ASOs at indicated concentration vs. Control (Ctrl) at 200 nM. Error bars indicate standard errors. N=5, *p<0.05, two-sided t test.

FIG. 9A. A schematic showing the locations of the forward and reverse primers on GRN mRNA/cDNA. FIG. 9B. The levels of the intron 4-spliced form of GRN mRNA and GAPDH mRNA at transfection of indicated ASOs at indicated concentration. RNAs were prepared 48 hours after transfection. Control (Ctrl), SPIN, and S01 are negative control ASOs. SPIN is Spinraza. Control (Ctrl), SPIN, and S01 were transfected at 200 nM concentration. FIG. 9C. The fold difference in the level of the GRN RT-PCR product: indicated ASOs at indicated concentration vs. Control (Ctrl) at 200 nM, each normalized by the level of GADPH PCR product. Error bars indicate standard errors. N=5, *p<0.05, two-sided t test.

DETAILED DESCRIPTION

Figure 1A:
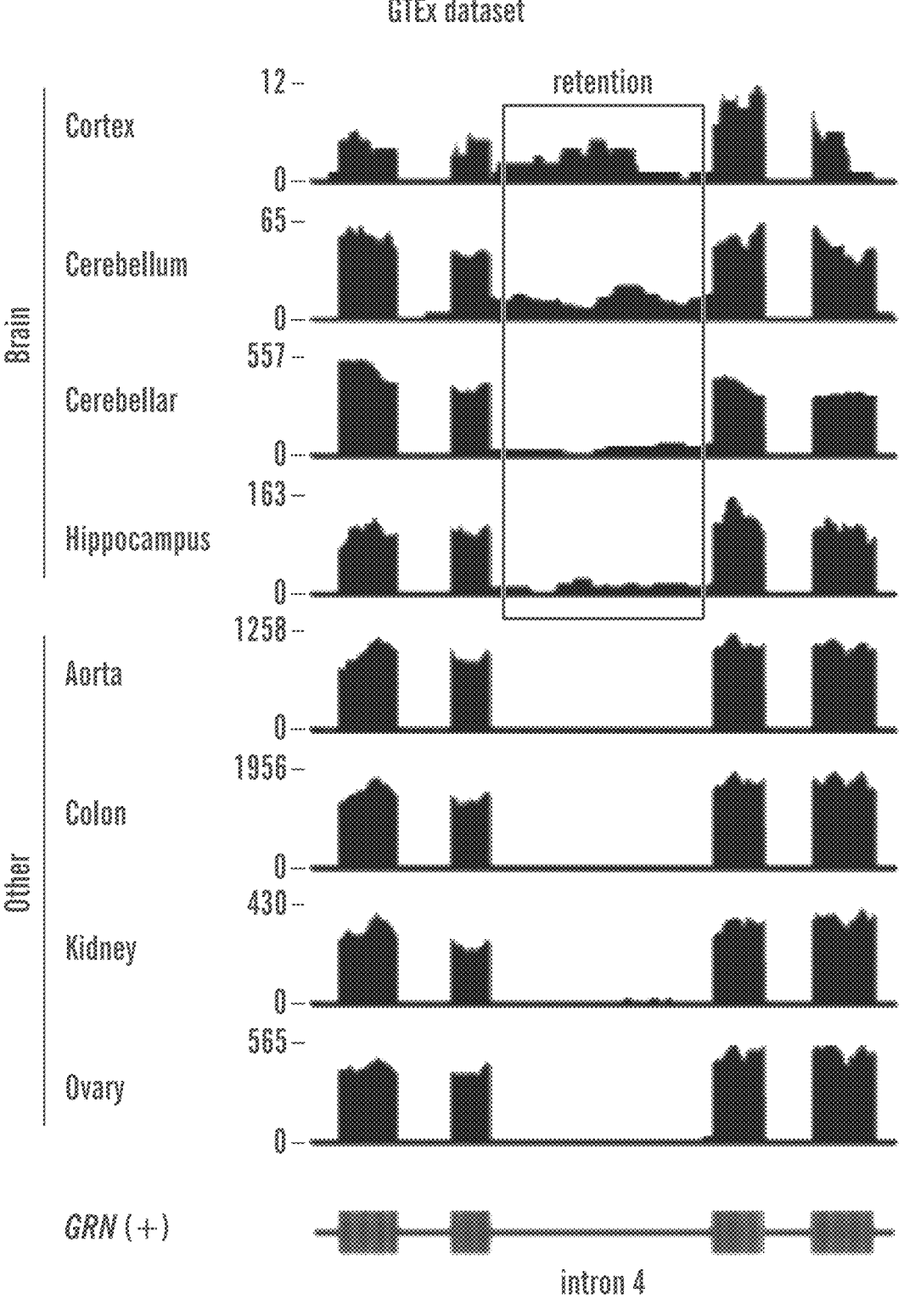
FIGS. 1A-1C demonstrate the GRN intron 4 retention.

The methods and compositions described herein are based, in part on the discovery that the protein progranulin plays a critical neuroprotective function when secreted into cerebrospinal fluid. Granulin (or progranulin) is a phylogenetically ancient, cysteine-rich, secreted protein, encoded by the GRN gene. Progranulin dysfunction, e.g., low activity and/or expression is known to contribute to the development and progression of a number of neurodegenerative diseases. Recent studies have shown that progranulin augmentation may have therapeutic effects in diverse neurodegenerative diseases including Alzheimer's disease (AD), frontotemporal dementia (FTD) and Parkinson's disease (PD).

Increasing the levels of progranulin in vivo remains challenging. Antisense oligonucleotides (ASOs) are often used to downregulate gene expression1 or to modify RNA splicing, but antisense technology has not previously been used to directly increase the production of progranulin.

Briefly, the methods described herein are methods and related antisense stranded oligonucleotides that elevate progranulin protein levels in cells (e.g., cells of a GRN-related frontotemporal dementia patient), e.g., by increasing progranulin transcription and correcting its splicing, are provided herein. Further aspects of the disclosure are described in detail herein.

In some embodiments of any of the aspects, provided herein is a method of treating a neurodegenerative disease or disorder (including but not limited to GRN-related frontotemporal dementia Alzheimer's disease, frontotemporal dementia, Batten disease and Parkinson's disease), the method comprising administering to a subject in need thereof, a therapeutically effective amount of an antisense oligonucleotide (ASO) targeting a 5' untranslated region (5' UTR) region of a progranulin pre-mRNA to increase progranulin expression or activity in the brain, thereby treating the disease or disorder.

In some embodiments of any of the aspects, provided herein are methods of modulating gene expression that may be carried out in vitro, ex vivo, or in vivo. It is understood that any reference to uses of compounds throughout the description contemplates use of the compound in preparation of a pharmaceutical composition for use in the treatment of condition (e.g., GRN-related frontotemporal dementia, Alzheimer's disease, frontotemporal dementia, Batten disease and/or Parkinson's disease) associated with decreased levels or activity of progranulin. Thus, as one nonlimiting example, this aspect of the disclosure includes use of such single stranded oligonucleotides in the preparation of a medicament for use in the treatment of disease, wherein the treatment involves upregulating expression of progranulin.

In one embodiment, provided herein is a method of screening for an antisense oligonucleotide (ASO) that leads to enhanced gene expression of a selected pre-mRNA target Progranulin GRN has been primarily known for causal genetic links to frontotemporal dementia (FTD) and Batten disease. However, recent studies have shown that progranulin augmentation may have also therapeutic effects in diverse neurodegenerative diseases including Alzheimer's disease and Parkinson's disease, which in affect tens of millions of people worldwide. Specifically, GRN rs5848, a SNP that is linked to progranulin deficiency, was found to be associated with the risk of AD and PD in multiple studies (Chen et al., 2015). Progranulin deficiency was also reported to cause spurious microglia activation called "microgliosis," a hallmark of AD (Lui et al., 2016). In addition, recent studies showed that viral delivery of progranulin in mouse models of AD (Minami et al., 2014), PD (Van Kampen et al., 2014), FTD (Arrant et al., 2017), and Batten disease (Arrant et al., 2018) reduces respective disease pathology in a dose-dependent manner. Together, these studies point to progranulin enhancement as a promising treatment for the diseases.

However, no treatment targeting progranulin is available currently. Disclosed herein are ASOs targeting progranulin expression or activity for use in the treatment of neurodegenerative diseases.

Accordingly, as described herein, compositions and methods targeting progranulin can be used to provide novel therapeutic strategies for treating neurodegenerative diseases, such as Alzheimer's disease, frontotemporal dementia and Parkinson's disease.

Frontotemporal dementias (FTD) encompass six types of dementia involving the frontal or temporal lobes including behavioral variant of FTD, semantic variant primary progressive aphasia, nonfluent agrammatic variant primary progressive aphasia, corticobasal syndrome, progressive supranuclear palsy, and FTD associated with motor neuron disease.

FTD was first described by Arnold Pick in 1892 and was originally called "Pick's disease", a term now reserved for Pick disease, one specific type of frontotemporal dementia. FTD accounts for 20% of young-onset dementia cases. Signs and symptoms typically manifest in late adulthood, more commonly between the ages of 45 and 65, approximately equally affecting men and women. Common signs and symptoms include significant changes in social and personal behavior, apathy, blunting of emotions, and deficits in both expressive and receptive language. Currently, there is no cure for FTD, but there are treatments that help alleviate symptoms.

GRN-related frontotemporal dementia is a progressive brain disorder that can affect behavior, language, and movement. The symptoms of this disorder usually become noticeable in a person's fifties or sixties, and affected people typically survive 6 to 7 years after the appearance of symptoms. GRN-related frontotemporal dementia affects an estimated 3 to 15 per 100,000 people aged 45 to 64. This condition accounts for 5 to 10 percent of all cases of frontotemporal dementia.

GRN-related frontotemporal dementia results from mutations in the GRN gene. This gene provides instructions for making a protein called progranulin. Progranulin is active in many different tissues in the body, where it helps control the growth, division, and survival of cells. Progranulin's function in the brain is not well understood, although it appears to play an important role in the survival of nerve cells (neurons).

Most mutations in the GRN gene prevent any progranulin from being produced from one copy of the gene in each cell. As a result, cells make only half the usual amount of progranulin. It is unclear how a shortage of this protein leads to the features of GRN-related frontotemporal dementia. However, studies have shown that the disorder is characterized by the buildup of a protein called TAR DNA-binding protein (TDP-43) in certain brain cells. The TDP-43 protein forms clumps (aggregates) that may interfere with cell functions and ultimately lead to cell death. Researchers are working to determine how mutations in the GRN gene, and the resulting loss of progranulin, are related to a buildup of TDP-43 in the brain.

The features of GRN-related frontotemporal dementia result from the gradual loss of neurons in regions near the front of the brain called the frontal and temporal lobes. The frontal lobes are involved in reasoning, planning, judgment, and problem-solving, while the temporal lobes help process hearing, speech, memory, and emotion. The death of neurons in these areas causes problems with many critical brain functions. However, it is unclear why the loss of neurons occurs in the frontal and temporal lobes more often than other brain regions in people with GRN-related frontotemporal dementia.

Some people with GRN-related frontotemporal dementia also develop movement disorders, such as parkinsonism and corticobasal syndrome. The signs and symptoms of these disorders include tremors, rigidity, unusually slow movement (bradykinesia), involuntary muscle spasms (myoclonus), uncontrolled muscle tensing (dystonia), and an inability to carry out purposeful movements (apraxia).

Batten disease is a fatal disease of the nervous system that typically begins in childhood. Onset of symptoms is usually between 5 and 10 years of age. Often it is autosomal recessive. It is the most common form of a group of disorders called the neuronal ceroid lipofuscinoses (NCLs).

Although Batten disease is usually regarded as the juvenile form of NCL (or "type 3"), some physicians use the term Batten disease to describe all forms of NCL. Historically, the NCLs were classified by age of disease onset as infantile NCL (INCL), late infantile NCL (LINCL), juvenile NCL (JNCL) or adult NCL (ANCL).

As described herein, Batten disease can be caused by mutations in the gene that provides instructions to make the protein GRN. Batten involves the buildup of substances called lipofuscins, which consists of fats and proteins, within cells of the brain, eye, and skin.

In some embodiments of any of the aspects, the compositions and methods described herein target progranulin.

As used herein, "GRN", "PRGN" or "Progranulin" is a protein that is encoded by the GRN gene. The protein encoded by this gene is a protein of a family of secreted, glycosylated peptides that are cleaved from a single precursor protein with 7.5 repeats of a highly conserved 12-cysteine progranulin/epithelin motif.

Sequences for GRN are known for a number of species, e.g., human GRN (the GRN NCBI Gene ID is 2896) mRNA sequences (e.g., NM 002087.3) and polypeptide sequences (e.g., NP_002078.1).

These, together with any naturally occurring allelic, splice variants, and processed forms thereof that catalyze the same reaction are contemplated for use in the methods and compositions described herein.

In some embodiments, the GRN nucleic acid includes or is derived from human GRN having the following nucleic acid sequence L01117.1 (SEQ ID NO: 40).

```
gcagaccatg tggaccctgg tgagctgggt ggccttaaca gcagggctgg tggctggaac gcggtgccca gatggtcagt tctgccctgt ggcctgctgc ctggaccccg gaggagccag ctacagctgc tgccgtcccc ttctggtgag tgccctcagc ctaggcaaga gctggcagct gggttttcc aaagggtcat cttggattgg ccagaggagg acgccaggca caagtctgtg gtttatcatt ttccctgtct ttctaggaca aatggcccac aacactgagc aggcatctgg gtggcccctg ccaggttgat gcccactgct ctgccggcca ctcctgcatc tttaccgtct
```

-continued

```
cagggacttc cagttgctgc cccttcccag aggtgagcgt gccatcagcc caatggaggg gcttaggtct gcatttatgc ttttcctgca ctctaccacc tgcagataaa agggccctgc caatgcaggt ttctctgtgt tccacaggcc gtggcatgcg gggatggcca tcactgctgc ccacggggct tccactgcag tgcagacggg cgatcctgct tccaaagatc agGTGCAGCT

GGGGTGTGGG TGCAGGGCAG GCAGACGGGC AGCATGTGGA GTCTGGAACC CAGGAGCCCA

GCTGGCGGGG GCAGCCCTGA TTCCTGCCCT TGTGCCCTCA TTCATGTGGC ATCTGTACTA

AGCAACAGCc ctgctgtgga cagaggggca gcactgggga taggagggtg cgggagaaag tgcaagactc caggtccagg cgttgtgggg gtggggagag gtcgagctgg gccggtctaa taccaaccca tggtcagtgg gtgccccttt ccccatgcca tcttgctgag ggagggactg gattgtgagg agggtgagtt aggcctccta ggagatcact gagccttagt gtcaccctca aaccccagta gctgggcttg caggcctggt gccaccagct ccttgtgtga tgggggagtc agtcaccttc cctgagtggg ctggtagtat cctgggtcat cttgtccaca ggtaacaact ccgtgggtgc catccagtgc cctgatagtc agttcgaatg cccggacttc tccacgtgct gtgttatggt cgatggctcc tggggtgct gccccatgcc ccaggtacaa atctggggga gatggggata tgtggaggga agtgggggca gagttggggg cnaggcnagg gggtgaagac ggannnngga ccatttttnc tcaggcttcc tgctgtgaag acagggtgca ctgctgttcc gcacggtgcc ttctgcgacc tggttcacac ccgctgcatc acacccacgg gcacccaccc cctggcaaag aagctccctg cccagaggac taacagggca ggtgaggagg tgggagagca tcaggccagg ggctggggcn nnnctcattg actccaagtg taggaaaaag tttcctccat cctggctgcc cctcacgttt gctcctcttc cagtggcctt gtccagctcg gtcatgtgtc cggacgcacg gtcccggtgc cctgatggtt ctacctgctg tgagctgcca gtggaagtat ggctgctgcc caatgcccaa cgtgagtgag ggctgaacca gcttggctgt gtgccnncag ccacctganc ctgacacgca ccttanaggg gctctgtggc atggggctgg ctggctgctt gctgggancc tggctgatgc agggttcatg ctaccccta gtgggggatt ggggcagtgc cagccatcag cctggctgct ccctgtgtgc tactgagcct ggaagtgaca aagacccacc cctgtcccca ctcaggccac ctgctgctcc gatcacctgc actgctgccc ccaagacact gtgtgacctg atccagagta agtgcctctc caaggagaac gctaccacgg acctcctcac taagctgcct gcgcacacag gtaccagagg cagggtgcag atacaggggt gggnccccct ttcctccctt ttaggcctgg ccttaggatc actgcaaggt ggtgtaagcg gtaccctcca tcttcaacac ctggttccag ctgtggagcc ggcaaagggt tgatgccccn nnnggtcccc antnccactt ctgacctgtc ctctctgctt ccctcacagt gggggatgtg aaatgtgaca tggaggtgag ctgcccagat ggctatacct gctgccgtct acagtcgggg gcctgggggct gctgcccttt tacccaggta ccaggtgcgg cggtggctga gcacagtgtg cagcagccgg ccccagtgcc cacctgccct tcttcatctg ccctaggctg tgtgctgtga ggaccacata cactgctgtc ccgcggggtt tacgtgtgac acgcagaagg gtacctgtga acaggggccc caccaggtgc cctggtggag aaggccccag ctcacctcag cctgccagac ccacaagcct tgaagagaga tgtcccctgt gataatgtca gcagctgtcc ctcctccgat acctgctgcc aactcacgtc tggggagtgg ggctgctgtc caatcccaga ggtatatggg aggggacagc atcttggcct gggcaggtgg gtggccaagc tcctattgct ttctgccctc cgcatagccc ataggtgata cccagctctg acagattngt ccccagctgg aggtgctnta agagngagag
```

-continued

```
gcgggctnga gtaggtaggg gctcggnact tcgncccaca tagtggctac ctacaacgcc ctttcctgcc cacccccag gctgtctgct gctcggacca ccagcactgc tgcccccagg gctacacgtg tgtagctgag gggcagtgtc agcgaggaag cgagatcgtg gctggactgg agaagatgcc tgcccgccgg gcttccttat cccacccccag agacatcggc tgtgaccagc acaccagctg cccggtgggg cagacctgct gcccgagcct gggtgggagc tgggcctgct gccagttgcc ccatgtgagt gcctccctgc ctgcccctgg atagggggagc taagcccagt gagggagcta agcccagtga nggacaggaa cataatgcca ttctgtgctc ccttcccgcc aggctgtgtg ctgcgaggat cgccagcact gctgcccggc tggctacacc tgcaacgtga aggctcgatc ctgcgagaag gaagtggtct ctgcccagcc tgccaccttc ctggcccgta gccctcacgt gggtgtgaag gacgtggagt gtggggaagg acacttctgc catgataacc agacctgctg ccgagacaac cgacagggct gggcctgctg tccctacgcc caggtcagtg ccaacncatc ctggggntgg tatggccagg accaggtccn acctngtcca accctctcgc nnnnctctga ccatccaggg cgtctgttgt gctgatcggc gccactgctg tcctgctggc ttccgctgcg cagccagggg taccaagtgt ttgcgcaggg aggccccgcg ctgggacgcc cctttgaggg acccagcctt gagacagctg cttgtgaggg acagtactga agactctgca gccctcggga ccccactcgg agggtgccct ctgctcaggc ctccctagca cctcccccta accaaattct ccctggaccc cattctgagc tccccatcac catgggaggt ggggcctcaa tctaaggccc ttccctgtca gaaggggggtt gtggcaaaag ccacattaca agctgccatc ccctccccgt ttcagtggac cctgtggcca ggtgcttttc cctatccaca ggggtgtttg tgtgtgtgcg cgtgtgcgtt tcaataaagt ttgtacactt tctt
```

In some embodiments, the GRN nucleic acid includes or is derived from human GRN pre-mRNA having the following nucleic acid sequence NG_007886 (SEQ ID No. 1).

```
ATTCTCCAATCACATGATCCCTAGAAATGGGGTGTGGGGCGAGAGGAAGCAGGGAGGAGAGTGATTTGAG

TAGAAAAGAAACACAGCATTCCAGGCTGGCCCCACCTCTATATTGATAAGTAGCCAATGGGAGCGGGTAG

CCCTGATCCCTGGCCAATGGAAACTGAGGTAGGCGGGTCATCGCGCTGGGGTCTGTAGTCTGAGCGCTAC

CCGGTTGCTGCTGCCCAAGGACCGCGGAGTCGGACGCAGGTAGGAGAGCGGCCGCGCAGACCTCTCGCCT

GCTCCTGCCCAGGGGCCCGCCAGGGCCATGTGAGCTTGAGGTTCCCCTGGAGTCTCAGCCGGAGACAACA

GAAGAACCGCTTACTGAAACTCCTTGGGGGTTCTGATACACTAGGGGGAGTTTTATGGGAAAGAGGAAGC

AGTAATTGCAGTGACGCCCCGTTAGAAGGGGCTTTCTACCTCCCCAGCATTCCCCCAAAGCAGGGACCAC

ACCATTCTTGACCCAGCTCCACCCCTGTCGGTAGGTGCTGGCTTCTTCCCCTCTCCTGGTGGTGGTGGGT

GGTTCCCGCGGCGGCCTGGAGCCGGAGGGGCGCGCGACCCTGGGCTGGGAGCTCCGAGGGCCTGGGAACG

AGACCTGAGACCTTGGCTTCTCGAAGGTAGTAGGGACTTGGGAGTGGTGACTGAACCTGGTCTGGCTCCT

CCTTACTTCCTCTTGTTGCGGGTGGGACGAGCTAGCTTCCGCCTCTCCCAGCCACTTTTTCCTGCTCATT

TGCAGCTAGGTTGGCTCCCCTTTTGGGAATTTCCTCTCCCCTTGGCACTCGGAGTTGGGGGGTGCCACCT

AGTGGAAGATAACGGAGCTAGGGTCTTGAAGAGGCTGCTGTCCCCTCTGGCTGTTTTGGCGGTGTAGGGT

GGCATGAGAGACTGCGACTCGCCTCCTCATCCCTGTTTCTGTATGCGAGTGCTTGTATTCAGTAGAAGCA

TACACTATACTCCCTCAATTTAGGGTAAACAGGAGGGGCCACATGCACAGGTAATTCACCAGGGAGCCGA

ACACTCCTGTGCAGACAGACTCCCCTTCCCAGCAAGCCATGGCAGCGGACAGCCTGCTGAGAACACCCAG

GAAGCAGGCGGTGCCAGCTGCAGGTGCTTTGCCTGGGAGCTGTGGGGCTGAGGAGAGGGTCCACTGTCCA
```

-continued

```
GGACCAGTGAACTTCATCCTTATCTGTCCAGGAGGTGGCCTCTTGGGGATGCTGAGTTAGGGGAGGGGCA

CTTGAGGAAAGCCAGGTGGAGCAGAGAGGATGTGAGTGACTGGGTGGGTGAGATTTCCTGCCCCTCCCCC

CGCAGTGGTATCCACACCTAGACTCGTGGGGTAACTGAGGCACAGACAGAGAGCAACTTCTCAGGCCCTC

ACAGTTGGCAATTCTAGGATTAGGACCCAAGTGCGATTTTCAGGCAGTCCCTGTACCCTGTTTCTGTTGT

ACCTGTTGCACCATTCCCAGGCACTGCCCATCGTGCCACTAGTGATATGAACCCAGGTCCAATACGCTCT

GGGGCCATCAAAGCCTGACGTCACCATGACCTGATGTGTGACGTGTTATAGGTGTCCCTTGGTATCTTCA

CGGAACTGGTTCCAGGACCCCAAAATCTGTGGGTGCTCAAGCCCCTGAGATAAAATGGTGTAATATTTGC

ATATAACCTATACATACTTTAAATCATTTCTAGATTACTTATACCTAATACAATGGAAATGACATGTCGG

CTGGGCGTGGTGGCTCATGCCTGTAATCCCACCACTTTGGGAGGCCGTGGCAGGTGGATCACCTGAGGTC

TGGAGTTTGAGACCAGCCTGACCAACATGGTGAAACCCCCATCTCTACTAAAAATACAAAAATTAGCCAG

GTGTGGTAGCGCACACCTATAATCCCACCTACTTGGGAGGCTGAGGCAGGAGAATTGCTTGAACCTGGGA

GGCGGAGTTCGCAGTAAGCTGAGATCGCGCCACTGTACTACAGCCTGGGTGACAGAGCAGGACTCCATCT

CAAAAAAAAAAGAGAAAAAGAAAAAGAAATGCCATGTAAATAGTTGTGATCCTGAATTGTTTAGGGAATA

ATAAGAAAGAACTATCTGTAGATGTTCAGTATAGATGCACCCATCGTAAGCCTAACTACATTGTATAACT

CAGCAACGATGTAACATTTTCAGGGGTTTTTTGTTTTGTTTTTTGAGACAGAPTCTCAGTCTCACTCTG

TCACCCAGGCTGGAGTATGTTGGCGTGATCTCTGCTCACTGCAACCTCCACCTCCTGGGCTCAAGCGATT

CTCCTGCCTCAGCCTCTTGAGTAGCTGGGATTGCAGGTGTGCGCTACCACGCATGGCTAATTTTTGTATT

TTTAATAGAGATGGGGTTTTACCACGTTGGTCAGGCTGGTCTTGAACTCCTGACCTTGGGATCCGCCCAC

CTGGGCCTCCCAAAGTGCTGGGATTACAGGCGTTAGCCACCGCGCCCAATATATTTTGATCCCTGGTTGG

ATATGGAGGGCTGACTGTACTTAACATCTCTAAGCTTCAGTTTCCTCCTTTAAAATAAAGGTGTGGCTGG

GTGTGGTGGTTCAAGCCTGTAATCCCAGCACTTAGGGAGGCTGAGGTGGGTGGATCAGCTGAGGTCAGGA

GTTCAAGACCAGCCTGACCAATATGGTGAAACCCCCTCTCTGCTAAAAATACAAAAATTAGCCAGGCGTG

GTGGCGAGCGCCTGTAGTCCCAGCTACTTGCTTGAACTTGGGAGGCAGAGGTTGCAGTGAGCTGAGATCG

TGCCACTGAACTCGAGCATGGGCAACAGAGCAAGACTGTCTCAAAAAAAAAAAAAAAAAAGGGGGTGAGCA

GACGTGGTGGCACGCTCCCACAGTCCCAGCTACTTAGTAGGAGGCCAAGGTTGGAGGATTGCTTGATCCC

AGGAGTCTGAGTCCAGCCTGGGCAACATGGCAATACCTCATCTCTAAAAATAAAATAAAAGTAAAGGTAT

TAATTACTACTTTGGATGGTTGTTGCAAAGAAATATATATAAAATAATGGAGAGTCTTGTAACTGGCTCC

CAAGAGGCTCAACAGACATTACTGTTTTTGCTTCTTCATTATGAGTTACCTCTCTGGCCACCCCACTGAA

CTAGCTGGGCTAGCTGAGCCTGGGAGAAGAGTTGTTTAGGAAGTGAGAGGCTGCTCTCCACAGAGACTCA

AGGCTCAGTTCCTCCTGGTGACTCAGATGGGCAGCCCAGTGGGCACACGTGGTCTCTCTCCACATGTGGC

TGAGTTTCACTTCCAGAATAGATGGAGAGGCAAGGGCAGGGTTTAGCATGCTTGAGGAATCTCAGAGGGC

CCTGGTGGTGTGGGGGACCCTCAGAACACAGGTGTCTCAAGGGCTGACCCAGCTTCTGTGTCCTTTTCTC

TGGGTGAGGAGGGGACATTCATGGGCAGATGGTGACCTCTGGGGAAGGCAGCCCAGACTCCACTGGCCAC

CATATTTCCTTTTTCACAACTTTCTCACCCCTGTGGTTTCCCATGTCATCATGTGGCCGCTTCCCGCAAG

GCCTTAGCGGGGTGCAGGTATGAACATAGTGTCAGGCAAGGAGGCATCTGGAGGGGAACCCTGGCTTTTC

CTGGGGGGACTCCCTCCCTGCACCCTAGCCCTGTCCTCTCCCATGGCTACTGATGCCTTCCCCTCACCCC

AGAGGTGGCCCACATCTGCACAGATCAGACCCACAAAAATCACGTCTTCCTGACTCTCATAAGCCTGCCC

AGTGAGGCCCAGGCATTAGGCCATGTGCTGGGGACTCAGACCCACACATATACGCATGTCAGCATTCATG

CTTACAGGTCCGCACATGCTGGGGCAAGTGTCACACACGGGGCGCTGTAGGAAGCTGACTCTCAGCCCCT

GCAGATTTCTGCCTGCCTGGACAGGGAGGTGTTGAGAAGGCTCAGGCAGTCCTGGGCCAGGACCTTGGCC

TGGGGCTAGGGTACTGAGTGACCCTAGAATCAAGGGTGGCGTGGGCTTAAGCAGTTGCCAGACGTTCCTT
```

```
GGTACTTTGCAGGCAGACCATGTGGACCCTGGTGAGCTGGGTGGCCTTAACAGCAGGGCTGGTGGCTGGA

ACGCGGTGCCCAGATGGTCAGTTCTGCCCTGTGGCCTGCTGCCTGGACCCCGGAGGAGCCAGCTACAGCT

GCTGCCGTCCCCTTCTGGTGAGTGCCCCTCAGCCTAGGCAAGAGCTGGCAGCCTGGGTTTTCCCAAAGGG

TCATCTTGGATTGGCCAGAGGAGGACGCCAGGCACAAGTCTGTGGTTTATCATTTTCCCTGTCTTTCTAG

GACAAATGGCCCACAACACTGAGCAGGCATCTGGGTGGCCCCTGCCAGGTTGATGCCCACTGCTCTGCCG

GCCACTCCTGCATCTTTACCGTCTCAGGGACTTCCAGTTGCTGCCCCTTCCCAGAGGTGAGCGTGCCATC

AGCCCAGTGGAGGGGCTTAGGTCTGCATTTATGCTTTTCCTGCACTCTACCACCTGCAGATAAAAGGGCC

CTGCCAPTGCAGGTTTCTCTGTGTTCCACAGGCCGTGGCATGCGGGGATGGCCATCACTGCTGCCCACGG

GGCTTCCACTGCAGTGCAGACGGGCGATCCTGCTTCCAAAGATCAGGTGCAGCTGGGGTGTGGGTGCAGG

GCAGGCAGACGGGCAGCATGTGGAGTCTGGAACCCAGGAGCCCAGCTGGCGGGGGCAGCCCTGATTCCTG

CCCTTGTGCCCTCATTCATGTGGCATCTGTACTAAGCAACAGCCCTGCTGTGGACAGAGGGGCAGCACTG

GGGATAGGAGGGTGCGGGAGAAAGTGCAAGACTCCAGGTCCAGGCGTTGTGGGGGTGGGGAGAGGTCGAG

CTGGGCCGGTCTAATACCAACCCATGGTCAGTGGGTGCCCCTTCCCCATGCCATCTTGCTGAGGGAGGGA

CTGGATTGTGAGGAGGGTGAGTTAGGCCTGCCTAGGAGATCACTGAGCCTTAGTGTCACCCTCAAACCCC

AGTAGCTGGGCTTGCAGGCCCTGGTGCCACCAGCTCCTTGTGTGATGGGGGAGTCACCTTCCCTGAGTGG

GCTGGTAGTATCCTGGGTCATCTTGTCCACAGGTAACAACTCCGTGGGTGCCATCCAGTGCCCTGATAGT

CAGTTCGAATGCCCGGACTTCTCCACGTGCTGTGTTATGGTCGATGGCTCCTGGGGGTGCTGCCCCATGC

CCCAGGTACAAATCTGGGGGAGATGGGGGTATGTGGAGGGAAGTGGGGGCAGAGTTGGGGGCCAGGGGCA

GGGGGTGAAGACGGAGTCAGGACCATTTTTTCTCAGGCTTCCTGCTGTGAAGACAGGGTGCACTGCTGTC

CGCACGGTGCCTTCTGCGACCTGGTTCACACCCGCTGCATCACACCCACGGGCACCCACCCCCTGGCAAA

GAAGCTCCCTGCCCAGAGGACTAACAGGGCAGGTGAGGAGGTGGGAGAGCATCAGGCCAGGGGCTGGGGC

GGGGCCTCATTGACTCCAAGTGTAGGAAAAAGTTTCCTCCATCCTGGCTGCCCCTCACGTTTGCTCCTCT

TCCAGTGGCCTTGTCCAGCTCGGTCATGTGTCCGGACGCACGGTCCCGGTGCCCTGATGGTTCTACCTGC

TGTGAGCTGCCCAGTGGGAAGTATGGCTGCTGCCCAATGCCCAACGTGAGTGAGGGGCTGGAGCCAGCTT

GGCTGTGTGCCCCCAGCCACCTGGCCCTGACACGCACCTTACAGGGGCTCTGTGGCATGGGGCTGGCTGG

CTGCTTGCTGGGAGCCTGGCTGATGCAGGGTTCATGCTACCCCCTAGTGGGGGATTGGGGCAGTGCCAGC

CATCAGCCTGGCTGCTCCCTGTGTGCTACTGAGCCTGGAAGTGACAAAGACCCACCCCTGTCCCCACTCA

GGCCACCTGCTGCTCCGATCACCTGCACTGCTGCCCCCAAGACACTGTGTGTGACCTGATCCAGAGTAAG

TGCCTCTCCAAGGAGAACGCTACCACGGACCTCCTCACTAAGCTGCCTGCGCACACAGGTACCAGAGGCA

GGGTGCAGATACAGGGGTGGGGCCCCCTTTCCTCCCTTTTAGGCCTGGCCTTAGGATCACTGCAAGGTGG

TGTAAGCGGTACCCTCCATCTTCAACACCTGGTTCCAGCTGTGGAGCCGGCAAAGGGTTGATACCCCTGA

GGGTCCCCAGTGCCACTTCTGACCTGTCCTCTCTGCTTCCCTCACAGTGGGGGATGTGAAATGTGACATG

GAGGTGAGCTGCCCAGATGGCTATACCTGCTGCCGTCTACAGTCGGGGGCCTGGGCTGCTGCCCTTTTA

CCCAGGTACCCAGGGGTGGCGGGTGGGTGGGCTGAGCACAGTGTGGCAGGCAGCCGGGCCCCAGTGCCCA

CCTGCCCTTCTTCATCTGCCCTAGGCTGTGTGCTGTGAGGACCACATACACTGCTGTCCCGCGGGGTTTA

CGTGTGACACGCAGAAGGGTACCTGTGAACAGGGGCCCCACCAGGTGCCCTGGATGGAGAAGGCCCCAGC

TCACCTCAGCCTGCCAGACCCACAAGCCTTGAAGAGAGATGTCCCCTGTGATAATGTCAGCAGCTGTCCC

TCCTCCGATACCTGCTGCCAACTCACGTCTGGGGAGTGGGGCTGCTGTCCAATCCCAGAGGTATATGGGA

GGGGACAGCATCTTGGCCTGGGCAGGTGGGTGGCCAAGCTCCTATTGCTTTCTGCCCTCCGCATAGCCCA

TAGGTGATACCCAGCTCTGACAGATTCGTCCCCAGCTGGAGGTGCTGTAAGCAGGAGAGGCGGGCTGGAG
```

-continued

```
TAGGTAGGGGCTCGGCACTGCGCCCCACATAGTGGCTACCTACAACGCCCTTTCCTGCCCACCCCCCAGG

CTGTCTGCTGCTCGGACCACCAGCACTGCTGCCCCCAGGGCTACACGTGTGTAGCTGAGGGGCAGTGTCA

GCGAGGAAGCGAGATCGTGGCTGGACTGGAGAAGATGCCTGCCCGCCGGGCTTCCTTATCCCACCCCAGA

GACATCGGCTGTGACCAGCACACCAGCTGCCCGGTGGGGCAGACCTGCTGCCCGAGCCTGGGTGGGAGCT

GGGCCTGCTGCCAGTTGCCCCATGTGAGTGCCTCCCTGCCTGCCCCTGGATAGGGGAGCTAAGCCCAGTG

AGGGGACAGGAACATAATGCCATTCTGTGCTCCCTTCCCCGCCAGGCTGTGTGCTGCGAGGATCGCCAGC

ACTGCTGCCCGGCTGGCTACACCTGCAACGTGAAGGCTCGATCCTGCGAGAAGGAAGTGGTCTCTGCCCA

GCCTGCCACCTTCCTGGCCCGTAGCCCTCACGTGGGTGTGAAGGACGTGGAGTGTGGGGAAGGACACTTC

TGCCATGATAACCAGACCTGCTGCCGAGACAACCGACAGGGCTGGGCCTGCTGTCCCTACCGCCAGGTCA

GTGCCAACCCCCATCCTGGGGCTGGGTATGGCCAGGGACCAGGTCCCACCTCGTCCAACCCTCTCGCCCC

CCTCTGACCATCCAGGGCGTCTGTTGTGCTGATCGGCGCCACTGCTGTCCTGCTGGCTTCCGCTGCGCAG

CCAGGGGTACCAAGTGTTTGCGCAGGGAGGCCCCGCGCTGGGACGCCCCTTTGAGGGACCCAGCCTTGAG

ACAGCTGCTGTGAGGGACAGTACTGAAGACTCTGCAGCCCTCGGGACCCCACTCGGAGGGTGCCCTCTGC

TCAGGCCTCCCTAGCACCTCCCCCTAACCAAATTCTCCCTGGACCCCATTCTGAGCTCCCCATCACCATG

GGAGGTGGGGCCTCAATCTAAGGCCTTCCCTGTCAGAAGGGGGTTGTGGCAAAAGCCACATTACAAGCTG

CCATCCCCTCCCCGTTTCAGTGGACCCTGTGGCCAGGTGCTTTTCCCTATCCACAGGGGTGTTTGTGTGT

GTGCGCGTGTGCGTTTCAATAAAGTTTGTACACTTTCTTAA
```

In some embodiments, the GRN mRNA sequences includes or is derived from human GRN having the following sequence NM_002087.3 (SEQ ID No. 2):

```
ATTCTCCAATCACATGATCCCTAGAAATGGGGTGTGGGGCGAGAGGAAGCAGGGAGGAGAGTGATTTGAG

TAGAAAAGAAACACAGCATTCCAGGCTGGCCCCACCTCTATATTGATAAGTAGCCAATGGGAGCGGGTAG

CCCTGATCCCTGGCCAATGGAAACTGAGGTAGGCGGGTCATCGCGCTGGGGTCTGTAGTCTGAGCGCTAC

CCGGTTGCTGCTGCCCAAGGACCGCGGAGTCGGACGCAGGCAGACCATGTGGACCCTGGTGAGCTGGGTG

GCCTTAACAGCAGGGCTGGTGGCTGGAACGCGGTGCCCAGATGGTCAGTTCTGCCCTGTGGCCTGCTGCC

TGGACCCCGGAGGAGCCAGCTACAGCTGCTGCCGTCCCCTTCTGGACAAATGGCCCACAACACTGAGCAG

GCATCTGGGTGGCCCCTGCCAGGTTGATGCCCACTGCTCTGCCGGCCACTCCTGCATCTTTACCGTCTCA

GGGACTTCCAGTTGCTGCCCCCTTCCCAGAGGCCGTGGCATGCGGGGATGGCCATCACTGCTGCCCACGGG

GCTTCCACTGCAGTGCAGACGGGCGATCCTGCTTCCAAAGATCAGGTAACAACTCCGTGGGTGCCATCCA

GTGCCCTGATAGTCAGTTCGAATGCCCGGACTTCTCCACGTGCTGTGTTATGGTCGATGGCTCCTGGGGG

TGCTGCCCCATGCCCCAGGCTTCCTGCTGTGAAGACAGGGTGCACTGCTGTCCGCACGGTGCCTTCTGCG

ACCTGGTTCACACCCGCTGCATCACACCCACGGGCACCCACCCCCTGGCAAAGAAGCTCCCTGCCCAGAG

GACTAACAGGGCAGTGGCCTTGTCCAGCTCGGTCATGTGTCCGGACGCACGGTCCCGGTGCCCTGATGGT

TCTACCTGCTGTGAGCTGCCCAGTGGGAAGTATGGCTGCTGCCCAATGCCCAACGCCACCTGCTGCTCCG

ATCACCTGCACTGCTGCCCCCAAGACACTGTGTGTGACCTGATCCAGAGTAAGTGCCTCTCCAAGGAGAA

CGCTACCACGGACCTCCTCACTAAGCTGCCTGCGCACACAGTGGGGGATGTGAAATGTGACATGGAGGTG

AGCTGCCCAGATGGCTATACCTGCTGCCGTCTACAGTCGGGGGCCTGGGGCTGCTGCCCTTTTACCCAGG

CTGTGTGCTGTGAGGACCACATACACTGCTGTCCCGCGGGGTTTACGTGTGACACGCAGAAGGGTACCTG

TGAACAGGGGCCCCACCAGGTGCCCTGGATGGAGAAGGCCCCAGCTCACCTCAGCCTGCCAGACCCACAA

GCCTTGAAGAGAGATGTCCCCTGTGATAATGTCAGCAGCTGTCCCTCCTCCGATACCTGCTGCCAACTCA
```

```
-continued
CGTCTGGGGAGTGGGGCTGCTGTCCAATCCCAGAGGCTGTCTGCTGCTCGGACCACCAGCACTGCTGCCC

CCAGGGCTACACGTGTGTAGCTGAGGGGCAGTGTCAGCGAGGAAGCGAGATCGTGGCTGGACTGGAGAAG

ATGCCTGCCCGCCGGGCTTCCTTATCCCACCCCAGAGACATCGGCTGTGACCAGCACACCAGCTGCCCGG

TGGGGCAGACCTGCTGCCCGAGCCTGGGTGGGAGCTGGGCCTGCTGCCAGTTGCCCCATGCTGTGTGCTG

CGAGGATCGCCAGCACTGCTGCCCGGCTGGCTACACCTGCAACGTGAAGGCTCGATCCTGCGAGAAGGAA

GTGGTCTCTGCCCAGCCTGCCACCTTCCTGGCCCGTAGCCCTCACGTGGGTGTGAAGGACGTGGAGTGTG

GGGAAGGACACTTCTGCCATGATAACCAGACCTGCTGCCGAGACAACCGACAGGGCTGGGCCTGCTGTCC

CTACCGCCAGGGCGTCTGTTGTGCTGATCGGCGCCACTGCTGTCCTGCTGGCTTCCGCTGCGCAGCCAGG

GGTACCAAGTGTTTGCGCAGGGAGGCCCCGCGCTGGGACGCCCCTTTGAGGGACCCAGCCTTGAGACAGC

TGCTGTGAGGGACAGTACTGAAGACTCTGCAGCCCTCGGGACCCCACTCGGAGGGTGCCCTCTGCTCAGG

CCTCCCTAGCACCTCCCCCTAACCAAATTCTCCCTGGACCCCATTCTGAGCTCCCCATCACCATGGGAGG

TGGGGCCTCAATCTAAGGCCTTCCCTGTCAGAAGGGGGTTGTGGCAAAAGCCACATTACAAGCTGCCATC

CCCTCCCCGTTTCAGTGGACCCTGTGGCCAGGTGCTTTTCCCTATCCACAGGGGTGTTTGTGTGTGTGCG

CGTGTGCGTTTCAATAAAGTTTGTACACTTTCTT
```

In some embodiments, the progranulin polypeptide includes or is derived from human progranulin having the following amino acid sequence NP_002078.1 (SEQ ID No. 3):

```
MWTLVSWVALTAGLVAGTRCPDGQFCPVACCLDPGGASYSCCRPLLDKWPT

TLSRHLGGPCQVDAHCSAGHSCIFTVSGTSSCCPFPEAVACGDGHHCCPRG

FHCSADGRSCFQRSGNNSVGAIQCPDSQFECPDFSTCCVMVDGSWGCCPMP

QASCCEDRVHCCPHGAFCDLVHTRCITPTGTHPLAKKLPAQRTNRAVALSS

SVMCPDARSRCPDGSTCCELPSGKYGCCPMPNATCCSDHLHCCPQDTVCDL

IQSKCLSKENATTDLLTKLPAHTVGDVKCDMEVSCPDGYTCCRLQSGAWGC

CPFTQAVCCEDHTHCCPAGFTCDTQKGTCEQGPHQVPWMEKAPAHLSLPDP

QALKRDVPCDNVSSCPSSDTCCQLTSGEWGCCPIPEAVCCSDHQHCCPQGY

TCVAEGQCQRGSEIVAGLEKMPARRASLSHPRDIGCDQHTSCPVGQTCCPS

LGGSWACCQLPHAVCCEDRQHCCPAGYTCNVKARSCEKEVVSAQPATFLAR

SPHVGVKDVECGEGHFCHDNQTCCRDNRQGWACCPYRQGVCCADRRHCCPA

GFRCAARGTKCLRREAPRWDAPLRDPALRQLL
```

Progranulin serves as a precursor protein (or holoprotein) that can be cleaved into progranulin. Progranulins seem to oppose the activity of the holoprotein, at least in wound healing, inflammation and neuroprotection. Each progranulin consists of an approximately 60 amino-acid motif repeated in a tandem manner throughout the protein. Most commonly, a progranulin domain consists of 12 cysteines (two individual cysteines at the amino and carboxyl ends bookending four sets of vicinal pairs) that form six disulfide bonds. The disulfide bonds formed by cysteines confer progranulins with a stable, structurally compact, stacked β-sheet configuration that is potentially protease resistant. However, progranulin variants are found with fewer cysteines. For example, the human petite progranulin has 6 cysteines, and progranulin G has 10 cysteines.

The 88 kDa precursor protein, progranulin, is also called proepithelin and PC cell-derived growth factor. Cleavage of the signal peptide produces mature progranulin which can be further cleaved into a variety of active, 6 kDa peptides. These smaller cleavage products are named progranulin A, progranulin B, progranulin C, etc. Epithelins 1 and 2 are synonymous with progranulins A and B, respectively. Both the peptides and intact progranulin protein regulate cell growth. However, different members of the progranulin protein family may act as inhibitors, stimulators, or have dual actions on cell growth. Progranulin family members are important in normal development, wound healing, and tumorigenesis.

Methods for Modulating Gene Expression

Selective increase of the levels of specific proteins has been a therapeutic goal for almost 40 years. Substantial effort has been made using approaches such as gene therapy and antisense-mediated de-repression by targeting inhibitory antisense transcripts, with only partial success, owing to obstacles in safe delivery, immune responses or the limited number of applicable genes. Approaches that are useful for a broad range of genes are needed to safely and specifically increase the levels of endogenous proteins.

In one aspect of the disclosure, described is a method to increase the translational efficiency of specific mRNAs.

In one aspect of the disclosure, described is a method to increase the translational efficiency of specific mRNAs or progranulin.

Methods of modulating gene expression are provided, in some embodiments, that may be carried out in vitro, ex vivo, or in vivo.

Targeting the 5' Untranslated Region (5' UTR) to Increase Gene Expression of Pre-mRNA Targets In eukaryotic cells, translation is usually initiated via a cap-dependent process. The preinitiation complex binds at the 5' cap of an mRNA and scans the 5' untranslated region (UTR) for the presence of an AUG start codon. Many factors in 5' UTRs, such as structures, protein-binding sites, kozak sequence and internal ribosome entry site, can regulate translation. Recently, upstream open reading frames (uORFs) have also been shown to regulate translation efficiency of pORFs. Approximately 50% of human mRNAs have AUGs upstream of the primary AUG (pAUG), the start codon for the main protein product of the mRNA. In many cases, translation of uORFs inhibits translation from the pAUG, likely by reducing its accessibility to the preinitiation complex. Mutations in 5' UTRs can create or disrupt uORFs, thus affecting pORF translation. Many characteristics, including the numbers and lengths of uORFs, the strength of the Kozak sequence and the position of uORFs in the 5' UTR, affect the regulatory impact of uORFs (Liang X H et al., 2016).

In one embodiment, described herein is a method of treating a neurodegenerative disease or disorder, the method comprising administering to a subject in need thereof, a therapeutically effective amount of an antisense oligonucleotide (ASO) targeting a 5' untranslated region (5' UTR) region of a progranulin pre-mRNA to increase progranulin expression or activity in the brain, thereby treating the disease or disorder.

Antisense Technology for the Modulation of Gene Expression

Antisense technology is an effective means for modulating the expression of one or more specific gene products and is uniquely useful in a number of therapeutic, diagnostic, and research applications. Provided herein are antisense compounds useful for modulating gene expression via antisense mechanisms of action, including antisense mechanisms based on target occupancy. In one aspect, the antisense compounds provided herein modulate splicing of a target gene. Such modulation includes promoting or inhibiting exon inclusion. Further provided herein are antisense compounds targeted to cis splicing regulatory elements present in pre-mRNA molecules, including exonic splicing enhancers (ESEs), exonic splicing silencers (ESSs), intronic splicing enhancers (ISEs) and intronic splicing silencers (ISSs). Disruption of cis splicing regulatory elements is thought to alter splice site selection, which may lead to an alteration in the composition of splice products.

In one embodiment, the ASO targeting a 5' untranslated region (5' UTR) region of a progranulin pre-mRNA to increase progranulin expression or activity in the brain modulates the splicing of a pre-mRNA target.

Splicing

Certain aspects of the present invention also provide methods for modulating splicing of human GRN mRNA in a cell, tissue or organ using one or more of the compounds of the invention.

When the pre-mRNA has been transcribed from the DNA, it includes several introns and exons. The exons to be retained in the mRNA are determined during the splicing process. The regulation and selection of splice sites are done by trans-acting splicing activator and splicing repressor proteins as well as cis-acting elements within the pre-mRNA itself such as exonic splicing enhancers (ESEs) and exonic splicing silencers (ESSs).

Pre-mRNA splicing is an essential step in eukaryotic gene expression. Splicing-targeted antisense approaches can lead to potent modulation of disease-related gene expression, either to restore gene function by reprogramming gene splicing or to inhibit gene expression by disrupting splicing.

Newly synthesized eukaryotic mRNA molecules, also known as primary transcripts or pre-mRNA, made in the nucleus, are processed before or during transport to the cytoplasm for translation. Processing of the pre-mRNAs includes addition of a 5' methylated cap and an approximately 200-250 base poly(A) tail (SEQ ID NO: 41) to the 3' end of the transcript.

The next step in mRNA processing is splicing of the pre-mRNA, which occurs in the maturation of 90-95% of mammalian mRNAs. Introns (or intervening sequences) are regions of a primary transcript (or the DNA encoding it) that are not included in the coding sequence of the mature mRNA. Exons are regions of a primary transcript that remain in the mature mRNA when it reaches the cytoplasm. The exons are spliced together to form the mature mRNA sequence. Splice junctions are also referred to as splice sites with the 5' side of the junction often called the "5' splice site," or "splice donor site" and the 3' side the "3' splice site" or "splice acceptor site." In splicing, the 3' end of an upstream exon is joined to the 5' end of the downstream exon. Thus the unspliced RNA (or pre-mRNA) has an exon/intron junction at the 5' end of an intron and an intron/exon junction at the 3' end of an intron. After the intron is removed, the exons are contiguous at what is sometimes referred to as the exon/exon junction or boundary in the mature mRNA. Cryptic splice sites are those which are less often used but may be used when the usual splice site is blocked or unavailable. Alternative splicing, defined as the splicing together of different combinations of exons, often results in multiple mRNA transcripts from a single gene.

Processing of eukaryotic pre-mRNAs is a complex process that requires a multitude of signals and protein factors to achieve appropriate mRNA splicing. Exon definition by the spliceosome requires more than the canonical splicing signals that define intron-exon boundaries. One such additional signal is provided by cis-acting regulatory splicing enhancer and silencer sequences, such as the exonic splicing enhancers (ESEs), exonic splicing silencers (ESSs), intronic splicing enhancers (ISEs), and intron splicing silencers (ISSs) mentioned above. Certain of these regulatory sequences have been identified which either repress or enhance usage of splice donor sites or splice acceptor sites, depending on their site and mode of action (Yeo et al. 2004, Proc. Natl. Acad. Sci. U.S.A. 101(44):15700-15705). Further, binding of specific proteins (e.g., trans factors) to these regulatory sequences directs the splicing process, by promoting or inhibiting usage of particular splice sites, and thus modulates the ratio of splicing products (Scamborova et al. 2004, Mol. Cell. Biol. 24(5): 1855-1869; Hovhannisyan and Carstens, 2005, Mol. Cell. Biol. 25(1):250-263; Minovitsky et al. 2005, Nucleic Acids Res. 33(2):714-724).

In one aspect of the disclosure, ASOs complementary to Progranulin are provided for modulating expression of Progranulin in a cell. In some embodiments, expression of Progranulin is upregulated or increased.

In one aspect of the disclosure, described is a method of treating a neurodegenerative disease or disorder, the method comprising administering to a subject in need thereof, a therapeutically effective amount of an antisense oligonucleotide (ASO) targeting an intron of a Progranulin (GRN) mRNA to increase GRN expression or activity in the brain, thereby treating the disease or disorder.

As described herein, antisense oligonucleotides (ASOs) are 15-25 nt DNA sequences designed to bind complementary RNA targets. ASOs can be used to knock down genes (e.g. including but not limited to knockdown using a chimeric antisense oligonucleotides (gapmers) that contain a central block of deoxynucleotide monomers sufficiently long to induce RNase H cleavage). ASOs can also act as a simple steric-blocker (e.g. when ASOs are fully modified throughout the length; and therefore they do not activate RNaseH including but not limited to splice-switching ASOs). ASO technology provided the first oligonucleotide-based approach to disrupting gene expression and has been used in knockdown experiments, target validation, drug therapy, and other applications. More recently, ASOs are used to study the role of long noncoding RNAs (lncRNAs) in gene regulation.

Antisense oligonucleotides (ASOs) have been used successfully to induce sustained gene upregulation in neuronal tissues by modulation of mRNA splicing toward a productive isoform. Nusinersen/Spinraza, an ASO drug that boosts the expression of SMN2 and thereby compensates for the deficiency of SMN proteins in spinal muscular atrophy. With overwhelming evidence of efficacy with very little adverse effect, it was approved by the FDA in 2016 and essentially cured spinal muscular atrophy, a previously uniformly lethal disease (Finkel et al., 2017; Mercuri et al., 2018). Moreover, recent non-human primate studies and clinical trials for Huntington's disease showed efficient delivery of ASOs deep into brain parenchyma (Kordasiewicz et al., 2012; van Roon-Mom et al., 2018). Antisense compounds have also been used to alter the ratio of the long and short forms of Bcl-x pre-mRNA (U.S. Pat. Nos. 6,172,216; 6,214,986; Taylor et al., Nat. Biotechnol. 1999, 17, 1097-1100) or to force skipping of specific exons containing premature termination codons (Wilton et al., Neuromuscul. Disord., 1999, 9, 330-338). U.S. Pat. No. 5,627,274 and WO 94/26887 disclose compositions and methods for combating aberrant splicing in a pre-mRNA molecule containing a mutation using antisense oligonucleotides which do not activate RNAse H.

In some embodiments, aspects of the present invention are based on principles of antisense technology by providing antisense oligonucleotides as the oligomeric compounds to modulate the expression of one or more specific gene products. The antisense compounds described herein may be useful for modulating gene expression via antisense mechanisms of action, including antisense mechanisms based on target occupancy. In one aspect, the antisense compounds provided herein modulate splicing of a target gene to promote exon inclusion, e.g., in certain embodiments an unproductive isoform of human GRN that is specifically expressed in brain tissues and retains intron 4, which leads to rapid nonsense-mediated decay of the transcripts. This may be accomplished via the pairing (e.g., hybridization) of complementary strands of antisense compounds to their target sequence. An antisense compound is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In some embodiments, described herein is an ASO therapy that reduces the intron retention. Further analyses revealed splice silencing elements in/near the intron that, when targeted by ASOs, can improve splicing of the intron and thereby induce upregulation of GRN to a therapeutically relevant level.

Antisense Oligonucleotides (ASOs)

Antisense oligonucleotides (ASOs) or antisense RNA can complementarily bind to a target site in pre-mRNA and regulate gene splicing, either to restore gene function by reprogramming gene splicing or to inhibit gene expression by disrupting splicing.

Antisense oligonucleotides (ASOs) have been used successfully to induce sustained gene upregulation in neuronal tissues by modulation of mRNA splicing toward a productive isoform. Nusinersen/Spinraza, an ASO drug that boosts the expression of SMN2 and thereby compensates for the deficiency of SMN proteins in spinal muscular atrophy. With overwhelming evidence of efficacy with very little adverse effect, it was approved by the FDA in 2016 and essentially cured spinal muscular atrophy, a previously uniformly lethal disease (Finkel et al., 2017; Mercuri et al., 2018). Moreover, recent non-human primate studies and clinical trials for Huntington's disease showed efficient delivery of ASOs deep into brain parenchyma (Kordasiewicz et al., 2012; van Roon-Mom et al., 2018). Antisense compounds have also been used to alter the ratio of the long and short forms of Bcl-x pre-mRNA (U.S. Pat. Nos. 6,172,216; 6,214,986; Taylor et al., Nat. Biotechnol. 1999, 17, 1097-1100) or to force skipping of specific exons containing premature termination codons (Wilton et al., Neuromuscul. Disord., 1999, 9, 330-338). U.S. Pat. No. 5,627,274 and WO 94/26887 disclose compositions and methods for combating aberrant splicing in a pre-mRNA molecule containing a mutation using antisense oligonucleotides which do not activate RNAse H.

In some embodiments, aspects of the present invention are based on principles of antisense technology by providing antisense oligonucleotides as the oligomeric compounds to modulate the expression of one or more specific gene products. The antisense compounds described herein may be useful for modulating gene expression via antisense mechanisms of action, including antisense mechanisms based on target occupancy. In one aspect, the antisense compounds provided herein modulate the suppression of non-productive isoforms. This may be accomplished via the pairing (e.g., hybridization) of complementary strands of antisense compounds to their target sequence. An antisense compound is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In some embodiments, any one or more thymidine (T) nucleotides (or modified nucleotide thereof) or uridine (U) nucleotides (or a modified nucleotide thereof) in a sequence provided herein, including a sequence provided in the sequence listing, may be replaced with any other nucleotide suitable for base pairing (e.g., via a Watson-Crick base pair) with an adenosine nucleotide. In some embodiments, any one or more thymidine (T) nucleotides (or modified nucleotide thereof) or uridine (U) nucleotides (or a modified nucleotide thereof) in a sequence provided herein, including a sequence provided in the sequence listing, may be suitably replaced with a different pyrimidine nucleotide or vice versa. In some embodiments, any one or more thymidine (T) nucleotides (or modified nucleotide thereof) in a sequence provided herein, including a sequence provided in the sequence listing, may be suitably replaced with a uridine (U) nucleotide (or a modified nucleotide thereof) or vice versa. In some embodiments, GC content of the single stranded oligonucleotide is preferably between about 30-60%. Contiguous runs of three or more Gs or Cs may not be preferable in some embodiments. Accordingly, in some embodiments, the oligonucleotide does not comprise a stretch of three or more guanosine nucleotides.

Multiple human genetic diseases resulting from a point mutation are caused by aberrant splicing. Such point mutations can either disrupt a current splice site or create a new splice site, resulting in mRNA transcripts comprised of a different combination of exons or with deletions in exons. Point mutations also can result in activation of a cryptic splice site or disrupt regulatory cis elements (i.e. splicing enhancers or silencers) (Cartegni et al., Nat. Rev. Genet., 2002, 3, 285-298; Drawczak et al., Hum. Genet., 1992, 90, 41-54).

In some embodiments, described herein are methods for the antisense-mediated splicing modulation.

In some embodiments, the ASO targeting progranulin modulates the splicing of a pre-mRNA target.

In some embodiments, described herein is an unproductive isoform of human GRN.

In some embodiments, described herein is an unproductive isoform of human GRN that is specifically expressed in brain tissues.

In some embodiments, the progranulin (GRN) expression or activity in the brain is modulated by regulating nuclear export of a pre-mRNA target.

In some embodiments, the progranulin (GRN) expression or activity in the brain target is regulating stability of the pre-mRNA target.

In another embodiment, the ASO targets an intron-exon or exon-intron junction.

In another embodiment, the modulation of splicing comprises direct binding of an ASO within 50 nucleobases upstream or downstream of an intron-exon or exon-intron junction, thereby causing a decreased frequency of use of the 5' or 3' splice site region of a selected pre-mRNA target.

In another embodiment, the ASO targets at least a portion of a region up to 50 nucleobases upstream or downstream from a 5' or 3' splice site.

In another embodiment, the ASO targets a splicing enhancer or silencer element.

In another embodiment, the modulation of splicing comprises a preferential inclusion of a segment of the pre-mRNA into a mature mRNA through inclusion of an alternative exon, extension of an exon at either 5' or 3' end, or retention of an intron.

In another embodiment, the modulation of splicing comprises a preferential exclusion of a segment of the pre-mRNA from a mature mRNA through exclusion of an alternative exon, truncation of an exon at either 5' or 3' end, or enhanced splicing of an intron.

In another embodiment, the modulation of splicing comprises the direct binding of an ASO at a splicing enhancer or silencer element, thereby causing a decreased effect of the splicing enhancer or silencer element in a selected pre-mRNA target.

In another embodiment, ASOs or antisense RNA can complementarily bind to a target site in pre-mRNA, and regulate the splicing process, including but not limited to 2'-O-Methyl (2'-O-Me) and 2'-O-methoxyethyl (2'MOE) phosphorothioate oligomers.

In another embodiment, described herein are ASOs with chemical modifications of the furanose ring of the nucleotide, to further enhance target affinity, biostability and pharmacokinetics.

In another embodiment, phosphoroamidate morpholino oligomer (PMO); (ii) peptide nucleic acid (PNA); and/or (iii) locked nucleic acid (LNA) could be used targeting the 5' UTR of progranulin.

In one aspect of the disclosure, ASOs complementary to progranulin are provided for modulating expression of progranulin in a cell. In some embodiments, expression of progranulin is upregulated or increased.

In one aspect of the disclosure, an ASO comprising an oligonucleotide of 12 to 40 linked nucleotides or modified nucleotides in length is provided, wherein the ASO comprises a nucleobase sequence with homology to a 5' untranslated region (5' UTR) of a progranulin (GRN) and wherein the ASO increases GRN expression or activity in the brain.

In one aspect of the disclosure, ASOs targeting upstream Open Reading Frames (uORFs) regions of progranulin can sequence-specifically increase protein levels both in vitro and in vivo. As uORFs are present in a large number of mRNAs, ASO-based agents can thus be used to specifically increase endogenous protein production for many genes. As many diseases result from decreased protein levels, this approach may find application in biological research and in the clinic, as ASOs have been well-developed for efficient and safe delivery.

In one aspect of the disclosure, described is a method of treating a neurodegenerative disease or disorder, the method comprising administering to a subject in need thereof, a therapeutically effective amount of an antisense oligonucleotide (ASO) targeting a 5' untranslated region (5' UTR) region of a progranulin mRNA.

In some embodiments, described is a method of treating a neurodegenerative disease or disorder, the method comprising administering to a subject in need thereof, a therapeutically effective amount of an antisense oligonucleotide (ASO) targeting a 5' untranslated region (5' UTR) region of a progranulin pre-mRNA which results in modulation of splicing of the selected progranulin pre-mRNA and an increase in progranulin expression or activity in the brain, thereby treating the disease or disorder.

TABLE 1

Table listing the control ASO sequence (SEQ ID No. 4) and ASO sequences that are complementary to progranulin (SEQ ID Nos. 5-18 and SEQ ID Nos. 27-39). ASO sequences contain a full phosphorothioate backbone and full 2'MOE modifications.

| ASO ID | Sequence (5' to 3') |
| --- | --- |
| S01 | GCATGAGCGGGCCCTGAA (SEQ ID No. 4) |
| S02 | GCGAGAGGTCTGCGCGGCCG (SEQ ID No. 5) |
| S03 | AGCAGGCGAGAGGTCTGCGC (SEQ ID No. 6) |
| S04 | GCAGGAGCAGGCGAGAGGTC (SEQ ID No. 7) |
| S05 | CTCCGGCTGAGACTCCAGGG (SEQ ID No. 8) |
| S06 | GTCTCCGGCTGAGACTCCAG (SEQ ID No. 9) |
| S07 | TCTTCTGTTGTCTCCGGCTG (SEQ ID No. 10) |
| S08 | GTAAGCGGTTCTTCTGTTGT (SEQ ID No. 11) |
| S09 | AGTTTCAGTAAGCGGTTCTT (SEQ ID No. 12) |
| S10 | CGACAGGGGTGGAGCTGGGT (SEQ ID No. 13) |
| S11 | CTACCGACAGGGGTGGAGCT (SEQ ID No. 14) |
| S12 | GCACCTACCGACAGGGGTGG (SEQ ID No. 15) |

TABLE 1-continued

Table listing the control ASO sequence
(SEQ ID No. 4) and ASO sequences
that are complementary to progranulin
(SEQ ID Nos. 5-18 and SEQ ID Nos. 27-39).
ASO sequences contain a full
phosphorothioate backbone and
full 2'MOE modifications.

| ASO ID | Sequence (5' to 3') |
|--------|---------------------|
| S13 | GCCAGCACCTACCGACAGGG (SEQ ID No. 16) |
| S14 | AGAAGCCAGCACCTACCGAC (SEQ ID No. 17) |
| S15 | GGGAAGAAGCCAGCACCTAC (SEQ ID No. 18) |
| S28 | CCTGCACCCACACCCCA (SEQ ID NO. 27) |
| S29 | CCTGCCCTGCACCCACA (SEQ ID NO. 28) |
| S30 | GTCTGCCTGCCCTGCAC (SEQ ID NO. 29) |
| S31 | TGCCCGTCTGCCTGCCC (SEQ ID NO. 30) |
| S32 | ACATGCTGCCCGTCTGCC (SEQ ID NO. 31) |
| S33 | ACTCCACATGCTGCCCGT (SEQ ID NO. 32) |
| S34 | TTCCAGACTCCACATGCTG (SEQ ID NO. 33) |
| S35 | CTGGGTTCCAGACTCCACA (SEQ ID NO. 34) |
| S36 | GCTCCTGGGTTCCAGACT (SEQ ID NO. 35) |
| S37 | CTGGGCTCCTGGGTTCC (SEQ ID NO. 36) |
| S38 | GCCAGCTGGGCTCCTGG (SEQ ID NO. 37) |
| S39 | CCCCGCCAGCTGGGCT (SEQ ID NO. 38) |
| S40 | GCTGCCCCGCCAGCT (SEQ ID NO. 39) |

C = 5-methylcytidine.
T = methyluridine.

In some embodiments, described herein is a method wherein the ASO comprises an oligonucleotide of 12 to 40 linked nucleotides in length, which oligonucleotides comprise a sequence: a. at least 8000 homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ TD No. 13, SEQ TD No. 14, SEQ TD No. 15, SEQ TD No. 16, SEQ TD No. 17, SEQ TD No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ TD No. 36, SEQ ID No. 37, SEQ ID No. 38, and/or SEQ ID No. 39; and b. wherein the oligonucleotide comprises at least one modified nucleotide.

In some embodiments, described herein is a method wherein the ASO comprises an oligonucleotide of 12 to 40 linked nucleotides in length, which oligonucleotides comprise a sequence: a. at least 90% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

In some embodiments, described herein is a method wherein the ASO comprises an oligonucleotide of 12 to 40 linked nucleotides in length, which oligonucleotides comprise a sequence: a. at least 100% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

In some embodiments, the ASO is 7, 8, 9, 10, 11, 12, 13, 14, 15, 16, 17, 18, 19, 20 or more nucleotides in length. In some embodiments, the ASO is 8 to 20, 8 to 19, 8 to 18, 8 to 17, 8 to 16, 8 to 15, 9 to 20, 9 to 19, 9 to 18, 9 to 17, 9 to 16, 9 to 15, 10 to 20, 10 to 19, 10 to 18, 10 to 17, 10 to 16, or 10 to 15 nucleotides in length. In a preferred embodiment, the ASO is 8 to 15 nucleotides in length.

In some embodiments, ASOs disclosed herein may increase expression of mRNA corresponding to the gene by at least about 2%, by at least 2.5%, by at least about 5%, by at least about 10%, by at least about 20% by at least about 30%, by at least about 40%, by at least about 50%, by at least about 60% by at least about 70%, by at least about 80%, by at least about 90% by at least about 100% or by about 2 fold to about 80 fold. In some embodiments, expression may be increased by at least about 5 fold, by at least 10 fold, by at least 15 fold, by at least 20 fold, by at least 30 fold, by at least 40 fold, by at least 50 fold, by at least 60 fold, by at least 70 fold, by at least 80 fold, by at least 90 fold or 100 fold, or any range between any of the foregoing numbers. It has also been found that increased mRNA expression has been shown to correlate to increased protein levels.

As described herein, antisense oligonucleotides (ASOs) are 15-25 nt DNA sequences designed to bind complementary RNA targets. ASOs can be used to knock down genes (e.g. including but not limited to knockdown using a chimeric antisense oligonucleotides (gapmers) that contain a central block of deoxynucleotide monomers sufficiently long to induce RNase H cleavage). ASOs can also act as a simple steric-blocker (e.g. when ASOs are fully modified throughout the length; and therefore they do not activate RNase H including but not limited to splice-switching ASOs). ASO technology provided the first oligonucleotide-based approach to disrupting gene expression and has been used in knockdown experiments, target validation, drug therapy, and other applications. More recently, ASOs are used to study the role of long noncoding RNAs (lncRNAs) in gene regulation.

In some embodiments, the ASO specifically binds to, or is complementary to an RNA that is encoded in a genome (e.g., a human genome) as a single contiguous transcript (e.g., a non-spliced RNA).

In some embodiments, the ASO comprises an oligonucleotide of 12 to 40 linked nucleotides in length, which oligonucleotides comprise at least one modified nucleotide which comprises a modified sugar moiety.

In some embodiments, the ASO comprises a 2' modification of its sugar moiety.

In some embodiments, the ASO comprises a 2'-O-methyl, 2'-O-methoxyethyl, 2'-dimethylaminooxyethoxy, 2'-dimethylaminoethoxyethoxy, 2'-fluoro or 2'-acetamide modification on every sugar moiety.

In some embodiments, the ASO comprises a LNA nucleobase.

In some embodiments, the ASO comprises at least one modified linkage.

In some embodiments, the linkage of the ASO comprises a phosphodiester, phosphotriester, or phosphorothioate backbone linkage.

In some embodiments, the ASO is a morpholino or peptide nucleic acid.

In some embodiments, the ASO comprises at least one modified base which increases binding affinity for the pre-mRNA target, which increases nuclease resistance of the antisense compound, or which decrease immune-stimulation.

In some embodiments, the modified base is methyl-C.

In some embodiments, the ASO is a mixture of one or more stereopure molecules with a defined sequence.

Nuclear Import

In some embodiments, described herein is a 5' UTR-extended form of a GRN transcript that is depleted in the cytosol compared to nuclei.

In some embodiments, described herein is 5' UTR-extended form of GRN transcript that is inefficiently exported out of nuclei.

The entry and exit of large molecules from the cell nucleus is tightly controlled by the nuclear pore complexes (NPCs). Although small molecules can enter the nucleus without regulation, macromolecules such as RNA and proteins require association with transport factors known as nuclear transport receptors, like karyopherins called importins to enter the nucleus and exportins to exit.

Importin proteins bind their cargo in the cytoplasm, after which they are able to interact with the nuclear pore complex and pass through its channel. Once inside the nucleus, interaction with Ran-GTP causes a conformational change in the importin that causes it to dissociate from its cargo. The resulting complex of importin and Ran-GTP then translocates to the cytoplasm, where a protein called Ran Binding Protein (RanBP) separates Ran-GTP from importin. Separation allows access to a GTPase activating protein (GAP) that binds Ran-GTP and induces the hydrolysis of GTP to GDP. The Ran-GDP produced from this process now binds the nuclear transport factor NUTF2 which returns it to the nucleoplasm. Now in the nucleus, the Ran-GDP interacts with a guanine nucleotide exchange factor (GEF) which replaces the GDP with GTP, resulting again in Ran-GTP, and beginning the cycle anew.

Nuclear Export

Nuclear export roughly reverses the import process; in the nucleus, the exportin binds the cargo and Ran-GTP and diffuses through the pore to the cytoplasm, where the complex dissociates. Ran-GTP binds GAP and hydrolyzes GTP, and the resulting Ran-GDP complex is restored to the nucleus where it exchanges its bound ligand for GTP. Hence, whereas importins depend on RanGTP to dissociate from their cargo, exportins require RanGTP in order to bind to their cargo.

A specialized mRNA exporter protein moves mature mRNA to the cytoplasm after post-transcriptional modification is complete. This translocation process is actively dependent on the Ran protein, although the specific mechanism is not yet well understood. Some particularly commonly transcribed genes are physically located near nuclear pores to facilitate the translocation process.

TRNA export is also dependent on the various modifications it undergoes, thus preventing export of improperly functioning tRNA. This quality control mechanism is important due to tRNA's central role in translation, where it is involved in adding amino acids to a growing peptide chain. The tRNA exporter in vertebrates is called exportin-t. Exportin-t binds directly to its tRNA cargo in the nucleus, a process promoted by the presence of RanGTP. Mutations that affect tRNA's structure inhibit its ability to bind to exportin-t, and consequentially, to be exported, providing the cell with another quality control step. As described above, once the complex has crossed the envelope it dissociates and releases the tRNA cargo into the cytosol.

The transport of RNA molecules from the nucleus to the cytoplasm is fundamental for gene expression. The different RNA species that are produced in the nucleus are exported through the nuclear pore complexes via mobile export receptors. Small RNAs (such as tRNAs and microRNAs) follow relatively simple export routes by binding directly to export receptors. Large RNAs (such as ribosomal RNAs and mRNAs) assemble into complicated ribonucleoprotein (RNP) particles and recruit their exporters via class-specific adaptor proteins. Export of mRNAs is unique as it is extensively coupled to transcription (in yeast) and splicing (in metazoa).

In some embodiments, described are methods that modulate progranulin (GRN) expression or activity in the brain is by regulating nuclear export of a pre-mRNA target.

In some embodiments, the progranulin (GRN) expression or activity in the brain target is regulating stability of the pre-mRNA target.

In one aspect of any of the embodiments, described herein is a pharmaceutical composition comprising an ASO homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and a pharmaceutically acceptable carrier for use in a method of treating a neurodegenerative disease or disorder.

Therapeutic Activity

In some embodiments the pharmaceutical composition described herein has a therapeutic activity. Antisense compounds of the invention can be used to modulate the expression of GRN in an animal, such as a human. In one embodiment, the methods comprise the step of administering to a subject in need of therapy for a disease or condition associated with GRN an effective amount of an antisense compound that modulates expression of GRN (e.g. modulates splicing of GRN). A disease or condition associated with GRN includes, but is not limited to, Alzheimer's disease, frontotemporal dementia and Parkinson's disease.

In one embodiment, the antisense compounds of the present invention effectively suppress the production of inefficiently translated of human GRN, resulting in increasing the level of functional GRN mRNA. Antisense compounds of the present invention that effectively modulate expression of human GRN RNA or protein products of expression are considered active antisense compounds.

Dosage, Administration, Efficacy of ASOs

Dosage

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions, methods, and uses that exhibit large therapeutic indices are preferred. A therapeutically effective dose can be estimated initially from cell culture assays. Also, a dose can be formulated in animal models to achieve a circulating plasma concentration range that includes the IC50, which achieves a half-maximal inhibition of measured function or activity as determined in cell culture, or in an appropriate animal model. The effects of any particular dosage can be monitored by a suitable bioassay. The dosage can be determined by a physician and adjusted, as necessary, to suit observed effects of the treatment.

Administration

The agents described herein can be administered to a subject in need thereof by any appropriate route which results in an effective treatment in the subject.

Exemplary modes of administration of the ASOs for the modulation of progranulin expression or activity in the brain by the ASO and/or ASOs disclosed herein include oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular (including administration to skeletal, diaphragm and/or cardiac muscle), intrapleural, intracerebral, and intraarticular), topical (e.g., to both skin and mucosal surfaces, including airway surfaces, and transdermal administration), intralymphatic, and the like, as well as direct tissue or organ injection (e.g., to liver, eye, skeletal muscle, cardiac muscle, diaphragm muscle or brain).

In some embodiments, the pharmaceutical compositions can conveniently be presented in unit dosage form. A unit dosage form will typically be adapted to one or more specific routes of administration of the pharmaceutical composition. In some embodiments, the unit dosage form is adapted for administration by inhalation. In some embodiments, the unit dosage form is adapted for administration by a vaporizer. In some embodiments, the unit dosage form is adapted for administration by a nebulizer. In some embodiments, the unit dosage form is adapted for administration by an aerosolizer. In some embodiments, the unit dosage form is adapted for oral administration, for buccal administration, or for sublingual administration. In some embodiments, the unit dosage form is adapted for intravenous, intramuscular, or subcutaneous administration. In some embodiments, the unit dosage form is adapted for intrathecal or intracerebroventricular administration. In some embodiments, the pharmaceutical composition is formulated for topical administration. The amount of active ingredient which can be combined with a carrier material to produce a single dosage form will generally be that amount of the compound which produces a therapeutic effect.

Liquid dosage forms include solutions, suspensions and emulsions. Liquid form preparations may be administered by intravenous, intracerebral, intraperitoneal, parenteral or intramuscular injection or infusion. Sterile injectable formulations may comprise a sterile solution or suspension of the active agent in a non-toxic, pharmaceutically acceptable diluent or solvent. Suitable diluents and solvents include sterile water, Ringer's solution and isotonic sodium chloride solution, etc. Liquid dosage forms also include solutions or sprays for intranasal administration.

Aerosol preparations suitable for inhalation may include solutions and solids in powder form, which may be combined with a pharmaceutically acceptable carrier, such as an inert compressed gas. Use of a long-term sustained release implant may be particularly suitable for treatment of chronic conditions such as Alzheimer's disease. Long-term release, are used herein, means that the implant is constructed and arranged to delivery therapeutic levels of the active ingredient for at least 5 days, for at least 10 days, for at least 15 days, for at least 20 days, for at least 30 days, for at least 40 days, for at least 50 days or for at least 60 days. Long-term sustained release implants are well-known to those of ordinary skill in the art and include some of the release systems described above.

Administration of the ASOs for the modulation of expression of GRN can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye.

Pharmaceutical preparations may be conveniently prepared in unit dosage form, according to standard procedures of pharmaceutical formulation. The quantity of active compound per unit dose may be varied according to the nature of the active compound and the intended dosage regime.

Other delivery systems can include time-release, delayed release or sustained release delivery systems. Such systems can avoid repeated administrations of the therapeutic agents of the invention described herein, increasing convenience to the subject and the physician. Many types of release delivery systems are available and known to those of ordinary skill in the art. They include polymer based systems such as poly (lactide-glycolide), copolyoxalates, polycapro-lactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the therapeutic agent(s) of the invention are contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The most suitable route in any given case will depend on the nature and severity of the condition being treated, ameliorated, and/or prevented and on the nature of the particular ASOs that is being used. Additionally, ASOs permits one to administer more than one ASO e.g. multiple ASO (e.g. a ASO cocktail including but not limited to ASOs of the following sequences: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39.

The pharmaceutical composition is preferably administered in an amount effective to modulate the expression of GRN by at least 1%, by at least 3%, by at least 5%, by at least 10%, by at least 15%, by at least 20%, by at least 30%, by at least 40%, by at least 50%, by at least 60%, by at least 70%, by at least 80%, by at least 90% or by 100%. It is preferred that the amount administered is an amount effective to maximize the modulation of the expression of GRN while minimizing toxicity.

Advantageously, the time of administration can be coupled with other treatment methodologies. The above agents may also be used in combination in order to achieve the desired therapeutic effect. Certain combinations of agents may act co-operatively, additively or synergistically, when co-administered or when administered sequentially. The antisense treatment may be applied before, after, or in combination with other treatments e.g. for Alzheimer's disease treatments include but are not limited to cholinesterase inhibitor and/or Memantine; for Parkinson's disease treatments include but are not limited to Carbidopa-levodopa, Dopamine agonists, Dopamine agonists, Catechol O-methyltransferase (COMT) inhibitors, Anticholinergics and/or Amantadine.

In neurodegenerative diseases or disorders, e.g. Alzheimer's disease (AD) it is envisaged that treatment will be administered continuously over a long period of time to prevent or slow the development of AD-type pathology in the brain. Oral dosage forms are particularly preferred for long term therapy and prophylactic treatment because of convenience for the patient.

In some embodiments, Cell-penetration peptides (CPPs) can be used as a transmembrane drug delivery agent for improved delivery of ASOs targeting a 5' untranslated region of progranulin. CPPs are a class of small cationic peptides of at least 10, or at least 11, or at least 12, or at least 13, or at least 14, or at least 15, or at least 15, or at least 20, or at least 25, or at least 30 amino acids that can be used as transmembrane drug delivery agents through various forms of endocytosis for low-molecular weight compounds, including drugs, imaging agents, oligonucleotides, peptides and proteins. CPPs are also known as 'protein transduction domains'. CPPs include but are not limited to the peptides Tat or penetratin.

In some embodiments, arginine-rich CPPs can be used for improved delivery of ASOs targeting progranulin to the brain, e.g. Pep-3, for in vivo delivery.

In some embodiments, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No.

39 can be fused to Pep-3 to allow the transvascular delivery of the ASOs to specifically to target neuronal cells.

In some embodiments, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39 can be fused to Tat to allow the transvascular delivery of the ASOs to specifically to target neuronal cells.

In some embodiments, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39 can be fused to penetratin to allow the transvascular delivery of the ASOs to specifically to target neuronal cells.

In some embodiments, RVG-9R, a short peptide derived from rabies virus glycoprotein (RVG) to a nine arginine siRNA packaging peptide (RVG-9R) can be used for delivery of ASOs targeting progranulin to the brain. RVG-9R enables the transvascular delivery of nucleotides acids e.g. siRNA specifically to target neuronal cells expressing the nicotinic ACh receptor (nAChR) in the brain e.g. intravenous treatment with RVG-9R-bound siRNA against flavivirus induces robust protection against fatal viral encephalitis in mice, thereby allowing the systemic delivery of macro-molecular oligonucleotides can traverse the blood-brain barrier and specifically target the brain of adult mice.

In some embodiments, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39 can be fused to RVG-9R to allow the transvascular delivery of the ASOs to specifically to target neuronal cells In some embodiments, the ASOs targeting progranulin can be used in both veterinary and medical applications. Suitable subjects for ex vivo gene delivery methods as described above include both avians (e.g., chickens, ducks, geese, quail, turkeys and pheasants) and mammals (e.g., humans, bovines, ovines, caprines, equines, felines, canines, and lagomorphs), with mammals being preferred. Human subjects are most preferred. Human subjects include neonates, infants, juveniles, and adults.

Efficacy

The efficacy of a composition in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved or ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example animal models of cancer, e.g. a murine xenograft model. When using an experimental animal model, efficacy of treatment is evidenced when a statistically significant change in a marker is observed.

In vitro and animal model assays are provided herein which allow the assessment of a given dose of a composition. The efficacy of a given dosage combination can also be assessed in an animal model, e.g. a murine xenograft model.

In vitro and animal model assays are provided herein which allow the assessment of a given dose of a composition. The efficacy of a given dosage combination can also be assessed in D/an animal model, e.g. a murine Alzheimer's disease model including but not limited to an APP/PS1 double transgenic mouse model expressing a chimeric mouse/human amyloid precursor protein (Mo/HuAPP695swe) and a mutant human presenilin 1 (PS1-dE9), both directed to CNS neurons.

The efficacy of an agent described herein, e.g., for the treatment of a neurodegenerative disease or disorder including but not limited to Alzheimer's disease, frontotemporal dementia and Parkinson's disease, can be determined by the skilled practitioner. However, a treatment is considered "effective treatment," as the term is used herein, if one or more of the signs or symptoms of a neurodegenerative disease or disorder are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g., increased GRN levels and/or Amyloid 3 levels in the brain. Efficacy can also be measured by a failure of an individual to worsen as assessed by hospitalization, or need for medical interventions (i.e., progression of the symptoms).

Assays well known in the art can be used to test the efficiency of modulation of progranulin expression or activity in the brain by the ASO and/or ASOs described herein can be performed in both in vitro and in vivo models. The efficiency of modulation of progranulin expression or activity in the brain by the ASO and/or ASOs described herein can be assessed by one skilled in the art by measuring mRNA and protein levels of the desired transgene (e.g., reverse transcription PCR, western blot analysis, and enzyme-linked immunosorbent assay (ELISA).

Efficacy can be assessed in animal models of a condition described herein, for example, a mouse model or an appropriate animal model of neurodegenerative disease or disorder, as the case may be. When using an experimental animal model, efficacy of treatment is evidenced when a statistically significant change in a marker is observed, e.g. increased GRN levels and/or Amyloid-$\beta$ levels in the brain.

It is contemplated herein that the effects of modulation of progranulin expression or activity in the brain by the ASO and/or ASOs in a cell or subject can last for at least 1 month, at least 2 months, at least 3 months, at least four months, at least 5 months, at least six months, at least 10 months, at least 12 months, at least 18 months, at least 2 years, at least 5 years, at least 10 years, at least 20 years, or can be permanent.

In some embodiments, an ASO described herein can be codon optimized for the host cell. As used herein, the term "codon optimized" or "codon optimization" refers to the process of modifying a nucleic acid sequence for enhanced expression in the cells of the vertebrate of interest, e.g., mouse or human (e.g., humanized), by replacing at least one, more than one, or a significant number of codons of the native sequence (e.g., a prokaryotic sequence) with codons that are more frequently or most frequently used in the genes of that vertebrate. Various species exhibit particular bias for certain codons of a particular amino acid. Typically, codon optimization does not alter the amino acid sequence of the original translated protein. Optimized codons can be determined using e.g., Aptagen's Gene Forge® codon optimization and custom gene synthesis platform (Aptagen, Inc.) or another publicly available database.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating a neurodegenerative disease or disorder, the method comprising administering to a subject in need thereof, a therapeutically effective amount of an antisense oligonucleotide (ASO) targeting an intron of a Progranulin (GRN) mRNA to increase GRN expression or activity in the brain, thereby treating the disease or disorder.

2. The method of paragraph 1, wherein the ASO comprises an oligonucleotide of 12 to 40 linked nucleotides in length, which oligonucleotides comprise a sequence:
    a. at least 80% homolog to a nucleotide sequence that is selected from the group consisting of: SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and
    b. wherein the oligonucleotide comprises at least one modified nucleotide.

3. The method of paragraph 1, wherein the ASO comprises an oligonucleotide of 12 to 40 linked nucleotides in length, which oligonucleotides comprise a sequence:
    a. at least 90% homolog to a nucleotide sequence that is selected from the group consisting of: SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and
    b. wherein the oligonucleotide comprises at least one modified nucleotide.

4. The method of paragraph 1, wherein the ASO comprises an oligonucleotide of 12 to 40 linked nucleotides in length, which oligonucleotides comprise a sequence:
    a. at least 100% homolog to a nucleotide sequence that is selected from the group consisting of: SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and
    b. wherein the oligonucleotide comprises at least one modified nucleotide.

5. The method of any of paragraphs 1-4, wherein the disease or disorder is selected from Alzheimer's disease, Frontotemporal Dementia, Batten disease and Parkinson's disease.

6. The method of any of paragraphs 1-4, wherein said progranulin (GRN) expression or activity in the brain is modulated by splicing of a pre-mRNA target.

7. The method of any of paragraphs 1-6, wherein the ASO comprises an oligonucleotide of 12 to 40 linked nucleotides in length, which oligonucleotides comprise at least one modified nucleotide which comprises a modified sugar moiety.

8. The method of any of paragraphs 1-7, wherein the ASO comprises a 2' modification of its sugar moiety.

9. The method of any of paragraphs 1-8, wherein the ASO comprises a 2'-o-methyl, 2'-methoxyethoxy, 2'-dimethylaminooxyethoxy, 2'-dimethylaminoethoxyethoxy, 2'-fluoro or 2'-acetamide modification on every sugar moiety.

10. The method of any of paragraphs 1-9, wherein the ASO comprises a LNA nucleobase.

11. The method of any of paragraphs 1-10, wherein the ASO comprises at least one modified linkage.

12. The method of any of paragraphs 1-11, wherein the linkage of the ASO comprises a phosphodiester, phosphotrester, or phosphorothioate backbone linkage.

13. The method of any of paragraphs 1-12, wherein the ASO is a morpholino or peptide nucleic acid.

14. The method of any of paragraphs 1-13, wherein the ASO comprises at least one modified base which increases binding affinity for the pre-mRNA target, which increases nuclease resistance of the antisense compound, or which decrease immune-stimulation.

15. The method of any of paragraphs 1-14, wherein the modified base is methyl-C.

16. The method of any of paragraphs 1-15, wherein the ASO is a mixture of one or more steropure molecules with a defined sequence.

17. A pharmaceutical composition comprising an ASO homolog to a nucleotide sequence that is selected from the group consisting of: SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39 and a pharmaceutically acceptable carrier for use in a method of treating a neurodegenerative disease or disorder.

Some embodiments of the technology described herein can be defined according to any of the following numbered paragraphs:

1. An antisense oligonucleotide (ASO) comprising an oligonucleotide of 8 to 40 linked nucleotides or modified nucleotides in length, wherein the ASO comprises a nucleobase sequence with homology to a 5' untranslated region (5' UTR) of a progranulin (GRN) and wherein the ASO increases GRN expression or activity in the brain.

2. The ASO of paragraph 1, wherein the ASO comprises an oligonucleotide of 8 to 40 linked nucleotides in length, which oligonucleotides comprise a sequence: a. at least 80% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, and/or SEQ ID No. 18; and b. wherein the oligonucleotide comprises at least one modified nucleotide.

3. The ASO of paragraph 1, wherein the ASO comprises an oligonucleotide of 8 to 40 linked nucleotides in length, which oligonucleotides comprise a sequence: a. at least 90% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, and/or SEQ ID No. 18; and b. wherein the oligonucleotide comprises at least one modified nucleotide.

4. The ASO of any of paragraphs 1-4, wherein the ASO comprises an oligonucleotide of 8 to 40 linked nucleotides in length, which oligonucleotides comprise a sequence: a. at least 100% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, and/or SEQ ID No. 18; and b. wherein the oligonucleotide comprises at least one modified nucleotide.

5. The ASO of any of paragraphs 1-4, wherein the ASO modulates the splicing of the pre-mRNA target.

6. The ASO of any of paragraphs 1-4, wherein the ASO targets an intron-exon or exon-intron junction of the pre-mRNA target.

7. The ASO of any of paragraphs 1-4, wherein the ASO targets a splicing enhancer or silencer element in the pre-mRNA target.

8. The ASO of any of paragraphs 1-4, wherein the ASO increases progranulin expression or activity in the brain by regulating translation efficiency of the pre-mRNA target.

9. The ASO of any of paragraphs 1-4, wherein the ASO increases progranulin expression or activity in the brain by regulating nuclear export of the pre-mRNA target.

10. The ASO of any of paragraphs 1-4, wherein the ASO increases progranulin expression or activity in the brain by regulating stability of the pre-mRNA target.

11. The ASO of any of paragraphs 1-4, wherein the ASO comprises an oligonucleotide of 8 to 40 linked nucleotides in length, which oligonucleotides comprise at least one modified nucleotide which comprises a modified sugar moiety.

12. The ASO of any of paragraphs 1-4, wherein the ASO comprises a 2' modification of its sugar moiety.

13. The ASO of any of paragraphs 1-4, wherein the ASO comprises a 2'-O-methyl, 2'-O-methoxyethyl, 2'-dimethyl-aminooxyethoxy, 2'-dimethylaminoethoxyethoxy, 2'-fluoro or 2'-acetamide modification on every sugar moiety.

14. The ASO of any of paragraphs 1-4, wherein the ASO comprises a LNA nucleobase.

15. The ASO of any of paragraphs 1-4, wherein the ASO comprises at least one modified linkage.

16. The ASO of any of paragraphs 1-4, wherein the linkage of the ASO comprises a phosphodiester, phosphotriester, or phosphorothioate backbone linkage.

17. The ASO of any of paragraphs 1-4, wherein the ASO is a morpholino or peptide nucleic acid.

18. The ASO of any of paragraphs 1-4, wherein the ASO comprises at least one modified base which increases binding affinity for the pre-mRNA target, which increases nuclease resistance of the antisense compound, or which decrease immune-stimulation.

19. The ASO of any of paragraphs 1-4, wherein the ASO comprises 5-methyl-C as a modified base.

20. The ASO of any of paragraphs 1-4, wherein the ASO is a mixture of one or more stereopure molecules with a defined sequence.

21. A composition comprising an ASO of any of paragraphs 1-20 and a pharmaceutically acceptable carrier.

22. A method of increasing the level of progranulin mRNA in a cell comprising contacting the cell with an ASO of any of paragraphs 1-20, such that the level of progranulin mRNA in the cell is increased.

23. A method of treating a neurodegenerative disease or disorder, the method comprising administering to a subject in need thereof, a therapeutically effective amount of an ASO of any of paragraphs 1-20 thereby treating the disease or disorder.

24. The method of paragraph 23, wherein the ASO modulates the splicing of the pre-mRNA target.

25. The method of any of paragraph 23, wherein the ASO targets an intron-exon or exon-intron junction of the pre-mRNA target.

26. The method of paragraph 23, wherein the modulation of splicing comprises direct binding of the ASO within 50 nucleobases upstream or downstream of an intron-exon or exon-intron junction, thereby causing a decreased frequency of use of the 5' or 3' splice site region of the pre-mRNA target.

27. The method of paragraph 23, wherein the ASO targets a splicing enhancer or silencer element in the pre-mRNA target.

28. The method of paragraph 23, wherein the modulation of splicing comprises a preferential inclusion of a segment of the pre-mRNA into a mature mRNA through inclusion of an alternative exon, extension of an exon at either 5' or 3' end, or retention of an intron.

29. The method of paragraph 23, wherein the modulation of splicing comprises a preferential exclusion of a segment of the pre-mRNA from a mature mRNA through exclusion of an alternative exon, truncation of an exon at either 5' or 3' end, or enhanced splicing of an intron.

30. The method of paragraph 23, wherein the modulation of splicing comprises the direct binding of an ASO at a splicing enhancer or silencer element, thereby causing a decreased effect of the splicing enhancer or silencer element in the pre-mRNA target.

31. The method of any of paragraphs 23-30, wherein the disease or disorder is selected from Alzheimer's disease, frontotemporal dementia, Batten disease and Parkinson's disease.

32. A method of screening for an antisense oligonucleotide (ASO) that leads to enhanced gene expression of a selected pre-mRNA target, comprising:
   a. determining or having determined whether a mammalian pre-mRNA is subject to alternative splicing involving at least part the 5' untranslated region (5' UTR) of the pre-mRNA based on gene annotations from public databases and/or RNA-seq reads obtained from mammalian biological samples, and
   b. obtaining or having obtained mammalian culturable cells that express the mRNA isoforms that are alternatively spliced in the 5' UTR region; and
   c. determining or having determined an mRNA isoform that is alternatively spliced in the 5' UTR region that gives rise to higher expression efficiency; by
   (i) determining or having determined an mRNA isoform with less upstream open reading frames (uORFs) by counting the occurrences of the "AUG" start codon and/or the Kozak consensus sequence; and/or by (ii) determining or having determined an mRNA isoform with higher nuclear export efficiency by obtaining mammalian biological samples, isolating cytoplasmic and nuclear fraction of the mRNA from the samples, and quantifying the amount of the isoforms in cytoplasm compared to nucleus; and/or by (iii) determining or having determined an mRNA isoform with higher stability by treating transcription inhibitor such as Actinomycin D to the said mammalian culturable cells and measuring the level of the 5' UTR splice isoforms at fixed time points post inhibition of transcription.

d. designing an ASO targeting the said selected pre-mRNA target that promotes preferential splicing of the pre-mRNA into the isoform with higher expression efficiency, and e. contacting the said cell or animal model with an ASO targeting the said selected pre-mRNA target, which results in preferential splicing of the pre-mRNA into the isoform with higher expression efficiency.

Some embodiments of the technology described herein can be defined according to any of the following numbered paragraphs:

1. An antisense oligonucleotide (ASO) comprising an oligonucleotide of 8 to 40 linked nucleotides or modified nucleotides in length, wherein the ASO comprises a nucleobase sequence targeting a Progranulin (GRN) mRNA to increase GRN expression or activity.

2. The ASO of paragraph 1, wherein the ASO comprises an oligonucleotide of 12 to 40 linked nucleotides in length, which oligonucleotides comprise a sequence:

a. at least 80% homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

3. The method of paragraph 1, wherein the ASO comprises an oligonucleotide of 12 to 40 linked nucleotides in length, which oligonucleotides comprise a sequence:

a. at least 90% homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

4. The ASO of paragraph 1, wherein the ASO comprises an oligonucleotide of 12 to 40 linked nucleotides nucleotides in length, which oligonucleotides comprise a sequence:

a. at least 100% homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

5. The ASO of any of paragraphs 1-4, wherein the ASO increase GRN expression or activity in the central nervous system.

6. The ASO of any of paragraphs 1-5, wherein the disease or disorder is selected from Alzheimer's disease, Fronto-temporal Dementia, Batten disease and Parkinson's disease.

7. The ASO of any of paragraphs 1-6, wherein said progranulin (GRN) expression or activity in the brain is modulated by splicing of a pre-mRNA target.

8. The ASO of any of paragraphs 1-7, wherein the ASO comprises an oligonucleotide of 12 to 40 linked nucleotides in length, which oligonucleotides comprise at least one modified nucleotide which comprises a modified sugar moiety.

9. The ASO of any of paragraphs 1-8, wherein the ASO comprises a 2' modification of its sugar moiety.

10. The ASO of any of paragraphs 1-9, wherein the ASO comprises a 2'-o-methyl, 2'-methoxyethoxy, 2'-dimethylaminooxyethoxy, 2'-dimethylaminoethoxyethoxy, 2'-fluoro or 2'-acetamide modification on every sugar moiety.

11. The ASO of any of paragraphs 1-10, wherein the ASO comprises a LNA nucleobase.

12. The ASO of any of paragraphs 1-11, wherein the ASO comprises at least one modified linkage.

13. The ASO of any of paragraphs 1-12, wherein the linkage of the ASO comprises a phosphodiester, phosphotrester, or phosphorothioate backbone linkage.

14. The ASO of any of paragraphs 1-13, wherein the ASO is a morpholino or peptide nucleic acid.

15. The ASO of any of paragraphs 1-14, wherein the ASO comprises at least one modified base which increases binding affinity for the pre-mRNA target, which increases nuclease resistance of the antisense compound, or which decrease immune-stimulation.

16. The ASO of any of paragraphs 1-15, wherein the modified base is methyl-C.

17. The ASO of any of paragraphs 1-16, wherein the ASO is a mixture of one or more steropure molecules with a defined sequence.

18. An antisense oligonucleotide (ASO) comprising an oligonucleotide of 8 to 40 linked nucleotides or modified nucleotides in length, wherein the ASO comprises a nucleobase sequence with homology to a 5' untranslated region (5' UTR) of a progranulin (GRN) and wherein the ASO increases GRN expression or activity in the brain.

19. The ASO of paragraph 18, wherein the ASO comprises an oligonucleotide of 8 to 40 linked nucleotides in length, which oligonucleotides comprise a sequence:

a. at least 80% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

20. The ASO of paragraph 18, wherein the ASO comprises an oligonucleotide of 8 to 40 linked nucleotides in length, which oligonucleotides comprise a sequence:

a. at least 90% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

21. The ASO of paragraphs 18, wherein the ASO comprises an oligonucleotide of 8 to 40 linked nucleotides in length, which oligonucleotides comprise a sequence:

a. at least 100% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

22. The ASO of any of paragraphs 18-21, wherein the ASO modulates the splicing of the pre-mRNA target.

23. The ASO of any of paragraphs 18-22, wherein the ASO targets an intron-exon or exon-intron junction of the pre-mRNA target.

24. The ASO of any of paragraphs 18-23, wherein the ASO targets a splicing enhancer or silencer element in the pre-mRNA target.

25. The ASO of any of paragraphs 18-24, wherein the ASO increases progranulin expression or activity in the brain by regulating translation efficiency of the pre-mRNA target.

26. The ASO of any of paragraphs 18-25, wherein the ASO increases progranulin expression or activity in the brain by regulating nuclear export of the pre-mRNA target.

27. The ASO of any of paragraphs 18-26, wherein the ASO increases progranulin expression or activity in the brain by regulating stability of the pre-mRNA target.

28. The ASO of any of paragraphs 18-27, wherein the ASO comprises an oligonucleotide of 8 to 40 linked nucleotides in length, which oligonucleotides comprise at least one modified nucleotide which comprises a modified sugar moiety.

29. The ASO of any of paragraphs 18-28, wherein the ASO comprises a 2' modification of its sugar moiety.

30. The ASO of any of paragraphs 18-29, wherein the ASO comprises a 2'-O-methyl, 2'-O-methoxyethyl, 2'-dimethylaminooxyethoxy, 2'-dimethylaminoethoxyethoxy, 2'-fluoro or 2'-acetamide modification on every sugar moiety.

31. The ASO of any of paragraphs 18-30, wherein the ASO comprises a LNA nucleobase.

32. The ASO of any of paragraphs 18-31, wherein the ASO comprises at least one modified linkage.

33. The ASO of any of paragraphs 18-32, wherein the linkage of the ASO comprises a phosphodiester, phosphotriester, or phosphorothioate backbone linkage.

34. The ASO of any of paragraphs 18-33, wherein the ASO is a morpholino or peptide nucleic acid.

35. The ASO of any of paragraphs 18-34, wherein the ASO comprises at least one modified base which increases binding affinity for the pre-mRNA target, which increases nuclease resistance of the antisense compound, or which decrease immune-stimulation.

36. The ASO of any of paragraphs 18-35, wherein the ASO comprises 5-methyl-C as a modified base.

37. The ASO of any of paragraphs 18-36, wherein the ASO is a mixture of one or more stereopure molecules with a defined sequence.

38. A composition comprising an ASO of any of paragraphs 1-37 and a pharmaceutically acceptable carrier.

39. A method of increasing the level of progranulin mRNA in a cell comprising contacting the cell with an ASO of any of paragraphs 1-37, such that the level of progranulin mRNA in the cell is increased.

40. A method of treating a neurodegenerative disease or disorder, the method comprising administering to a subject in need thereof, a therapeutically effective amount of an ASO of any of paragraphs 1-37 thereby treating the disease or disorder.

41. The method of paragraph 40, wherein the ASO modulates the splicing of the pre-mRNA target.

42. The method of any of paragraphs 40-41, wherein the ASO targets an intron-exon or exon-intron junction of the pre-mRNA target.

43. The method of any of paragraphs 40-42, wherein the modulation of splicing comprises direct binding of the ASO within 50 nucleobases upstream or downstream of an intron-exon or exon-intron junction, thereby causing a decreased frequency of use of the 5' or 3' splice site region of the pre-mRNA target.

44. The method of any of paragraphs 40-43, wherein the ASO targets a splicing enhancer or silencer element in the pre-mRNA target.

45. The method of any of paragraphs 40-44, wherein the modulation of splicing comprises a preferential inclusion of a segment of the pre-mRNA into a mature mRNA through inclusion of an alternative exon, extension of an exon at either 5' or 3' end, or retention of an intron.

46. The method of any of paragraphs 40-45, wherein the modulation of splicing comprises a preferential exclusion of a segment of the pre-mRNA from a mature mRNA through exclusion of an alternative exon, truncation of an exon at either 5' or 3' end, or enhanced splicing of an intron.

47. The method of any of paragraphs 40-46, wherein the modulation of splicing comprises the direct binding of an ASO at a splicing enhancer or silencer element, thereby causing a decreased effect of the splicing enhancer or silencer element in the pre-mRNA target.

48. The method of any of paragraphs 40-47, wherein the disease or disorder is selected from the group of Alzheimer's disease, frontotemporal dementia, Batten disease, and Parkinson's disease.

49. A method of screening for an antisense oligonucleotide (ASO) that leads to enhanced gene expression of a selected pre-mRNA target, comprising:

a. determining or having determined whether a mammalian pre-mRNA is subject to alternative splicing involving at least part the 5' untranslated region (5' UTR) of the pre-mRNA based on gene annotations from public databases and/or RNA-seq reads obtained from mammalian biological samples, and b. obtaining or having obtained mammalian culturable cells that express the mRNA isoforms that are alternatively spliced in the 5' UTR region; and c. determining or having determined an mRNA isoform that is alternatively spliced in the 5' UTR region that gives rise to higher expression efficiency; by (i) determining or having determined an mRNA isoform with less upstream open reading frames (uORFs) by counting the occurrences of the "AUG" start codon and/or the Kozak consensus sequence; and/or by (ii) determining or having determined an mRNA isoform with higher nuclear export efficiency by obtaining mammalian biological samples, isolating cytoplasmic and nuclear fraction of the mRNA from the samples, and quantifying the amount of the isoforms in cytoplasm compared to nucleus; and/or by (iii) determining or having determined an mRNA isoform with higher stability by treating transcription inhibitor such as Actinomycin D to the said mammalian culturable cells and measuring the level of the 5' UTR splice isoforms at fixed time points post inhibition of transcription.

d. designing an ASO targeting the said selected pre-mRNA target that promotes preferential splicing of the pre-mRNA into the isoform with higher expression efficiency, and e. contacting the said cell or animal model with an ASO targeting the said selected pre-mRNA target, which results in preferential splicing of the pre-mRNA into the isoform with higher expression efficiency.

50. A composition comprising an ASO and a pharmaceutically acceptable carrier for use in the treatment of a neurodegenerative disease or disorder.

51. The composition for use of paragraph 50, comprising an ASO of 8 to 40 linked nucleotides or modified nucleotides in length, wherein the ASO comprises a nucleobase sequence targeting a progranulin (GRN) mRNA and wherein the ASO increases GRN expression or activity in the brain.

52. The composition for use of any of paragraphs 50-51, wherein the ASO comprises an oligonucleotide of 8 to 40 linked nucleotides in length, which oligonucleotides comprise a sequence:

a. at least 80% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide. 53. The composition for use of any of paragraphs 50-52, wherein the ASO comprises an oligonucleotide of 8 to 40 linked nucleotides in length, which oligonucleotides comprise a sequence:

a. at least 90% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

54. The composition for use of any of paragraphs 50-53, wherein the ASO comprises an oligonucleotide of 8 to 40 linked nucleotides in length, which oligonucleotides comprise a sequence:

a. at least 100% homologous to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and b. wherein the oligonucleotide comprises at least one modified nucleotide.

55. The composition for use of any of paragraphs 50-54, wherein the ASO modulates the splicing of the pre-mRNA target.

56. The composition for use of any of paragraphs 50-55, wherein the ASO targets an intron-exon or exon-intron junction of the pre-mRNA target.

57. The composition for use of any of paragraphs 50-56, wherein the ASO targets a splicing enhancer or silencer element in the pre-mRNA target.

58. The composition for use of any of paragraphs 50-57, wherein the ASO increases progranulin expression or activity in the brain by regulating translation efficiency of the pre-mRNA target.

59. The composition for use of any of paragraphs 50-58, wherein the ASO increases progranulin expression or activity in the brain by regulating nuclear export of the pre-mRNA target.

60. The composition for use of any of paragraphs 50-59, wherein the ASO increases progranulin expression or activity in the brain by regulating stability of the pre-mRNA target.

61. The composition for use of any of paragraphs 50-60, wherein the ASO comprises an oligonucleotide of 8 to 40 linked nucleotides in length, which oligonucleotides comprise at least one modified nucleotide which comprises a modified sugar moiety.

62. The composition for use of any of paragraphs 50-61, wherein the ASO comprises a 2' modification of its sugar moiety.

63. The composition for use of any of paragraphs 50-62, wherein the ASO comprises a 2'-O-methyl, 2'-O-methoxyethyl, 2'-dimethylaminooxyethoxy, 2'-dimethylaminoethoxyethoxy, 2'-fluoro or 2'-acetamide modification on every sugar moiety.

64. The composition for use of any of paragraphs 50-63, wherein the ASO comprises a LNA nucleobase.

65. The composition for use of any of paragraphs 50-64, wherein the ASO comprises at least one modified linkage.

66. The composition for use of any of paragraphs 50-65, wherein the linkage of the ASO comprises a phosphodiester, phosphotriester, or phosphorothioate backbone linkage.

67. The composition for use of any of paragraphs 50-66, wherein the ASO is a morpholino or peptide nucleic acid.

68. The composition for use of any of paragraphs 50-67, wherein the ASO comprises at least one modified base which increases binding affinity for the pre-mRNA target, which increases nuclease resistance of the antisense compound, or which decrease immune-stimulation.

69. The composition for use of any of paragraphs 50-68, wherein the ASO comprises 5-methyl-C as a modified base.

70. The composition for use of any of paragraphs 50-69, wherein the ASO is a mixture of one or more stereopure molecules with a defined sequence.

71. The composition for use of any of paragraphs 50-70, wherein the ASO modulates the splicing of the pre-mRNA target.

72. The composition for use of any of paragraphs 50-71, wherein the ASO targets an intron-exon or exon-intron junction of the pre-mRNA target.

73. The composition for use of any of paragraphs 50-72, wherein the modulation of splicing comprises direct binding of the ASO within 50 nucleobases upstream or downstream of an intron-exon or exon-intron junction, thereby causing a decreased frequency of use of the 5' or 3' splice site region of the pre-mRNA target.

74. The composition for use of any of paragraphs 50-73, wherein the ASO targets a splicing enhancer or silencer element in the pre-mRNA target.

75. The composition for use of any of paragraphs 50-74, wherein the modulation of splicing comprises a preferential inclusion of a segment of the pre-mRNA into a mature mRNA through inclusion of an alternative exon, extension of an exon at either 5' or 3' end, or retention of an intron.

76. The composition for use of any of paragraphs 50-75, wherein the modulation of splicing comprises a preferential exclusion of a segment of the pre-mRNA from a mature mRNA through exclusion of an alternative exon, truncation of an exon at either 5' or 3' end, or enhanced splicing of an intron.

77. The composition for use of any of paragraphs 50-76, wherein the modulation of splicing comprises the direct binding of an ASO at a splicing enhancer or silencer element, thereby causing a decreased effect of the splicing enhancer or silencer element in the pre-mRNA target.

78. The composition for use of any of paragraphs 50-77, wherein the disease or disorder is selected from the group of Alzheimer's disease, frontotemporal dementia, Batten disease, and Parkinson's disease.

79. A method of treating a neurodegenerative disease or disorder, the method comprising administering to a subject in need thereof, a therapeutically effective amount of an antisense oligonucleotide (ASO) targeting an intron of a Progranulin (GRN) mRNA to increase GRN expression or activity in the brain, thereby treating the disease or disorder.

80. The method of paragraph 79, wherein the ASO comprises an oligonucleotide of 12 to 40 linked nucleotides in length, which oligonucleotides comprise a sequence:
   a. at least 80% homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and
   b. wherein the oligonucleotide comprises at least one modified nucleotide.

81. The method of paragraph 79, wherein the ASO comprises an oligonucleotide of 12 to 40 linked nucleotides in length, which oligonucleotides comprise a sequence:
   a. at least 90% homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and
   b. wherein the oligonucleotide comprises at least one modified nucleotide.

82. The method of paragraph 79, wherein the ASO comprises an oligonucleotide of 12 to 40 linked nucleotides nucleotides in length, which oligonucleotides comprise a sequence:
   a. at least 100% homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39; and
   b. wherein the oligonucleotide comprises at least one modified nucleotide.

83. The method of any of paragraphs 79-82, wherein the disease or disorder is selected from Alzheimer's disease, Frontotemporal Dementia, Batten disease and Parkinson's disease.

84. The method of any of paragraphs 79-83, wherein said progranulin (GRN) expression or activity in the brain is modulated by splicing of a pre-mRNA target.

85. The method of any of paragraphs 79-84, wherein the ASO comprises an oligonucleotide of 12 to 40 linked nucleotides in length, which oligonucleotides comprise at least one modified nucleotide which comprises a modified sugar moiety.

86. The method of any of paragraphs 79-85, wherein the ASO comprises a 2' modification of its sugar moiety.

87. The method of any of paragraphs 79-86, wherein the ASO comprises a 2'-o-methyl, 2'-methoxyethoxy, 2'-dimethylaminooxyethoxy, 2'-dimethylaminoethoxyethoxy, 2'-fluoro or 2'-acetamide modification on every sugar moiety.

88. The method of any of paragraphs 79-87, wherein the ASO comprises a LNA nucleobase.

89. The method of any of paragraphs 79-88, wherein the ASO comprises at least one modified linkage.

90. The method of any of paragraphs 79-89, wherein the linkage of the ASO comprises a phosphodiester, phospho-trester, or phosphorothioate backbone linkage.

91. The method of any of paragraphs 79-90, wherein the ASO is a morpholino or peptide nucleic acid.

92. The method of any of paragraphs 79-91, wherein the ASO comprises at least one modified base which increases binding affinity for the pre-mRNA target, which increases nuclease resistance of the antisense compound, or which decrease immune-stimulation.

93. The method of any of paragraphs 79-92, wherein the modified base is methyl-C.

94. The method of any of paragraphs 79-92, wherein the ASO is a mixture of one or more steropure molecules with a defined sequence.

95. A pharmaceutical composition comprising an ASO homolog to a nucleotide sequence that is selected from the group consisting of: SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, and/or SEQ ID No. 39 and a pharmaceutically acceptable carrier for use in a method of treating a neurodegenerative disease or disorder.

EXAMPLES

Example 1: Antisense Oligonucleotide-Based Progranulin Augmentation Therapy in Neurodegenerative Diseases Progranulin is a GRN-encoded protein that, when secreted into cerebrospinal fluid, plays a critical neuroprotective function. Recent studies have shown that progranulin augmentation may have therapeutic effects in diverse neurodegenerative diseases including Alzheimer's disease and Parkinson's disease. However, no treatment targeting progranulin is available currently. Remarkable success of nusinersen/Spinraza for spinal muscular atrophy in recent months clearly demonstrated that antisense oligonucleotides (ASOs) can induce sustained gene upregulation in neuronal tissues by modulation of mRNA splicing toward a productive isoform.

The inventors analyzed a compendium of public RNA-seq datasets and identified an unproductive isoform of GRN specifically in brain tissues. The isoform retains intron 4, which leads to rapid nonsense-mediated decay of the transcripts. The inventors developed an ASO therapy that reduces the intron retention. Further analyses revealed splice silencing elements in/near the intron that, when targeted by ASOs, can improve splicing of the intron and thereby induce upregulation of GRN to a therapeutically relevant level.

GRN encodes a protein called progranulin, which, when secreted into the cerebrospinal fluid (CSF), plays critical roles in neuroprotective and neuroimmunomodulatory function. Although GRN had been primarily known for causal genetic links to frontotemporal dementia (FTD; when one allele is inactivated) and Batten disease (when both alleles are inactivated), recent studies have strongly suggested a much wider role in providing protection against neurodegenerative diseases (Benussi et al., 2017) including Alzheimer's disease (AD), Parkinson's disease (PD), which in aggregate affect tens of millions of people worldwide.

Specifically, GRN rs5848, a SNP that is linked to progranulin deficiency, was found to be associated with the risk of AD and PD in multiple studies (Chen et al., 2015). Progranulin deficiency was also reported to cause spurious microglia activation called "microgliosis," a hallmark of AD (Lui et al., 2016). In addition, recent studies showed that viral delivery of progranulin in mouse models of AD (Minami et al., 2014), PD (Van Kampen et al., 2014), FTD (Arrant et al., 2017), and Batten disease (Arrant et al., 2018) reduces respective disease pathology in a dose-dependent manner. Together, these studies point to progranulin enhancement as a promising treatment for the diseases.

A number of small molecule drugs were serendipitously found to induce GRN upregulation through indirect mechanisms, such as ion channel modulation and epigenetic modulation. However, these candidates, mostly discovered from in vitro screens, performed poorly in clinical trials (Alberici et al., 2014; Sha et al., 2017), presumably due to inefficient delivery among other reasons. Small molecule drugs often distribute poorly to brain upon oral or intravenous administration due to low blood-brain barrier penetration, and intrathecal administration is usually not an option due to low solubility. In addition, no gene therapy studies of progranulin have been reported beyond mice (Arrant et al., 2018).

GRN, aside from being an unclaimed target for highly prevalent neurodegenerative diseases, has other properties that make it attractive as an intrathecal ASO drug target: Because it encodes a soluble, secreted protein, even if the drug does not get into disease-inflicted cells, it can be have therapeutic effect on them by boosting CSF-circulating progranulin level through other cells in central nervous system. Because CSF sample can be readily collected at every intrathecal dosing, circulating progranulin level in CSF is a useful biomarker for monitoring drug response and adjusting dosage.

The inventor's investigation identified that splice-modulating ASOs can potentially induce upregulation of GRN through the reduction of intron retention. The inventors designed ASOs based on the inventors' computational analysis, develop assays and perform ASO screening using a cell line that has brain-like GRN splicing pattern, and fine-tune and validate the lead ASO in patient-derived cells.

Figure 1B:
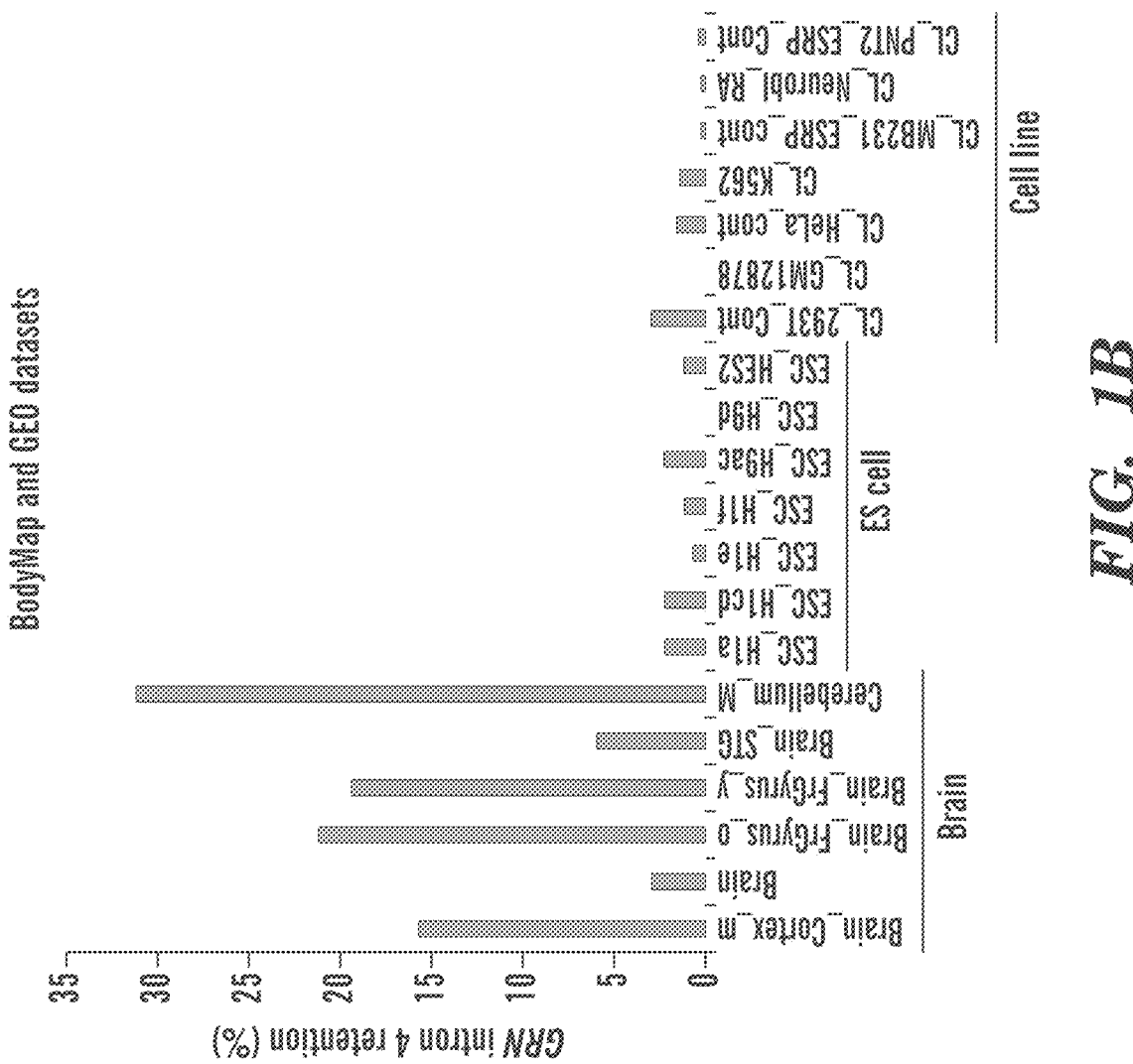
Figure 1C:
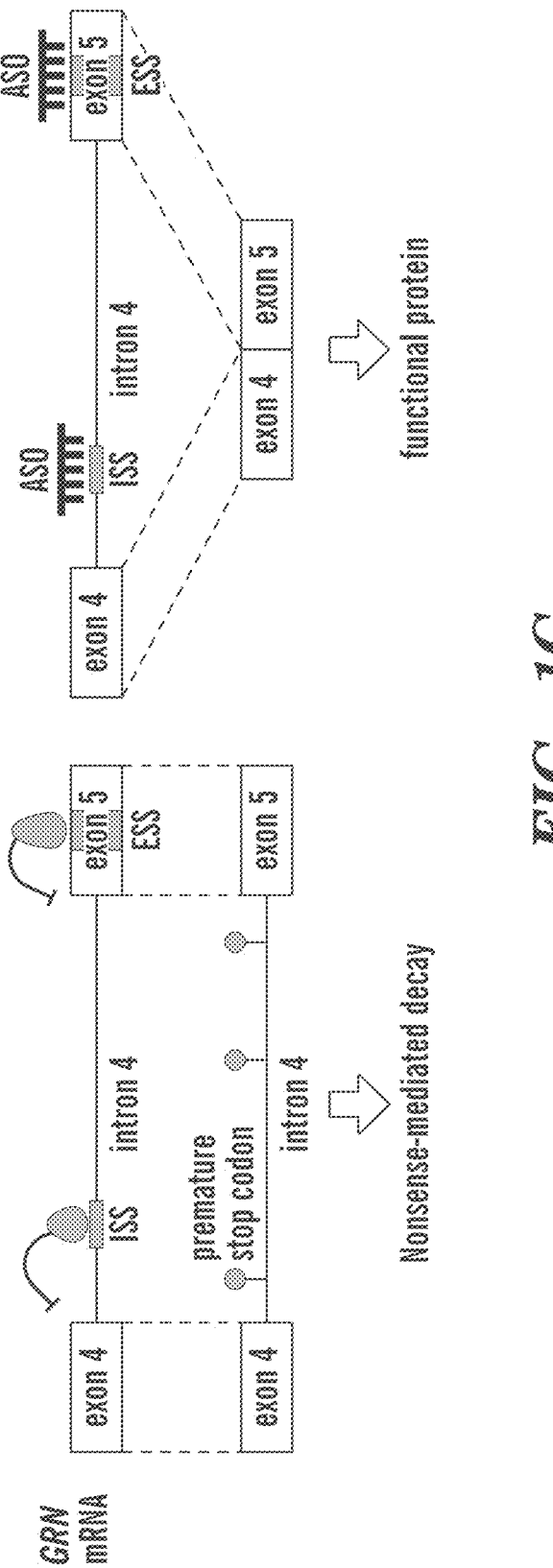

Substantial retention of GRN intron 4. Computational analysis of the compendium of GTEx, BodyMap and GEO RNA-seq datasets revealed substantial retention of GRN intron 4 specifically in brain tissues with retention rate of 15-31% (FIG. 1A-1B). Intron 4, if retained, introduces premature stop codons that should trigger nonsense-mediated decay of the transcripts, therefore, ASOs that reduce the intron retention leads to upregulation of GRN (FIG. 2).

The observed 15-30% intron retention rate in the brain data may seem low enough that one might think derepressing it may not lead to therapeutically relevant level of upregulation. However, that intron retention rate is an underestimate. Any intron-retaining transcripts, when exported out of nucleus, are subject to rapid nonsense-mediated decay. Thus, only those intron-retaining transcripts in the nucleus are detected by RNA-seq. As cytoplasmic mRNAs are 10-100 times more abundant than nuclear mRNAs (Grindberg et al., 2013), the actual amount of intron-retaining transcripts (nuclear and cytoplasmic; before NMD is activated) is likely to be 10-100 times higher than the amount detected in RNA-seq. Thus, complete suppression of the GRN intron retention can lead to increase in GRN expression by up to 30 folds (assuming 30% intron retention and 100:1 cytoplasmic to nuclear mRNA abundance ratio) or at least by 150% (assuming 15% intron retention and 10:1 cytoplasmic to nuclear mRNA abundance ratio), which would be high enough to have therapeutic effect. It is possible that toxicity may occur if ASOs overshoot the CSF progranulin level. However, it can be prevented by adaptively controlling ASO dosage at each administration based on the real time CSF progranulin level as a biomarker of response.

Figure 2A:
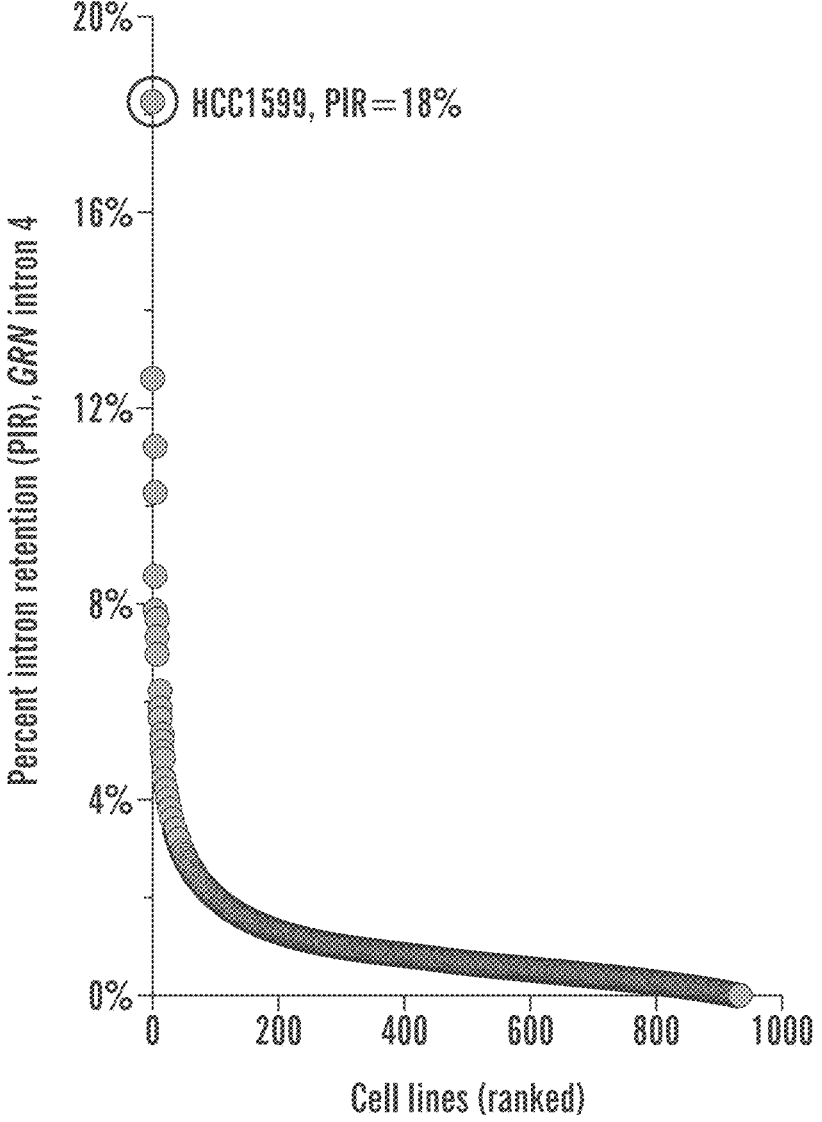
FIGS. 2A-2B demonstrate the cell line selection for screening.
Figure 2B:
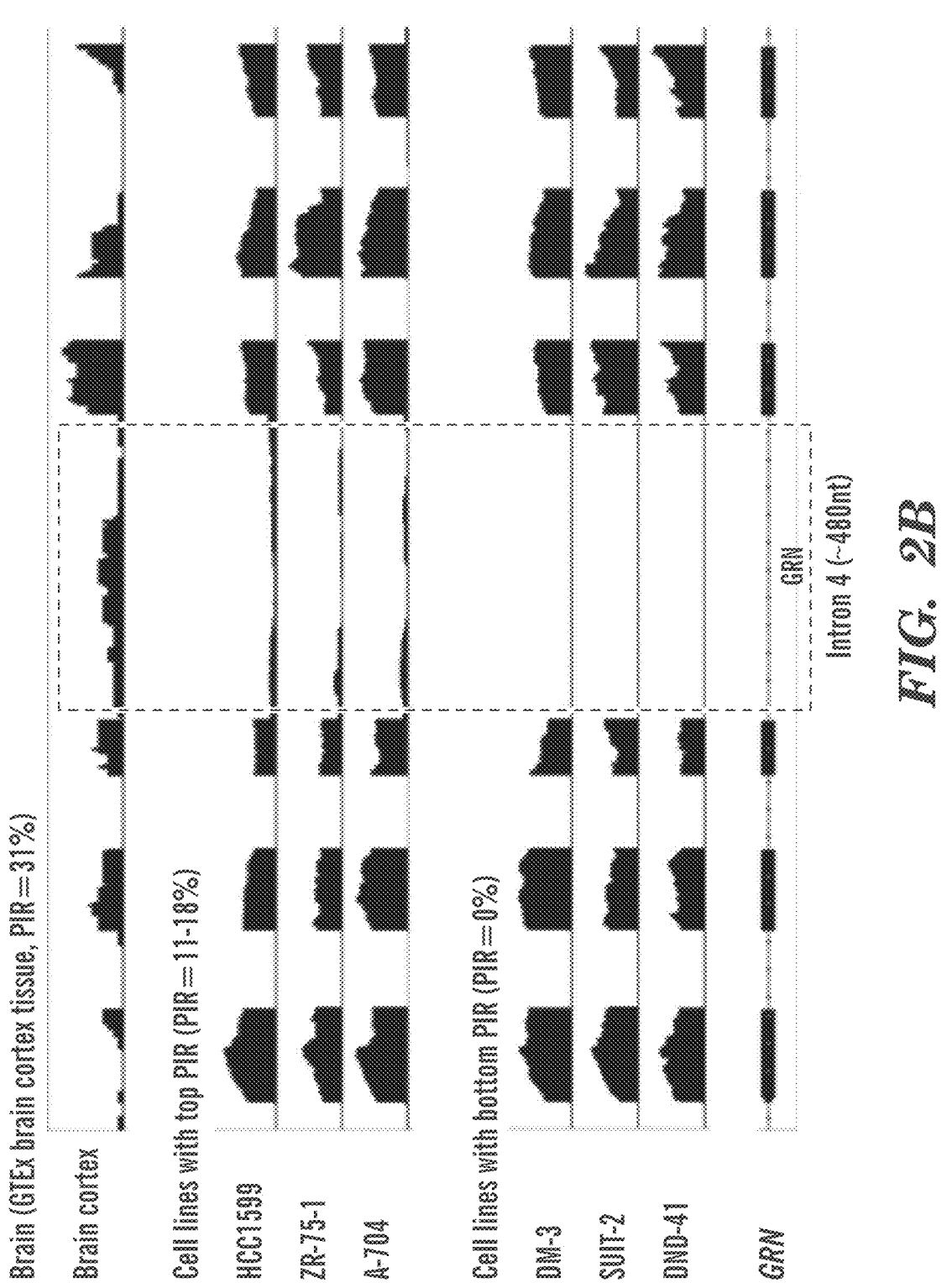

Selection of a cell line suitable for ASO screening. Because the inventors are looking for ASOs that act on a wild type copy of GRN, it is not necessary to use patient-derived cell lines at screening stage. However, it is important to use a cell line that has robust GRN intron 4 retention, as do brain tissues. To find such cell lines, the inventors downloaded the CCLE RNA-seq dataset for 933 cell lines and ranked them based on intron 4 retention level (all cell lines robustly expressed GRN). The retention level ranged from 0 to 18% (FIG. 2A). The inventors picked HCC1599 that showed the highest GRN intron 4 retention level (FIG. 2B). The intron retention level of 18% is in line with the level of a panel of brain tissues (15-31%; FIG. 1A).

Figure 3:
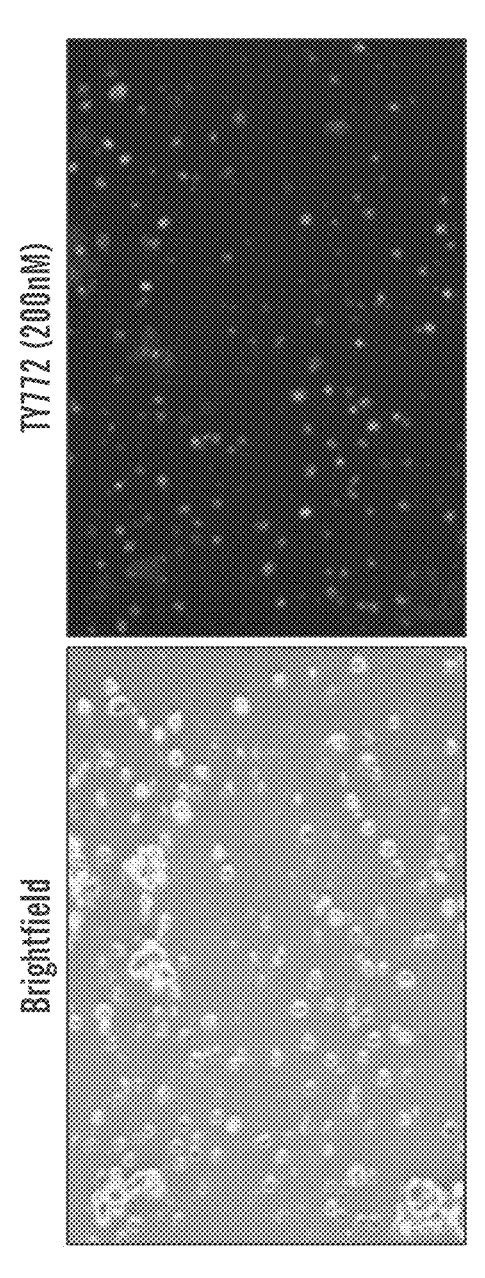
FIG. 3 demonstrates the efficient transfection of ASOs into HCC1599 cell line. Assessed by transfection of a FAM-conjugated control ASO (TY772). Images were taken 48 hours after transfection. Transfection was done using Lipofectamine 3000 reagent.

The inventors have chosen to use HCC1599 cell line for screening and confirmed that the cell line is robustly transfectable (30-60%; FIG. 3). Alternatively, the inventors can switch HCC1599 to ZR-75-1 cell line, which showed second highest GRNintron 4 retention level (FIG. 2B).

Figure 6A:
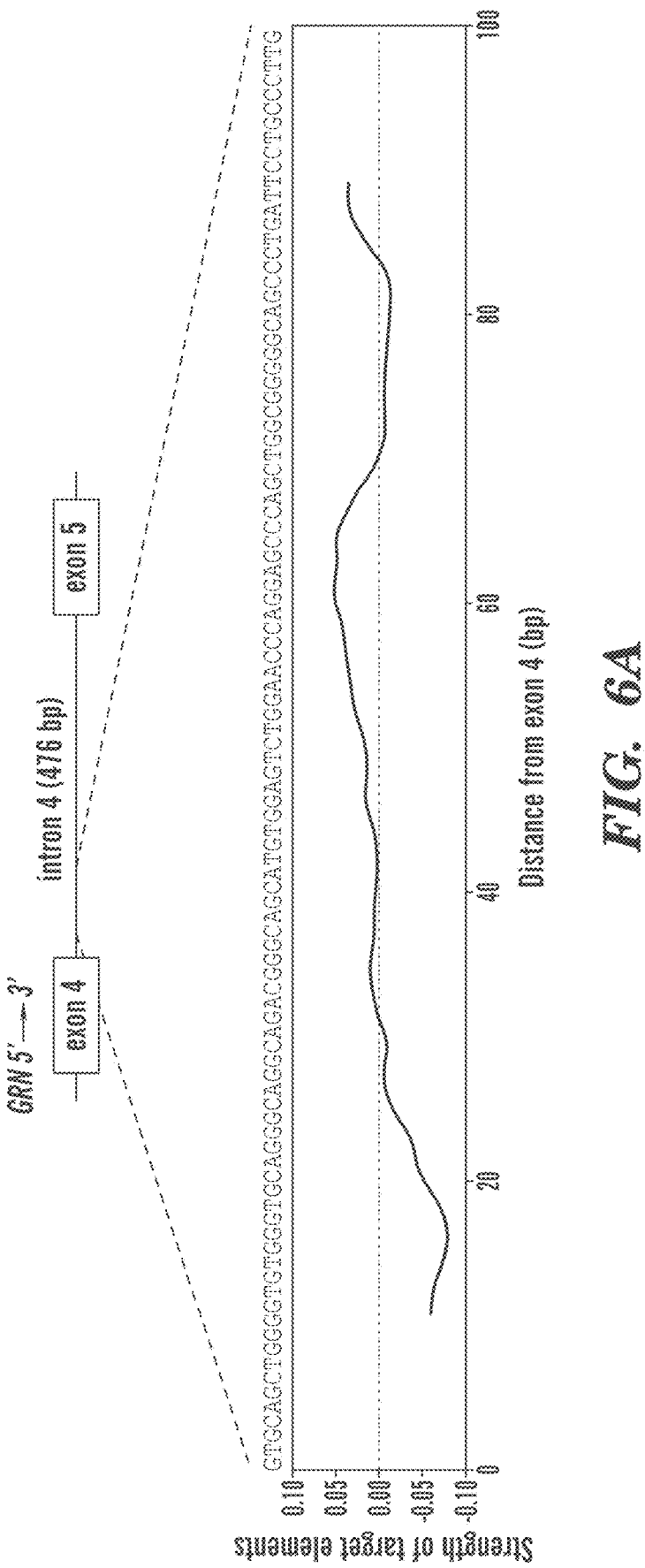
FIG. 6A shows the strength of splice regulatory elements in GRN intron 4 that are, when blocked by an ASO, predicted to enhance intron 4 splicing. The prediction was made by reanalysis of published works on splicing regulatory elements (Wang et al., 2004; Rosenberg et al., 2015).
Figure 6B:
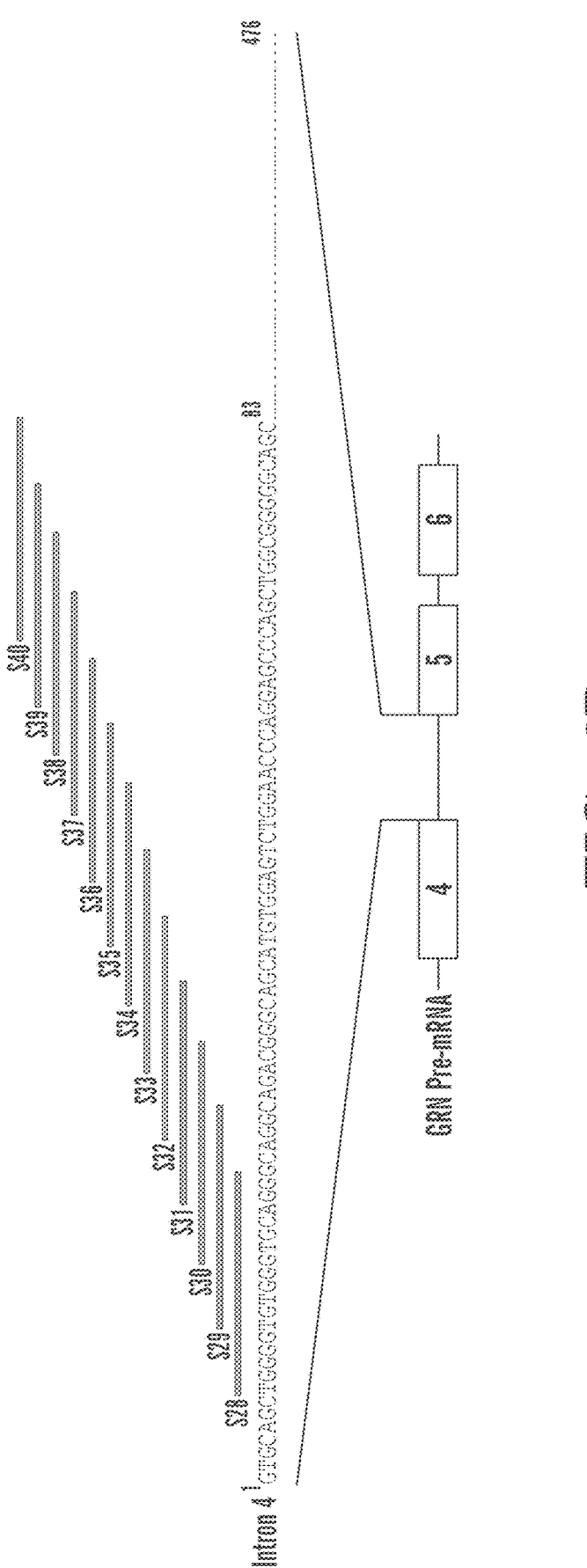
FIG. 6B shows antisense oligonucleotides (ASOs) assessed for efficacy in improving GRN intron 4 splicing. The ASOs were phosphorothioate (PS) and 2'MOE (2'-O-methoxyethyl)-modified.

Design of candidate ASOs and screening. A total of 13 ASOs (SEQ ID No. 27-39) that block the regions in and around the predicted splice regulatory elements were designed (FIGS. 6A-6B). For ASO chemistry, the inventors used 2'-MOE (methoxyethyl)-modification in sugar rings and phophorothioate in the backbone. This chemistry provides nuclease resistance, stronger binding, and lower immunogenicity (Khvorova and Watts, 2017), and is used by FDA-approved ASOs, including nusinersen/Spinraza and mipomersen/Kynamro.

The inventors identified a cell line model that shows a robust transfection efficiency and recapitulates the target tissue (brain cortex) in terms of the intron 4 retention pattern of GRN gene (FIGS. 2A-2B and FIG. 3)

Figures 5A, 5B, 5C:
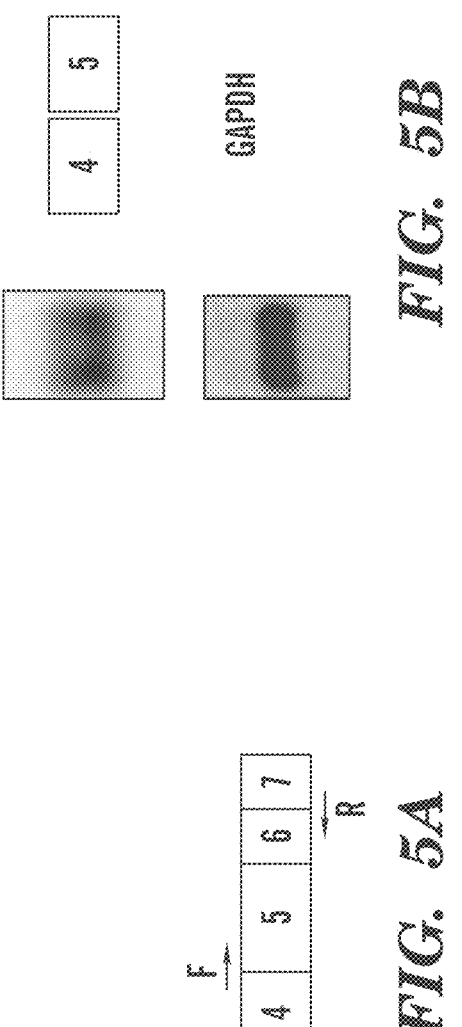
FIGS. 5A-5C demonstrate a reverse transcription (RT)-PCR assay for measuring the level of intron 4-spliced GRN mRNAs, normalized to GAPDH mRNA level.

Established assays that can accurately determine the efficacy of antisense oligonucleotides (ASOs) in decreasing the intron 4 retention rate (FIGS. 4A-4C) and in increasing the level of functional GRN mRNA (FIGS. 5A-5C)

Designed ASOs based on computational predictions on their impact on splicing (FIGS. 6A-B)

Identified S37, a candidate ASO that gives rise to ~2 fold decrease in intron 4 retention rate and an increase in functional mRNA level of the GRN gene to a similar extent (FIGS. 6A-B, FIGS. 8A-8B, FIGS. 9A-9C)

Figure 10:
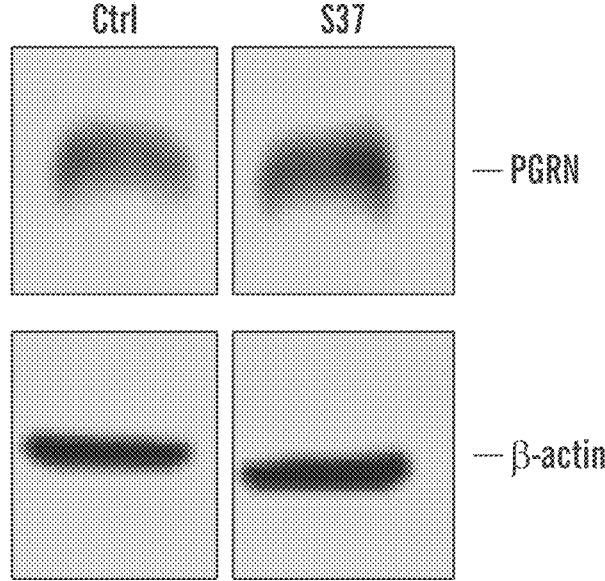
FIG. 10 shows a measurement of progranulin protein levels by Western blotting. The levels of progranulin protein (PGRN) were measured after transfection with Control (Ctrl) and S37 ASOs.
Figure 11:
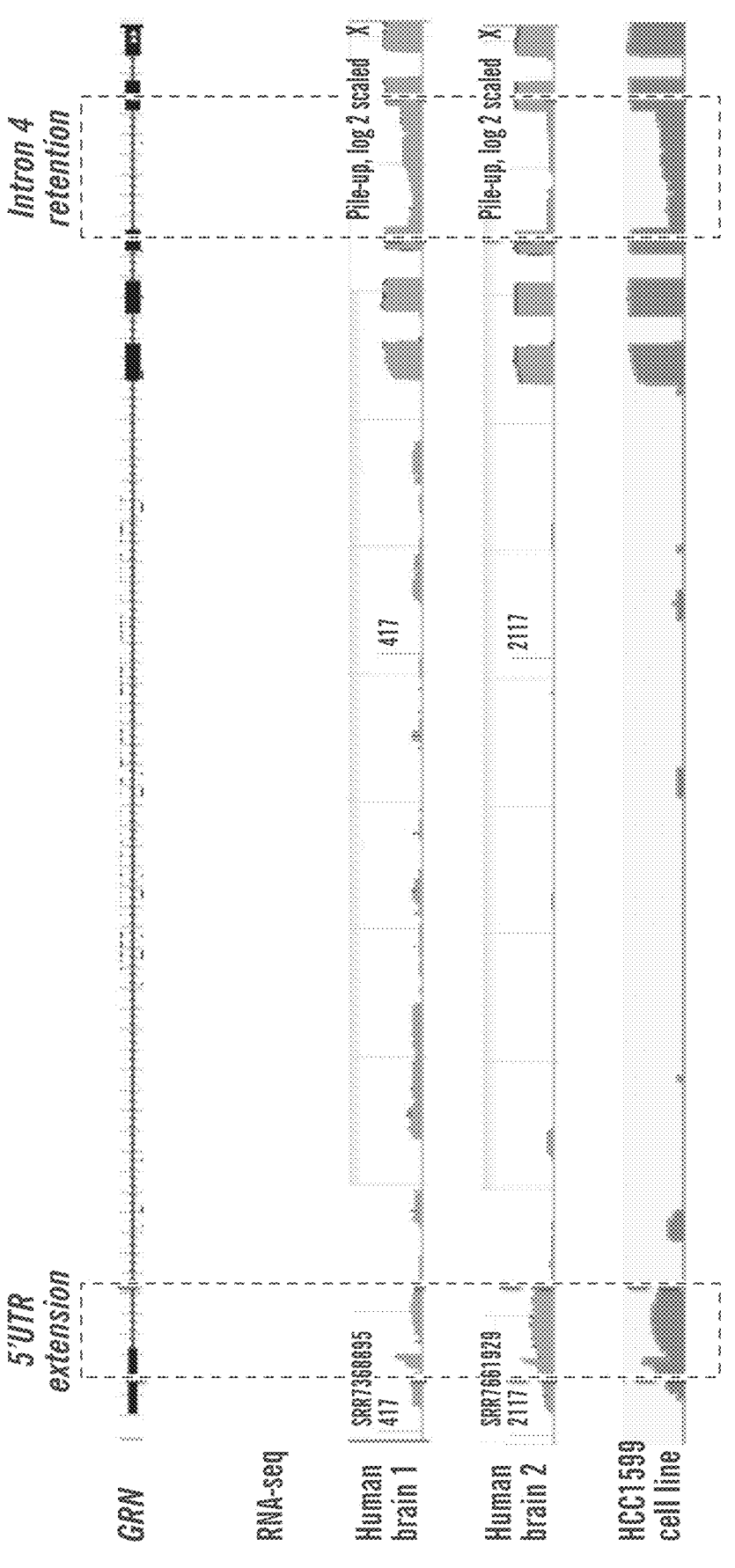
FIG. 11 shows RNA-seq coverage of human brain tissue of HCC1599 cell line at the GRN gene 5' UTR and intron 4 regions, indicating 5' UTR extension and intron 4 retention.
Figure 12:
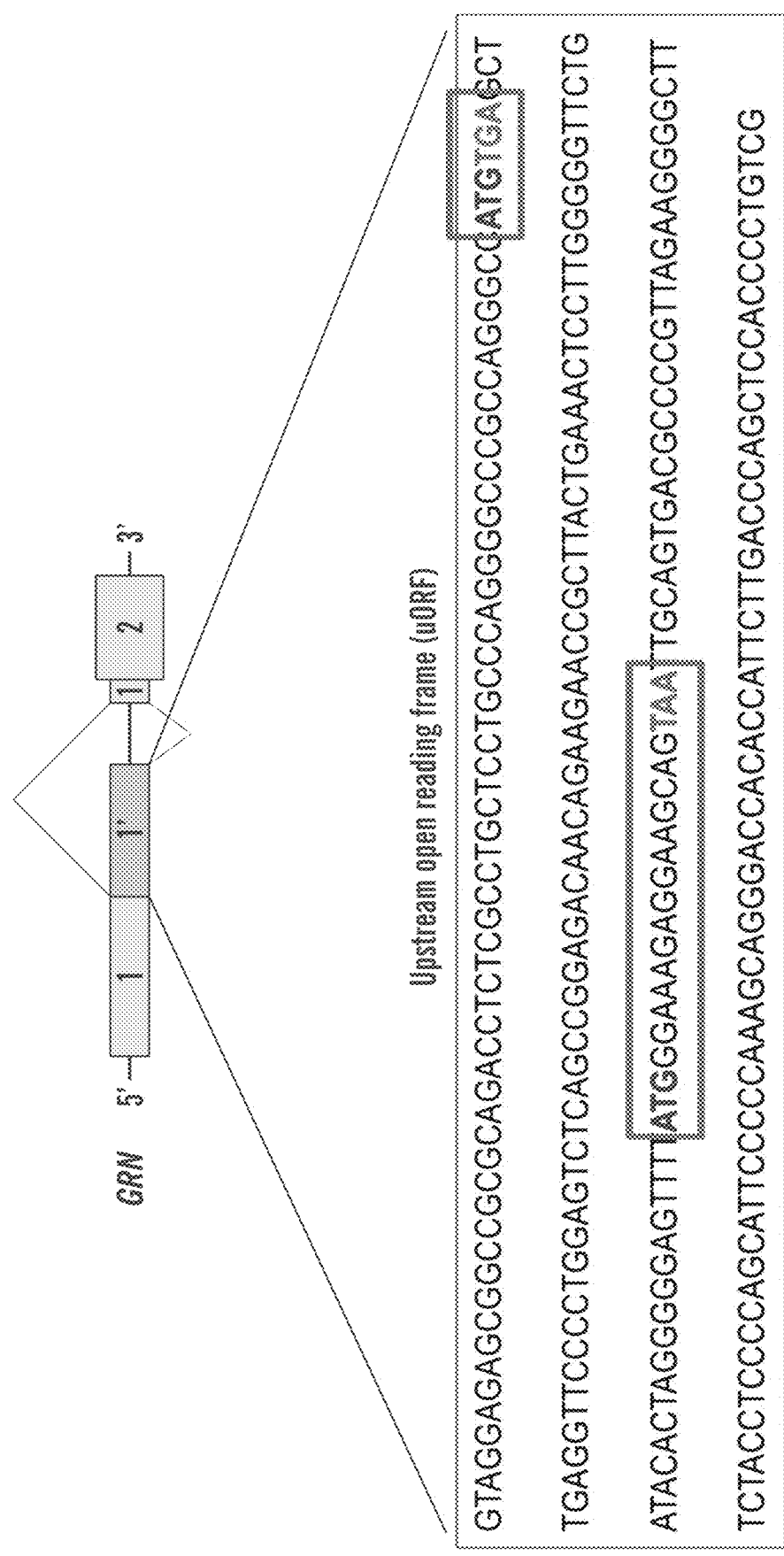
FIG. 12 shows upstream open reading frames in the extended 5' UTR region of GRN (SEQ ID NO: 48).
Figures 13A, 13B:
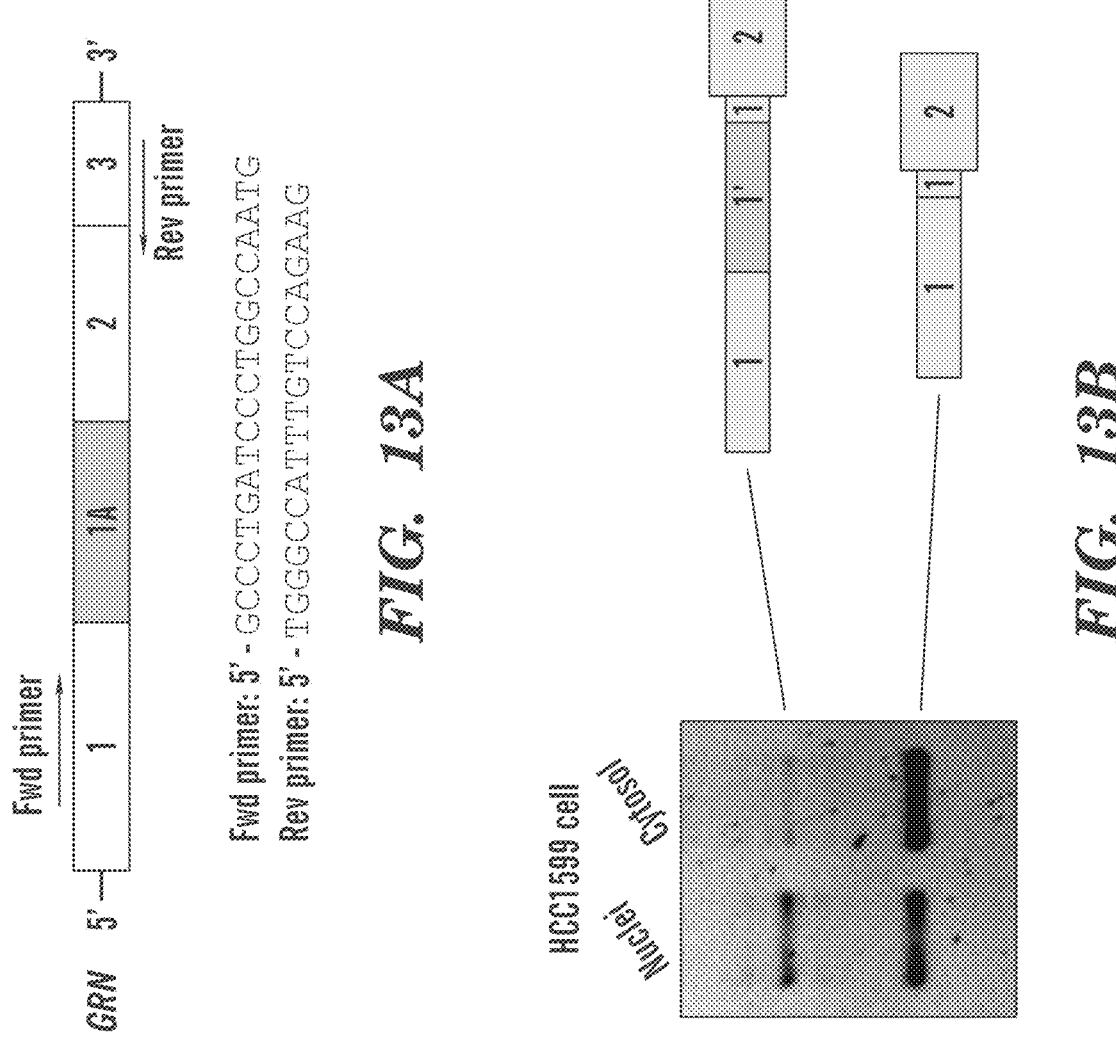
FIG. 13A shows the location and sequence of the forward (fwd, SEQ ID No. 19) and reverse (rev, SEQ ID No. 20) primers for RT-PCR assay to determine the relative level of the 5' UTR-extended or-unextended forms of GRN transcripts.
FIG. 13B shows the 5' UTR-extended form of GRN transcripts is depleted in the cytosol compared to nuclei, indicating that the 5' UTR-extended form of GRN transcript is inefficiently exported out of nuclei.

The Western blotting assay for GRN was optimized (FIG. 10).

REFERENCES

Alberici, A., Archetti, S., Pilotto, A., Premi, E., Cosseddu, M., Bianchetti, A., Semeraro, F., Salvetti, M., Muiesan, M. L., Padovani, A., et al. (2014). Results from a pilot study on amiodarone administration in monogenic frontotemporal dementia with granulin mutation. Neurological sciences: official journal of the Italian Neurological Society and of the Italian Society of Clinical Neurophysiology 35, 1215-1219.

Arrant, A. E., Filiano, A. J., Unger, D. E., Young, A. H., and Roberson, E. D. (2017). Restoring neuronal progranulin reverses deficits in a mouse model of frontotemporal dementia. Brain: a journal of neurology 140, 1447-1465.

Arrant, A. E., Onyilo, V. C., Unger, D. E., and Roberson, E. D. (2018). Progranulin Gene Therapy Improves Lysosomal Dysfunction and Microglial Pathology Associated with Frontotemporal Dementia and Neuronal Ceroid Lipofuscinosis. The Journal of neuroscience: the official journal of the Society for Neuroscience 38, 2341-2358.

Benussi, L., Binetti, G., and Ghidoni, R. (2017). Loss of Neuroprotective Factors in Neurodegenerative Dementias: The End or the Starting Point?Frontiers in neuroscience 11, 672.

Chen, Y., Li, S., Su, L., Sheng, J., Lv, W., Chen, G., and Xu, Z. (2015). Association of progranulin polymorphism rs5848 with neurodegenerative diseases: a meta-analysis. Journal of neurology 262, 814-822.

Culler, S. J., Hoff, K. G., Voelker, R. B., Berglund, J. A., and Smolke, C. D. (2010). Functional selection and systematic analysis of intronic splicing elements identify active sequence motifs and associated splicing factors. Nucleic acids research 38, 5152-5165.

Evrony, G. D., Lee, E., Mehta, B. K., Benjamini, Y., Johnson, R. M., Cai, X., Yang, L., Haseley, P., Lehmann, H. S., Park, P. J., et al. (2015). Cell lineage analysis in human brain using endogenous retroelements. Neuron 85, 49-59.

Finkel, R. S., Mercuri, E., Darras, B. T., Connolly, A. M., Kuntz, N. L., Kirschner, J., Chiriboga, C. A., Saito, K., Servais, L., Tizzano, E., et al. (2017). Nusinersen versus Sham Control in Infantile-Onset Spinal Muscular Atrophy. The New England journal of medicine 377, 1723-1732.

Grindberg, R. V., Yee-Greenbaum, J. L., McConnell, M. J., Novotny, M., O'Shaughnessy, A. L., Lambert, G. M., Arauzo-Bravo, M. J., Lee, J., Fishman, M., Robbins, G. E., et al. (2013). RNA-sequencing from single nuclei. Proceedings of the National Academy of Sciences of the United States of America 110, 19802-19807.

Hua, Y., Vickers, T. A., Baker, B. F., Bennett, C. F., and Krainer, A. R. (2007). Enhancement of SMN2 exon 7 inclusion by antisense oligonucleotides targeting the exon. PLoS biology 5, e73.

Khvorova, A., and Watts, J. K. (2017). The chemical evolution of oligonucleotide therapies of clinical utility. Nature biotechnology 35, 238-248.

Kordasiewicz, H. B., Stanek, L. M., Wancewicz, E V., Mazur, C., McAlonis, M. M., Pytel, K. A., Artates, J. W., Weiss, A., Cheng, S. H., Shihabuddin, L. S., et al. (2012). Sustained therapeutic reversal of Huntington's disease by transient repression of huntingtin synthesis. Neuron 74, 1031-1044.

Lodato, M. A., Rodin, R. E., Bohrson, C. L., Coulter, M. E., Barton, A. R., Kwon, M., Sherman, M. A., Vitzthum, C. M., Luquette, L. J., Yandava, C. N., et al. (2018). Aging and neurodegeneration are associated with increased mutations in single human neurons. Science 359, 555-559.

Lodato, M. A., Woodworth, M. B., Lee, S., Evrony, G. D., Mehta, B. K., Karger, A., Lee, S., Chittenden, T. W., D'Gama, A. M., Cai, X., et al. (2015). Somatic mutation in single human neurons tracks developmental and transcriptional history. Science 350, 94-98.

Lui, H., Zhang, J., Makinson, S. R., Cahill, M. K., Kelley, K. W., Huang, H. Y., Shang, Y., Oldham, M. C., Martens, L. H., Gao, F., et al. (2016). Progranulin Deficiency Promotes Circuit-Specific Synaptic Pruning by Microglia via Complement Activation. Cell 165, 921-935.

Mercuri, E., Darras, B. T., Chiriboga, C. A., Day, J. W., Campbell, C., Connolly, A. M., Iannaccone, S. T., Kirschner, J., Kuntz, N. L., Saito, K., et al. (2018). Nusinersen versus Sham Control in Later-Onset Spinal Muscular Atrophy. The New England journal of medicine 378, 625-635.

Minami, S. S., Min, S. W., Krabbe, G., Wang, C., Zhou, Y., Asgarov, R., Li, Y., Martens, L. H., Elia, L. P., Ward, M. E., et al. (2014). Progranulin protects against amyloid beta deposition and toxicity in Alzheimer's disease mouse models. Nature medicine 20, 1157-1164.

Sha, S. J., Miller, Z. A., Min, S. W., Zhou, Y., Brown, J., Mitic, L. L., Karydas, A., Koestler, M., Tsai, R., Corbetta-Rastelli, C., et al. (2017). An 8-week, open-label, dose-finding study of nimodipine for the treatment of progranulin insufficiency from GRN gene mutations. Alzheimer's & dementia 3, 507-512.

Rosenberg A. B., Patwardhan R. P., Shendure J., Seelig G. Learning the sequence determinants of alternative splicing from millions of random sequences. Cell. 2015 Oct. 22; 163(3):698-711.

Van Kampen, J. M., Baranowski, D., and Kay, D. G. (2014). Progranulin gene delivery protects dopaminergic neurons in a mouse model of Parkinson's disease. PloS one 9, e97032.

van Roon-Mom, W. M. C., Roos, R. A. C., and de Bot, S. T. (2018). Dose-Dependent Lowering of Mutant Huntingtin Using Antisense Oligonucleotides in Huntington Disease Patients. Nucleic acid therapeutics 28, 59-62.

Wang, Z., Rolish, M. E., Yeo, G., Tung, V., Mawson, M., and Burge, C. B. (2004). Systematic identification and analysis of exonic splicing silencers. Cell 119, 831-845.

Ward, M. E., Chen, R., Huang, H. Y., Ludwig, C., Telpoukhovskaia, M., Taubes, A., Boudin, H., Minami, S. S., Reichert, M., Albrecht, P., et al. (2017). Individuals with progranulin haploinsufficiency exhibit features of neuronal ceroid lipofuscinosis. Science translational medicine 9.

Example 2: Antisense Oligonucleotide-Based Progranulin Augmentation Therapy in Neurodegenerative Diseases Progranulin is a GRN-encoded protein that, when secreted into cerebrospinal fluid, plays a critical neuroprotective function. Recent studies have shown that progranulin augmentation may have therapeutic effects in diverse neurodegenerative diseases including Alzheimer's disease and Parkinson's disease. However, no treatment targeting granulin is available currently.

Remarkable success of nusinersen/Spinraza for spinal muscular atrophy in recent months clearly demonstrated that antisense oligonucleotides (ASOs) can induce sustained gene upregulation in neuronal tissues by modulation of mRNA splicing toward a productive isoform.

The inventor's analysis of RNA-seq coverage of human brain tissue of the HCC1599 cell line at the GRN gene 5' UTR and intron 4 regions, indicated 5' UTR extension and identified unproductive isoforms of GRN. Further, the inventors identified at least two upstream open reading frames in the extended 5' UTR region of GRN.

TABLE 2

Primers and probes used for RT-PCR assay.

| Target | Type | Sequence (5' to 3') |
|---|---|---|
| GRN | Primer | GCCCTGATCCCTGGCCAATG (SEQ ID No. 19) |
| GRN | Primer | TGGGCCATTTGTCCAGAAG (SEQ ID No. 20) |
| GRN | Primer | TCGGACGCAGGTAGCAG (SEQ ID No. 21) |
| GRN | Primer | CACATGGTCTGCCGACAG (SEQ ID No. 22) |
| GRN | Probe | CTGGGTCAAGAATGGTGTGGTCCCTG (SEQ ID No. 23) |
| GRN | Primer | GTCGGACGCAGGCAGA (SEQ ID No. 24) |
| GRN | Primer | TGGGCCATTTGTCCAGAAG (SEQ ID No. 25) |
| GRN | Probe | TTAACAGCAGGGCTGGTGGCTGGAAC (SEQ ID No. 26) |

Figure 14A:
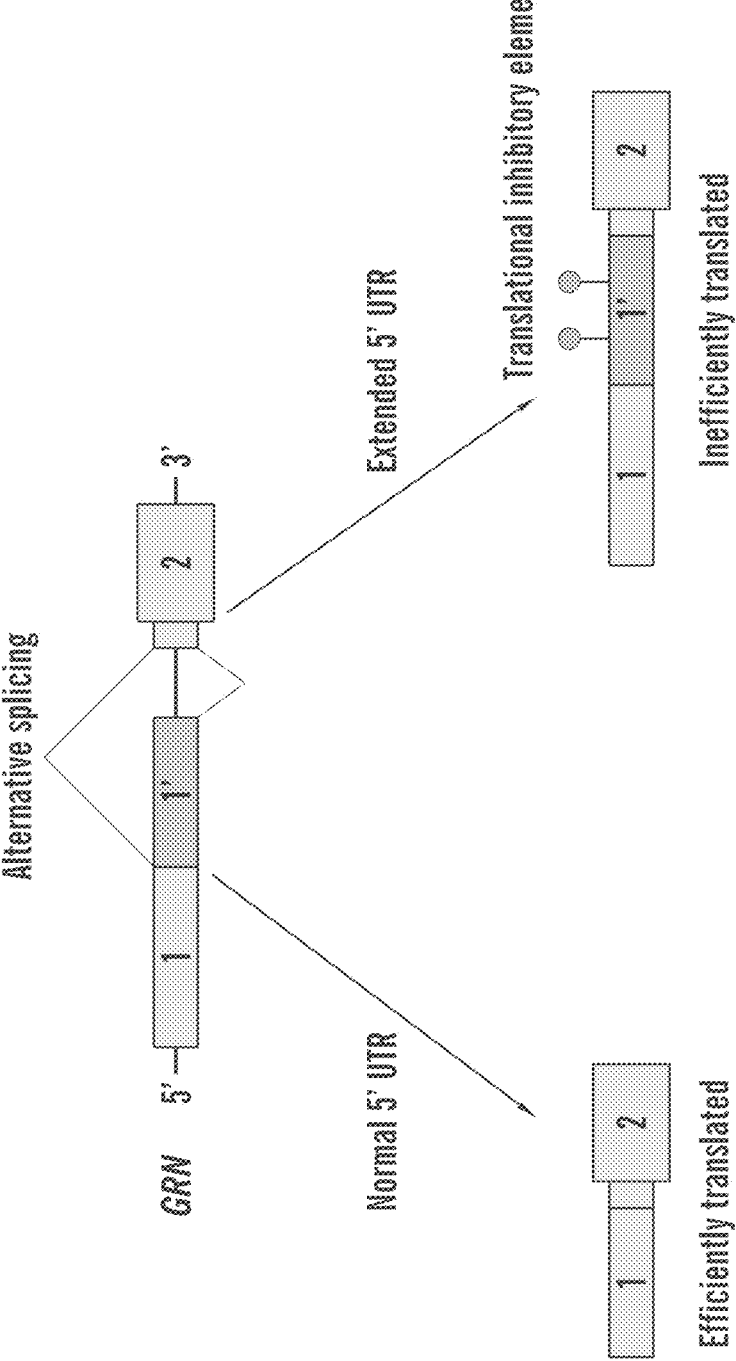
FIG. 14A shows the pattern of alternative splicing at the 5' UTR of GRN without ASO treatment.
Figure 14B:
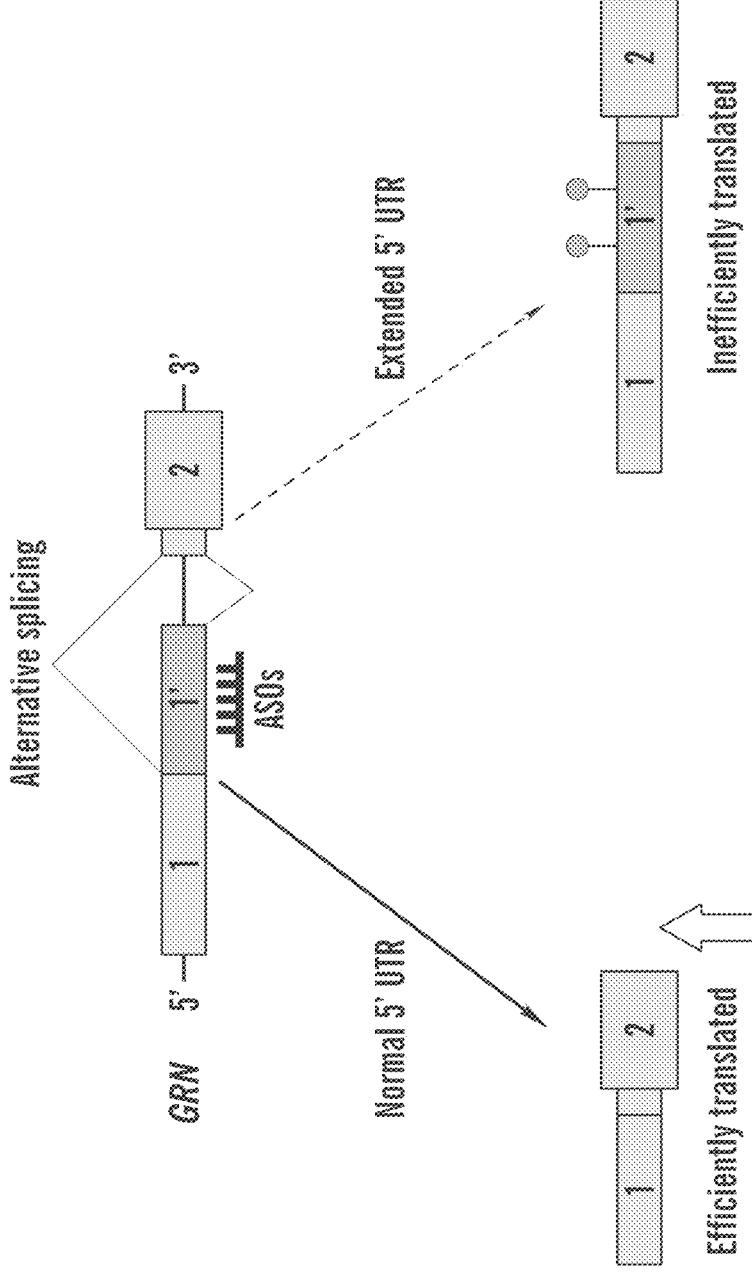
FIG. 14B shows the pattern of alternative splicing at the 5' UTR of GRN with ASO treatment.
Figure 15:
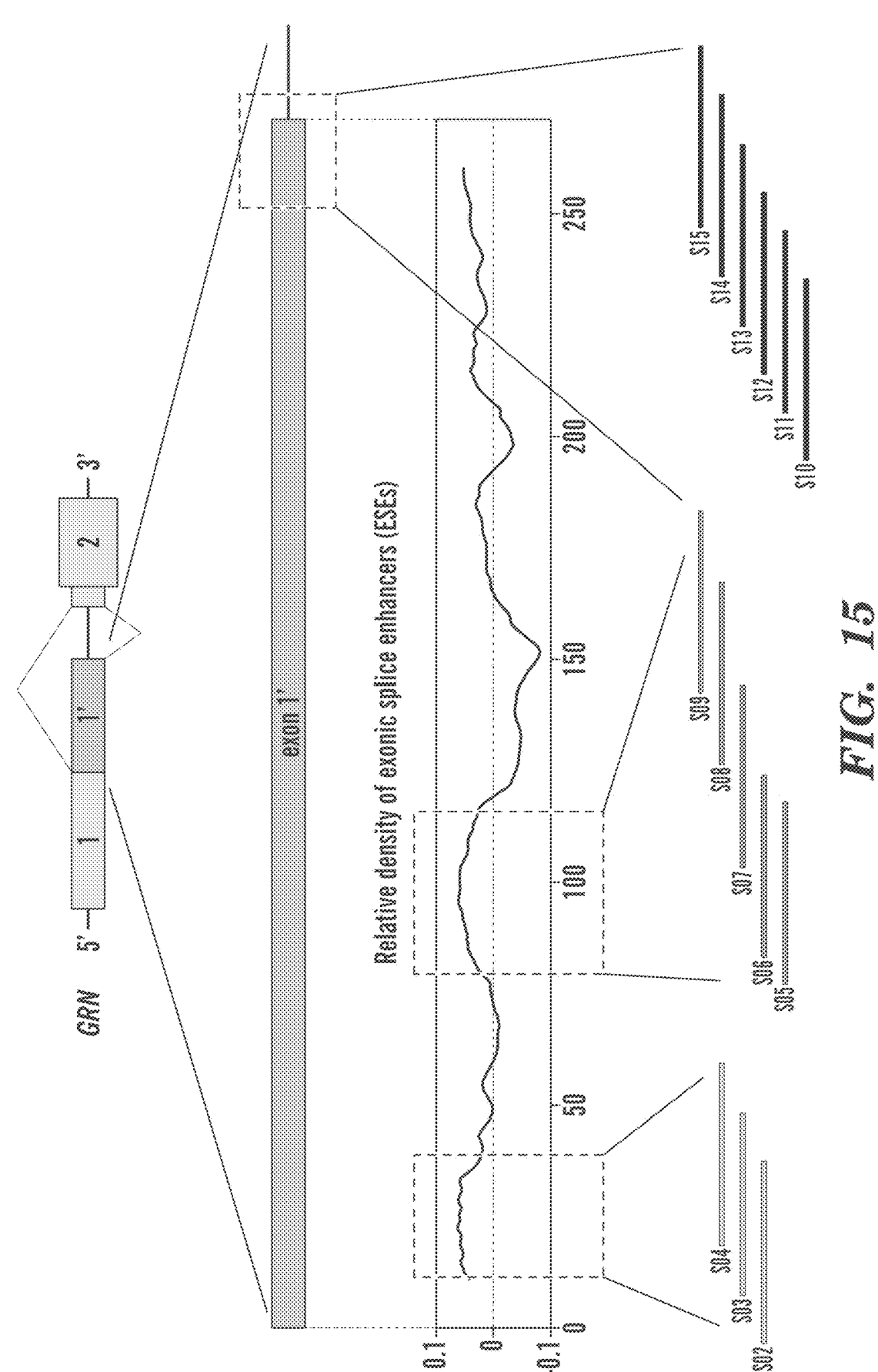
FIG. 15 shows the relative density of exonic splicing enhancers in the extended region of GRN 5' UTR. ASOs were designed to hybridize to the two regions with peak density and the splice donor site specific to the extended region.

FIG. 14A shows the pattern of alternative splicing at the 5' UTR of GRN without ASO treatment. FIG. 14B shows the pattern of alternative splicing at the 5' UTR of GRN with ASO treatment. Treatment with an ASO targeting the 5' UTR region of GRN leads to an efficiently translated GRN, thereby increasing the level of progranulin protein.

The inventors further showed that relative density of exonic splicing enhancers in the extended region of GRN 5' UTR. ASOs were designed to hybridize to the two regions with peak density and the splice donor site specific to the extended region.

Figures 16A, 16B:
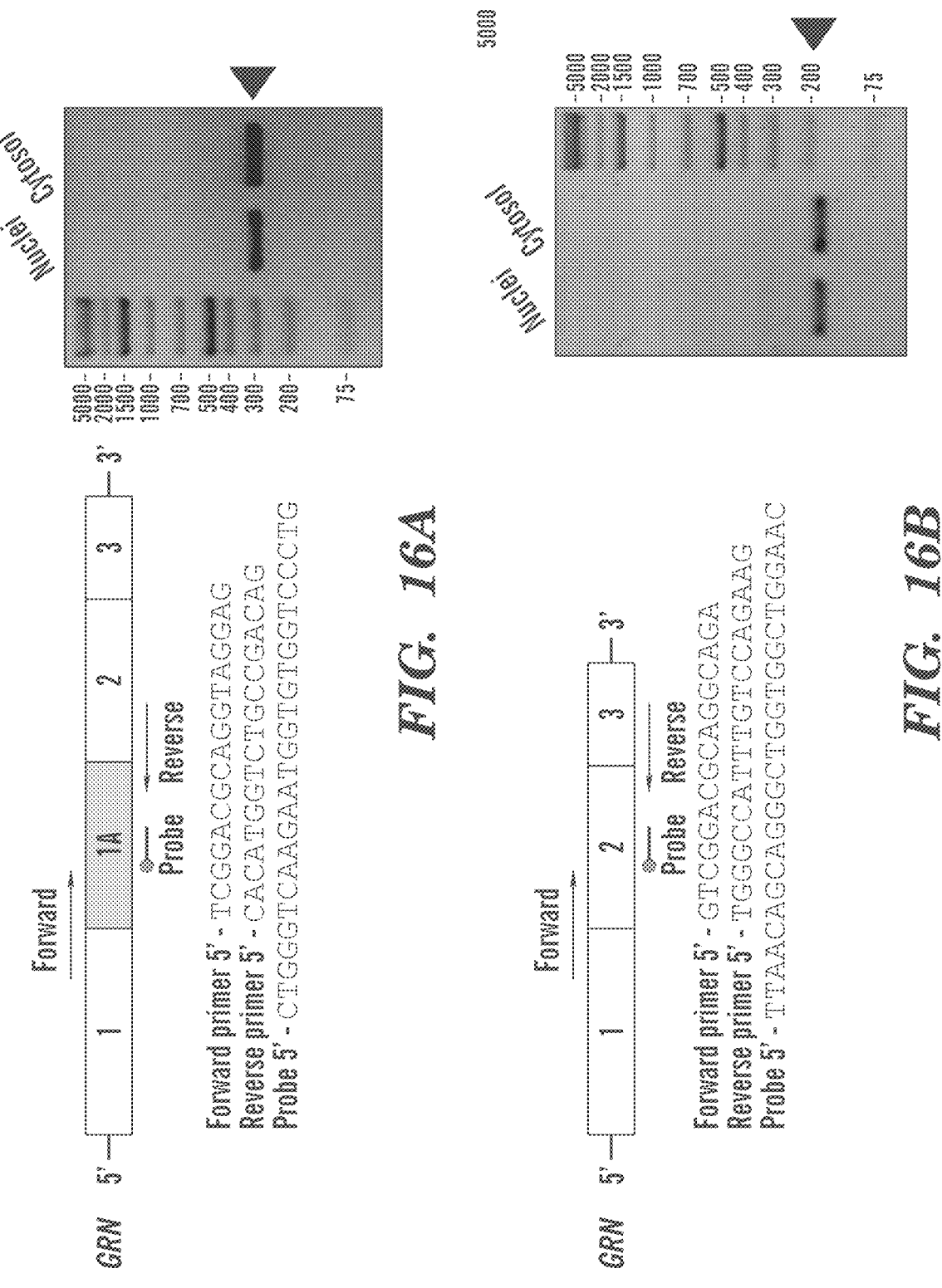
FIG. 16A shows the locations and sequences of the primers (SEQ ID Nos. 21-22) and the probe (SEQ ID No. 23) for qRT-PCR assay for measuring the level of GRN transcript with the extended 5' UTR.
FIG. 16B shows the locations and sequences of the primers (SEQ ID Nos. 24-25) and the probe (SEQ ID No. 26) for qRT-PCR assay for measuring the level of GRN transcript with the normal 5' UTR.
Figure 17:
FIG. 17 shows the levels of GRN transcript with the extended 5' UTR (non-productive isoform) in HCC1599 cells, measured by qPCR, when the cells were treated with different ASOs. For controls, Ctrl, mock-transfection control; SPIN, nusinersen transfection; S01, an irrelevant ASO targeting an intron of IMPDH1 gene. Error bars indicate standard error.
Figure 18:
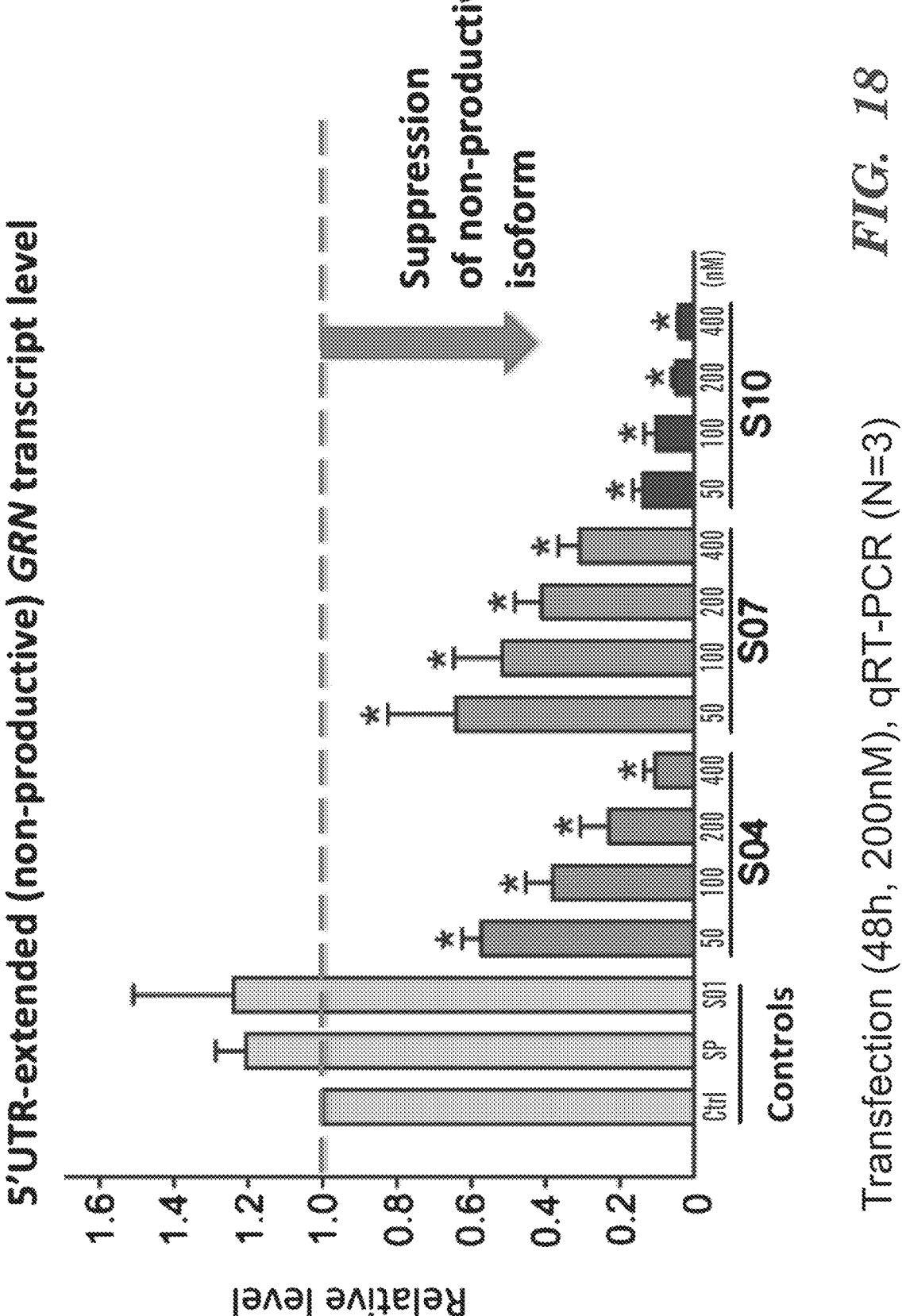
FIG. 18 shows the levels of GRN transcript with the extended 5' UTR (non-productive isoform) in HCC1599 cells, measured by qPCR, when the cells were treated with three lead candidate ASOs (S04, S07, S10) at different doses. For controls, Ctrl, mock-transfection control; SP, nusinersen transfection; S01, an irrelevant ASO targeting an intron of IMPDH1 gene. Error bars indicate standard error.

FIG. 16B shows the locations and sequences of the primers and the probe for qRT-PCR assay for measuring the level of GRNtranscript with the normal 5' UTR.

Figures 7A, 7B:
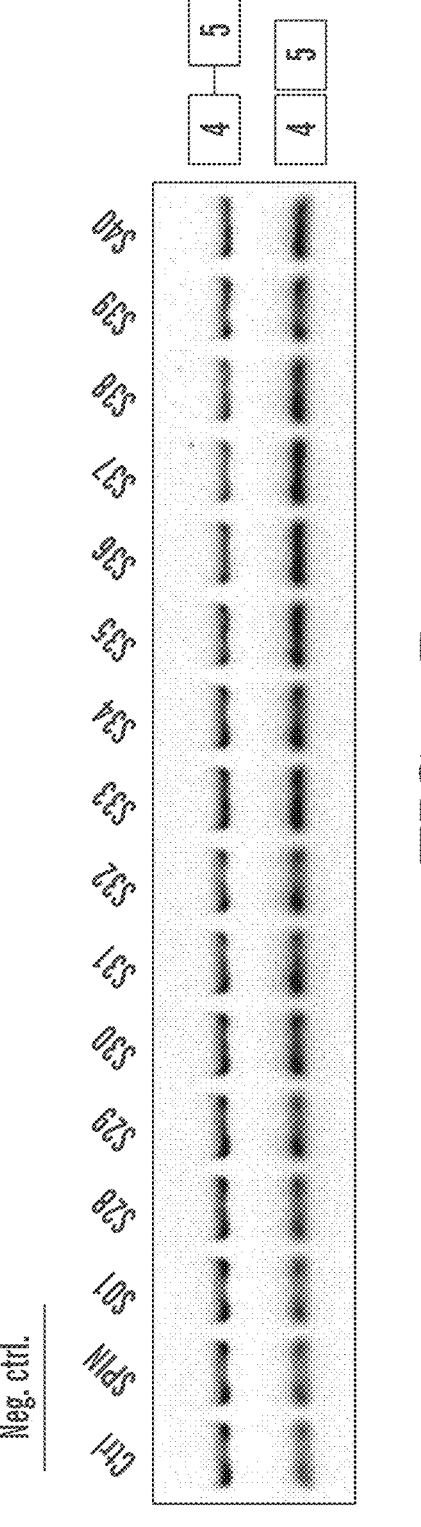
FIGS. 7A-7D demonstrate the efficacy of ASOs assessed by the RT-PCR assay measuring the ratio of the intron 4-spliced vs. unspliced form of GRN.
Figure 7C:
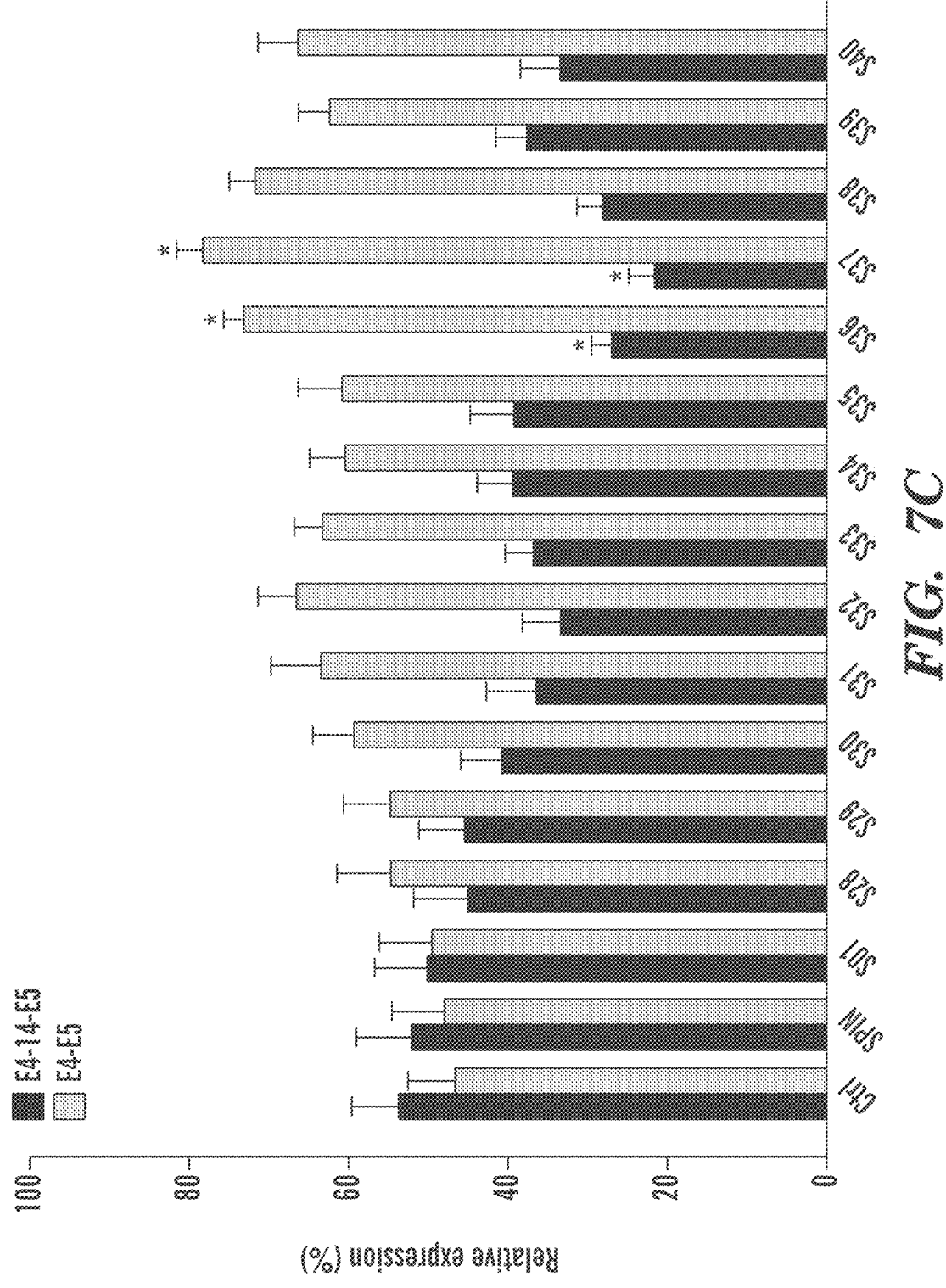
Figure 7D:
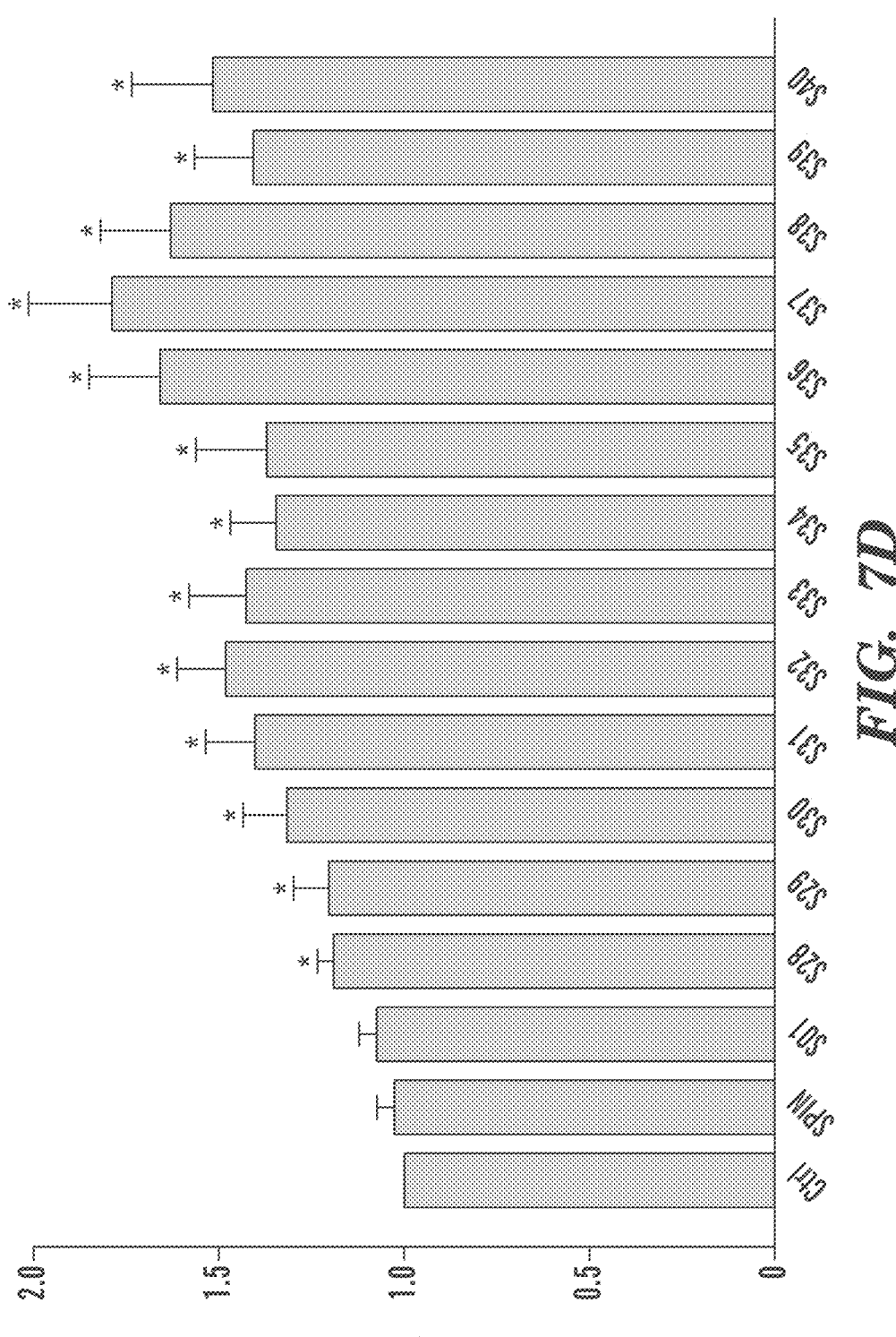
Figure 8A:
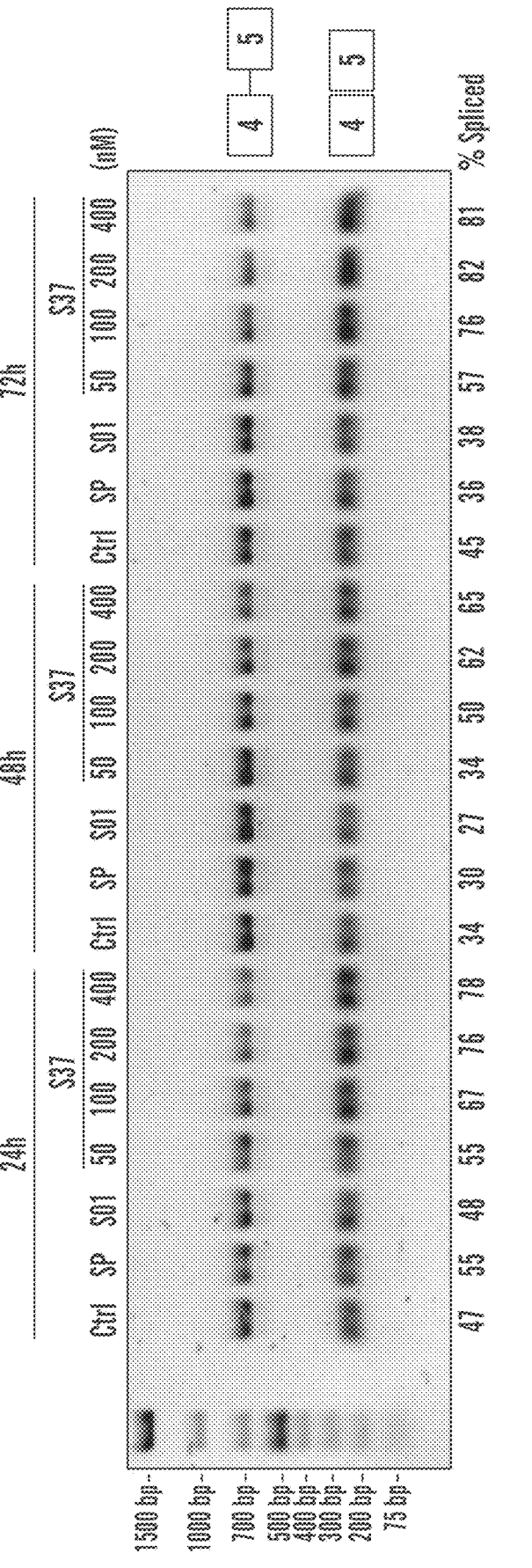
FIGS. 8A-8B demonstrate the dose-dependent efficacy of S37 assessed by the RT-PCR assay measuring the ratio of the intron 4-spliced vs. unspliced form of GRN mRNA.
Figure 8B:
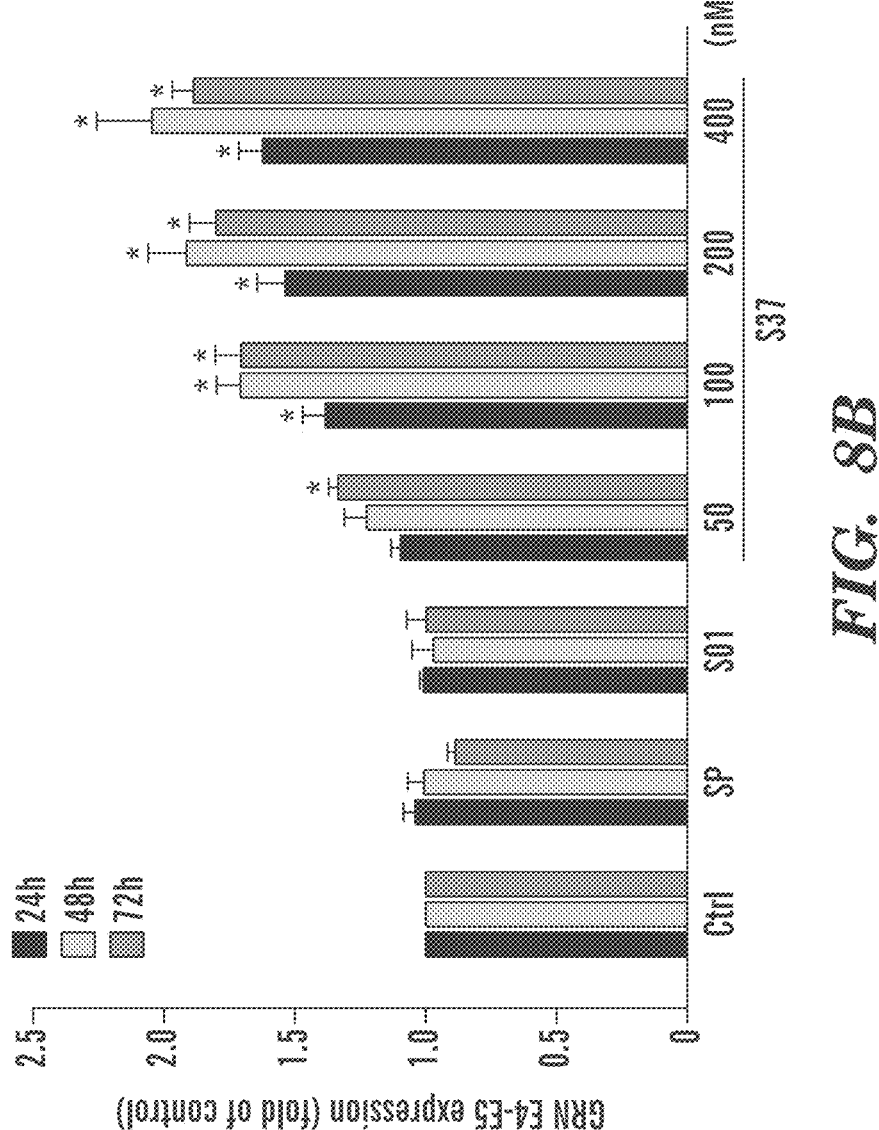
Figure 9A:
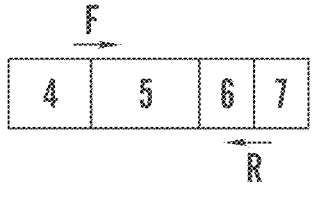
FIGS. 9A-9C demonstrate the dose-dependent efficacy of S37 assessed by the RT-PCR assay measuring the intron 4-spliced form of GRN, normalized to GAPDH level.
Figure 9B:
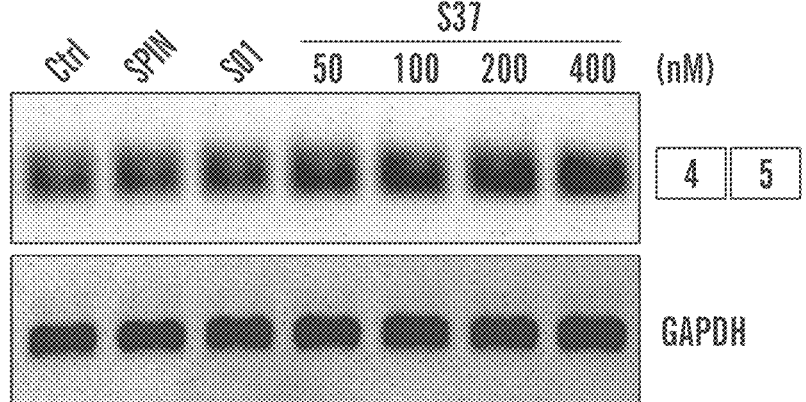
Figure 9C:
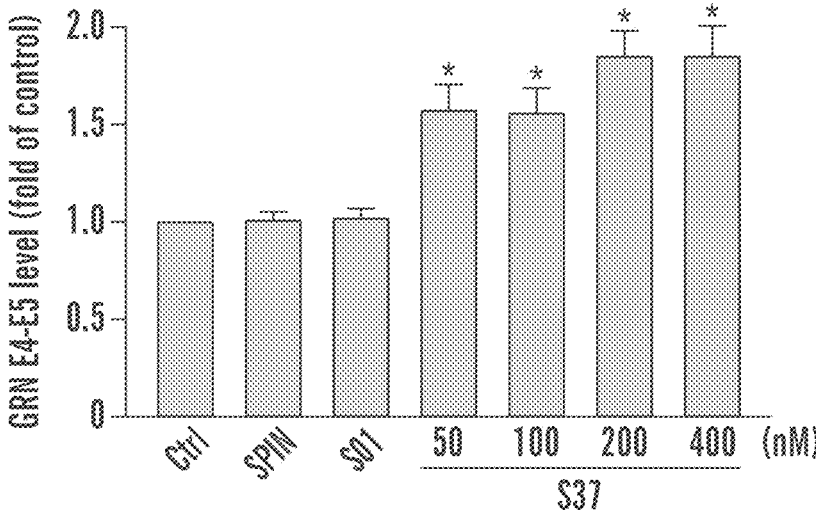
Figure 19A:
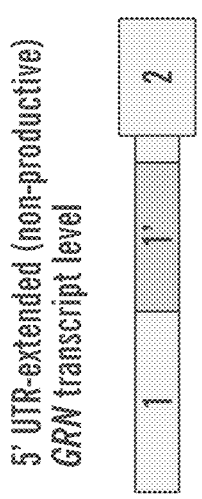
FIG. 19A shows the levels of GRN transcript with the extended 5' UTR (non-productive isoform) in HCC1599 cells, measured by qPCR, when the cells were treated with three lead candidate ASOs (S04, S07, S10) for indicated time periods. For controls, Ctrl, mock-transfection control; SPIN, nusinersen transfection; S01, an irrelevant ASO targeting an intron of IMPDH1 gene. Error bars indicate standard error. N=4.
Figure 19A:
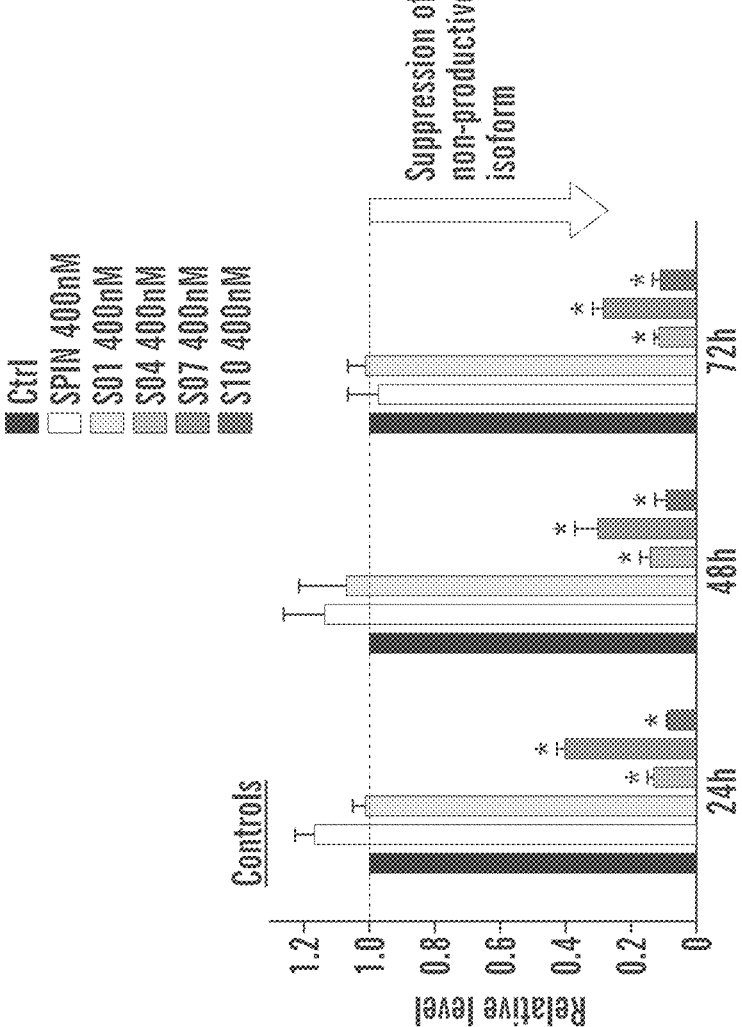
Figure 19B:
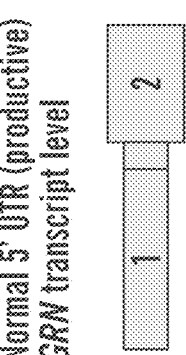
FIG. 19B shows the levels of GRN transcript with the normal 5' UTR (productive isoform) in HCC1599 cells when the cells, measured by qPCR, were treated with three lead candidate ASOs (S04, S07, S10) for indicated time periods. For controls, Ctrl, mock-transfection control; SPIN, nusinersen transfection; S01, an irrelevant ASO targeting an intron of IMPDH1 gene. Error bars indicate standard error. N=4.
Figure 19B:
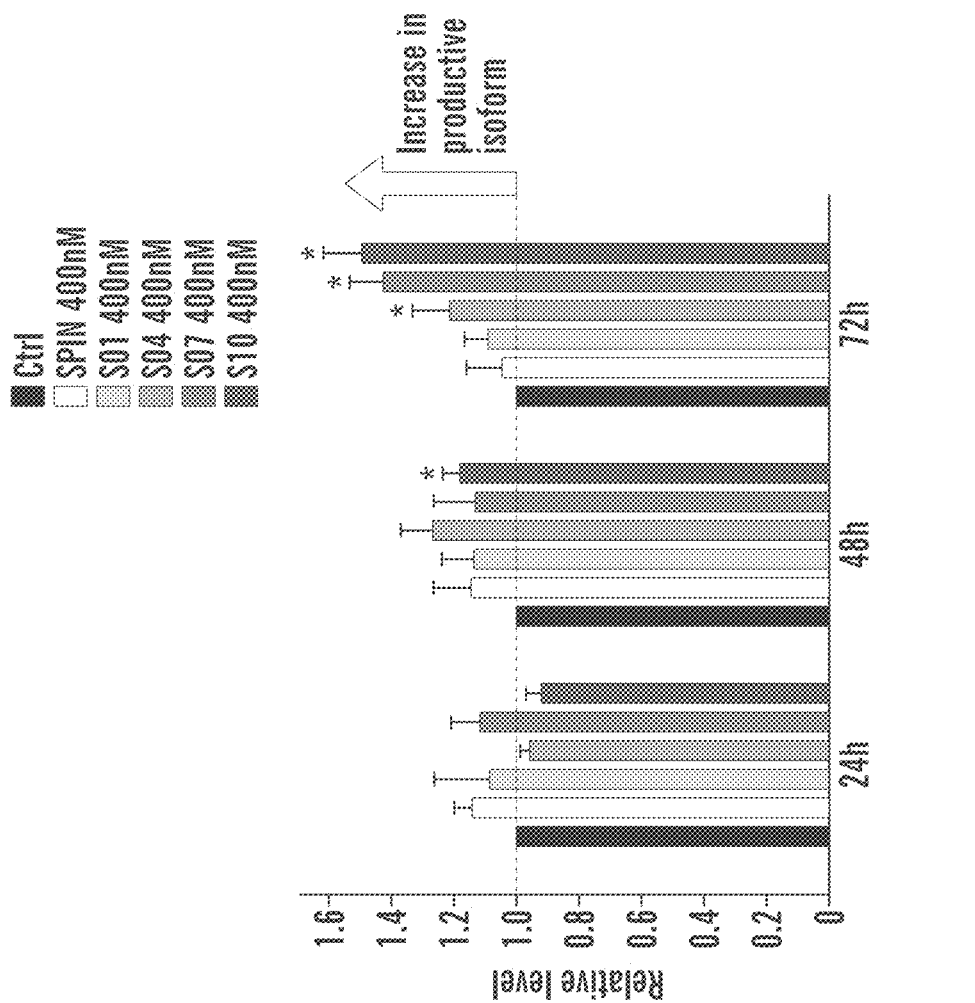

Surprisingly, the inventors found that the levels of GRN transcript with the normal 5' UTR (productive isoform) in HCC1599 cells increased significantly when the cells, measured by qPCR, were treated with three lead candidate ASOs (S04, S07, S10) for indicated time periods (FIG. 19B) while the levels of GRN transcript of the non-productive isoforms were significantly decreased (FIG. 19A). The inventors found that the levels of GRN transcript with the extended 5' UTR (non-productive isoform) were suppressed in HCC1599 cells, measured by qPCR, when the cells were treated with the three lead candidate ASOs (S04, S07, S10) (FIG. 7).

REFERENCES

Alberici, A., Archetti, S., Pilotto, A., Premi, E., Cosseddu, M., Bianchetti, A., Semeraro, F., Salvetti, M., Muiesan, M. L., Padovani, A., et al. (2014). Results from a pilot study on amiodarone administration in monogenic frontotemporal dementia with granulin mutation. Neurological sciences: official journal of the Italian Neurological Society and of the Italian Society of Clinical Neurophysiology 35, 1215-1219.

Arrant, A. E., Filiano, A. J., Unger, D. E., Young, A. H., and Roberson, E. D. (2017). Restoring neuronal progranulin reverses deficits in a mouse model of frontotemporal dementia. Brain: a journal of neurology 140, 1447-1465.

Arrant, A. E., Onyilo, V. C., Unger, D. E., and Roberson, E. D. (2018). Progranulin Gene Therapy Improves Lysosomal Dysfunction and Microglial Pathology Associated with Frontotemporal Dementia and Neuronal Ceroid Lipofuscinosis. The Journal of neuroscience: the official journal of the Society for Neuroscience 38, 2341-2358.

Benussi, L., Binetti, G., and Ghidoni, R. (2017). Loss of Neuroprotective Factors in Neurodegenerative Dementias: The End or the Starting Point?Frontiers in neuroscience 11, 672.

Chen, Y., Li, S., Su, L., Sheng, J., Lv, W., Chen, G., and Xu, Z. (2015). Association of progranulin polymorphism rs5848 with neurodegenerative diseases: a meta-analysis. Journal of neurology 262, 814-822.

Culler, S. J., Hoff, K. G., Voelker, R. B., Berglund, J. A., and Smolke, C. D. (2010). Functional selection and systematic analysis of intronic splicing elements identify active sequence motifs and associated splicing factors. Nucleic acids research 38, 5152-5165.

Evrony, G. D., Lee, E., Mehta, B. K., Benjamini, Y., Johnson, R. M., Cai, X., Yang, L., Haseley, P., Lehmann, H. S., Park, P. J., et al. (2015). Cell lineage analysis in human brain using endogenous retroelements. Neuron 85, 49-59.

Finkel, R. S., Mercuri, E., Darras, B. T., Connolly, A. M., Kuntz, N. L., Kirschner, J., Chiriboga, C. A., Saito, K., Servais, L., Tizzano, E., et al. (2017). Nusinersen versus Sham Control in Infantile-Onset Spinal Muscular Atrophy. The New England journal of medicine 377, 1723-1732.

Grindberg, R. V., Yee-Greenbaum, J. L., McConnell, M. J., Novotny, M., O'Shaughnessy, A. L., Lambert, G. M., Arauzo-Bravo, M. J., Lee, J., Fishman, M., Robbins, G. E., et al. (2013). RNA-sequencing from single nuclei. Proceedings of the National Academy of Sciences of the United States of America 110, 19802-19807.

Hua, Y., Vickers, T. A., Baker, B. F., Bennett, C. F., and Krainer, A. R. (2007). Enhancement of SMN2 exon 7 inclusion by antisense oligonucleotides targeting the exon. PLoS biology 5, e73.

Khvorova, A., and Watts, J. K. (2017). The chemical evolution of oligonucleotide therapies of clinical utility. Nature biotechnology 35, 238-248.

Kordasiewicz, H. B., Stanek, L. M., Wancewicz, E. V., Mazur, C., McAlonis, M. M., Pytel, K. A., Artates, J. W., Weiss, A., Cheng, S. H., Shihabuddin, L. S., et al. (2012). Sustained therapeutic reversal of Huntington's disease by transient repression of huntingtin synthesis. Neuron 74, 1031-1044.

Liang X H, Shen W, Sun H, Migawa M T, Vickers T A, Crooke S T. Translation efficiency of mRNAs is increased by antisense oligonucleotides targeting upstream open reading frames. Nat Biotechnol. 2016 August; 34(8):875-80.

Lodato, M. A., Rodin, R. E., Bohrson, C. L., Coulter, M. E., Barton, A. R., Kwon, M., Sherman, M. A., Vitzthum, C. M., Luquette, L. J., Yandava, C. N., et al. (2018). Aging and neurodegeneration are associated with increased mutations in single human neurons. Science 359, 555-559.

Lodato, M. A., Woodworth, M. B., Lee, S., Evrony, G. D., Mehta, B. K., Karger, A., Lee, S., Chittenden, T. W., D'Gama, A. M., Cai, X., et al. (2015). Somatic mutation in single human neurons tracks developmental and transcriptional history. Science 350, 94-98.

Lui, H., Zhang, J., Makinson, S. R., Cahill, M. K., Kelley, K. W., Huang, H. Y., Shang, Y., Oldham, M. C., Martens, L. H., Gao, F., et al. (2016). Progranulin Deficiency Promotes Circuit-Specific Synaptic Pruning by Microglia via Complement Activation. Cell 165, 921-935.

Mercuri, E., Darras, B. T., Chiriboga, C. A., Day, J. W., Campbell, C., Connolly, A. M., Iannaccone, S T., Kirschner, J., Kuntz, N. L., Saito, K., et al. (2018). Nusinersen versus Sham Control in Later-Onset Spinal Muscular Atrophy. The New England journal of medicine 378, 625-635.

Minami, S. S., Min, S. W., Krabbe, G., Wang, C., Zhou, Y., Asgarov, R., Li, Y., Martens, L. H., Elia, L. P., Ward, M. E., et al. (2014). Progranulin protects against amyloid beta deposition and toxicity in Alzheimer's disease mouse models. Nature medicine 20, 1157-1164.

Sha, S. J., Miller, Z. A., Min, S. W., Zhou, Y., Brown, J., Mitic, L. L., Karydas, A., Koestler, M., Tsai, R., Corbetta-Rastelli, C., et al. (2017). An 8-week, open-label, dose-finding study of nimodipine for the treatment of progranulin insufficiency from GRN gene mutations. Alzheimer's & dementia 3, 507-512.

Rosenberg A. B., Patwardhan R. P., Shendure J., Seelig G. Learning the sequence determinants of alternative splicing from millions of random sequences. Cell. 2015 Oct. 22; 163(3):698-711.

Van Kampen, J. M., Baranowski, D., and Kay, D. G. (2014). Progranulin gene delivery protects dopaminergic neurons in a mouse model of Parkinson's disease. PloS one 9, e97032.

van Roon-Mom, W. M. C., Roos, R. A. C., and de Bot, S. T. (2018). Dose-Dependent Lowering of Mutant Huntingtin Using Antisense Oligonucleotides in Huntington Disease Patients. Nucleic acid therapeutics 28, 59-62.

Wang, Z., Rolish, M. E., Yeo, G., Tung, V., Mawson, M., and Burge, C. B. (2004). Systematic identification and analysis of exonic splicing silencers. Cell 119, 831-845.

Ward, M. E., Chen, R., Huang, H. Y., Ludwig, C., Telpoukhovskaia, M., Taubes, A., Boudin, H., Minami, S. S., Reichert, M., Albrecht, P., et al. (2017). Individuals with progranulin haploinsufficiency exhibit features of neuronal ceroid lipofuscinosis. Science translational medicine.

Example 3: Antisense Oligonucleotide-Based Progranulin Augmentation Therapy in Neurodegenerative Diseases Summary: Progranulin is a GRN-encoded protein that plays critical lysosomal and anti-neuroinflammatory functions. A therapy that boosts GRN expression would address the root genetic cause (GRN haploinsufficiency) of GRN-subtype frontotemporal dementia, a fatal and orphan neurodegenerative disease that affects over 6,000 patients in the US alone. The therapy would also be effective for other neurodegenerative diseases including Alzheimer's and Parkinson's diseases. However, no such therapy is available currently. The inventors have developed three ASOs that can increase the progranulin protein level in a human neuroblastoma cell line by multiple folds. Here, the inventors assessed the in vivo drug properties of our ASOs: target engagement, tolerability, pharmacokinetics, and biodistribution. Since the inventor's ASOs target primate-specific sequence and mechanisms, we plan to conduct non-human primate experiments.

Target: Progranulin is a GRN-encoded protein that is involved in three of five hallmarks of neurodegenerationl: regulation of proteostasis, lysosomal function, and neuroinflammation. Multiple studies have shown that progranulin augmentation may have therapeutic effects in diverse neurodegenerative diseases including frontotemporal dementia (FTD) (2,3), Alzheimer's disease (4,5,6), and Parkinson's disease (4,7), which in aggregate affect tens of millions of people worldwide. Advantages of progranulin as a drug target include:

Reversibility of Phenotype

A recent study showed that AAV-mediated restoration of GRN expression in GRN+/– mice can reverse a disease-associated behavioral phenotype (social dominance deficit), which suggests that progranulin augmentation therapy can have therapeutic benefit even after symptom onset.

Cross-Correction

Because Progranulin is a CSF-circulating protein, even if the drug does not get into disease-inflicted cells, it can have therapeutic effects on them by boosting CSF-circulating progranulin level through other cells in the CNS that take up the drug.

Pharmacodynamics Marker

Because progranulin is a CSF-circulating protein and CSF sample can be readily collected at every intrathecal injection, pre-dose CSF progranulin level can be used to monitor drug level and adjust dosage in the clinical setting. This is particularly important in light of a previous study, suggesting that overshooting progranulin level might be toxic (8).

Progranulin augmentation therapy can address the root genetic cause (loss-of-function of one copy of GRN, and the resulting haploinsufficiency) of GRN-subtype FTD (GRN-FTD), a highly aggressive (expected fatality within ~7 years after diagnosis) and orphan (no treatment option) neurodegenerative disease that affects more than 6,000 patients in the US alone.

As no FDA-approved progranulin augmentation therapy is available currently, the unmet need is obvious. The inventors anticipate no issues with the FDA approval or the market adoption by patients, clinicians, and payors of an effective and safe such therapy. Potentially competing programs include:

Historically, progranulin-boosting small molecules performed poorly in clinical trials (9,10). It is possibly because small molecules (1) often show poor brain biodistribution, (2) have non-gene-specific mechanisms, such as ion channel modulation and epigenetic modulation, or (3) have unpredictable toxicity profiles. A phase I clinical trial is currently ongoing with a sortilin (progranulin receptor) antibody that inflates CSF-circulating progranulin level by blocking the cellular entry of progranulin. However, this antibody might have limited efficacy as it is not capable of restoring, and may rather exacerbate, intracellular progranulin deficiency.

Gene Therapy

AAV-mediated restoration of GRN rescues the phenotype of GRN+/− and GRN−/− mice without apparent toxicity (11, 12). However, Chen-Plotkin and colleagues reported a conflicting results that AAV-mediated GRN restoration caused substantial T cell-mediated toxicity in both GRN−/− and wild type mice (8). These mixed results suggest that the safety of ectopic, constitutive, and irreversible overexpression of GRN by AAV need to be investigated further.

Antisense oligonucleotide (ASO) Breakthroughs in chemistry and neuronal delivery method of oligonucleotides have enabled the massive clinical impact of nusinersen/Spinraza, an ASO drug that boosts the expression of SMN2 in spinal muscular atrophy (13-15). Non-human primate studies and clinical trials of ASO drugs for Huntington's disease have also shown promising results (16, 17). Recently, the inventors have developed a fully patient-customized ASO drug for a young girl with CLN7 Batten disease, an ultra-rare, orphan, and fatal neurodegenerative condition (18). In one of the fastest drug development campaigns in the history of medicine, we gave the first patient dose under one year from the initial patient contact. Treatment with the drug for the last two years has resulted in substantial reductions in seizure frequency and duration. This work has demonstrated that ASO is a platform for rapid, genetically targeted, rational drug development for neurological conditions.

Our progranulin-boosting ASOs. The inventors have developed three ASOs that can enhance output from the wild type copy of human GRN. As GRN-FTD patients retain one wild type copy of GRN, the ASOs can augment the copy, compensating for the loss of the inactivated copy. The inventors have shown that the treatment of ASOs in multiple human cell lines including a neuroblastoma cell line can induce substantial upregulation of progranulin protein level. As a single intrathecal dose of ASOs can last several months (in vivo half-life of ~150 days), we envision that this therapy could be given in every 2-4 months in an out-patient setting, carefully adjusting the drug dose based on the CSF-circulating progranulin level to avoid potential overshooting toxicity.

Rational ASO Design Strategy

Figure 20A:
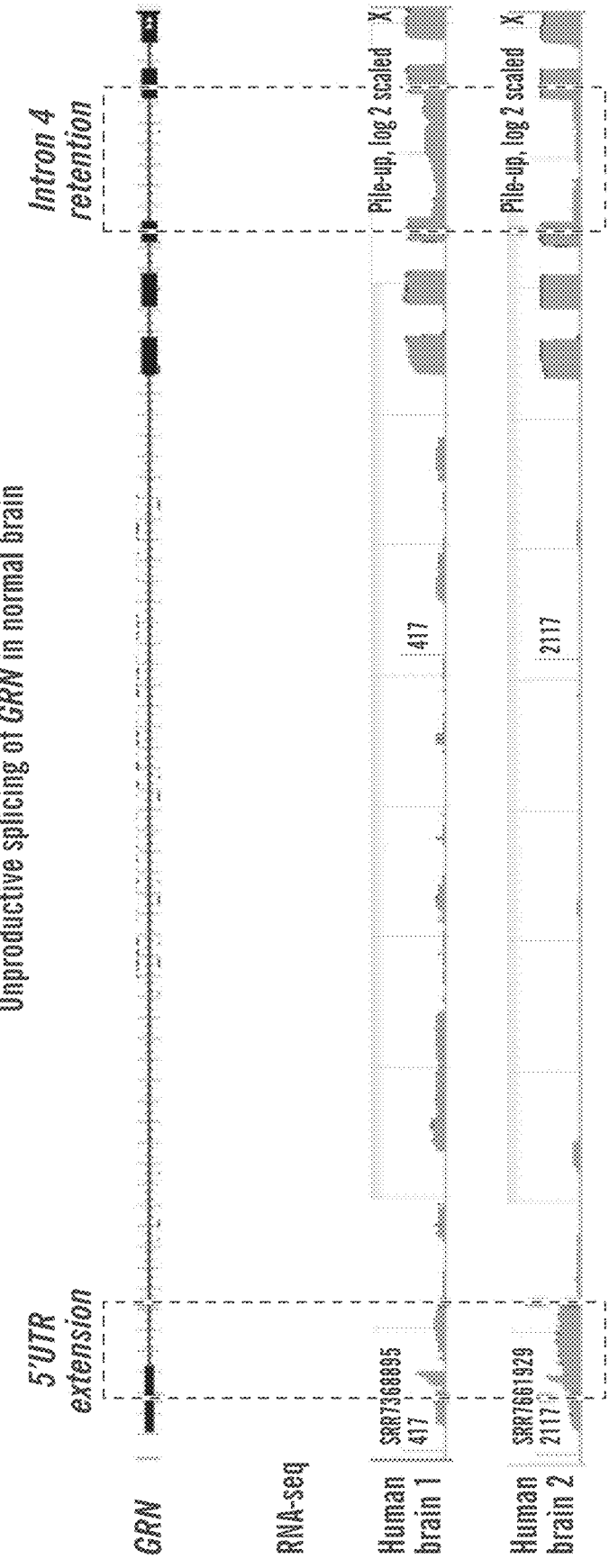
FIG. 20A shows the splicing pattern of wild type GRN in normal human brain tissues.

Analysis of public RNA-seq datasets identified unproductive splice isoforms of GRN in normal human brain tissues (FIG. 20A). These isoforms include: (1) an isoform with an extended segment of 5'UTR and (2) an isoform with the retention of intron 4. These isoforms give rise to poor progranulin expression because of inefficient translation (5'UTR extension) and premature translational termination (intron 4 retention). ASOs that redirect these unproductive isoforms into a productive isoform through splice modulation can lead to increases in progranulin levels in the brain. Based on our computational prediction of splice regulatory elements, we designed 27 ASOs that are predicted to modulate GRN splicing toward a productive isoform.

Figure 20B:
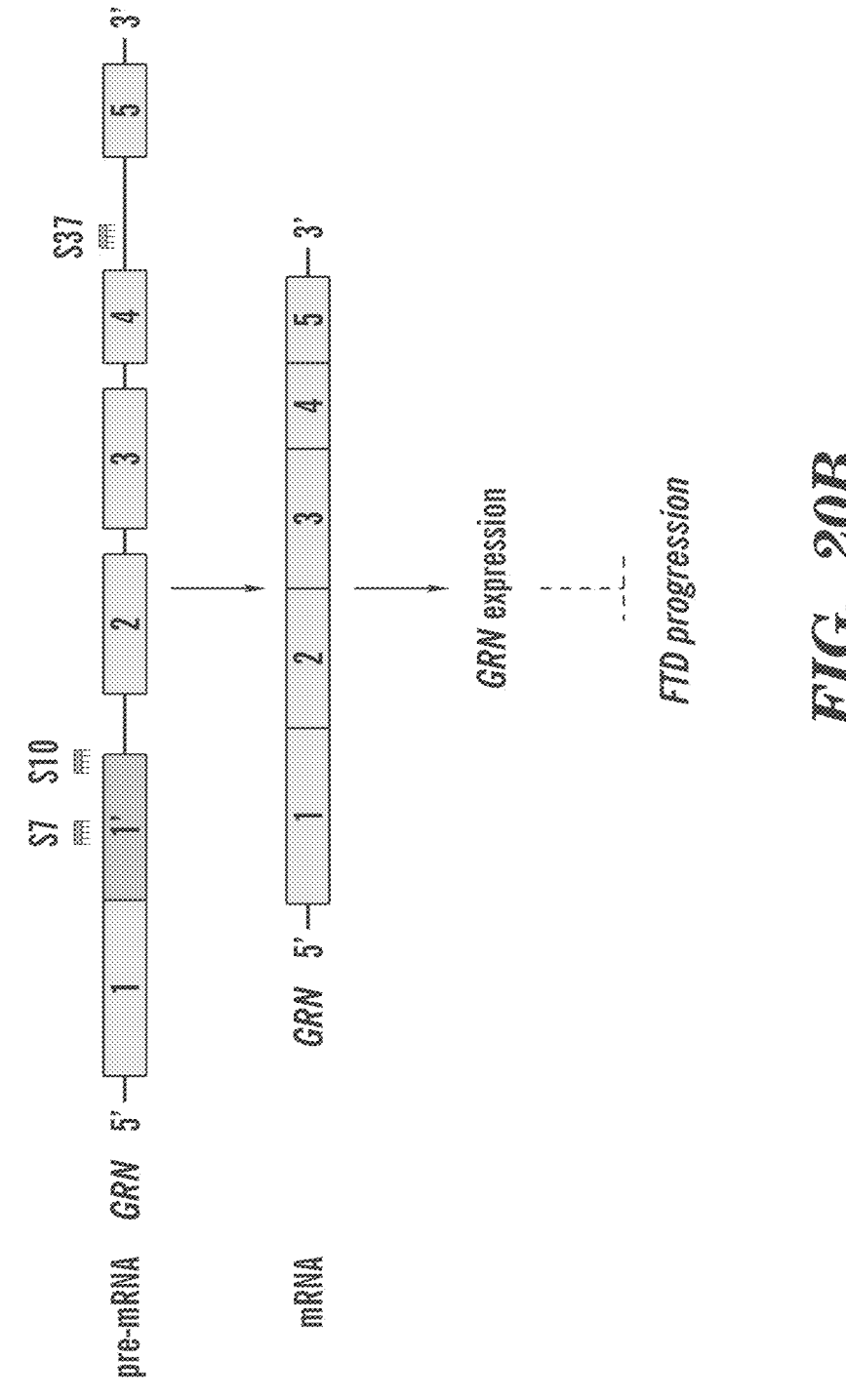
FIG. 20B shows the lead ASOs (S7, S10, S37) and their binding sites and mechanisms of action.
Figure 20C:
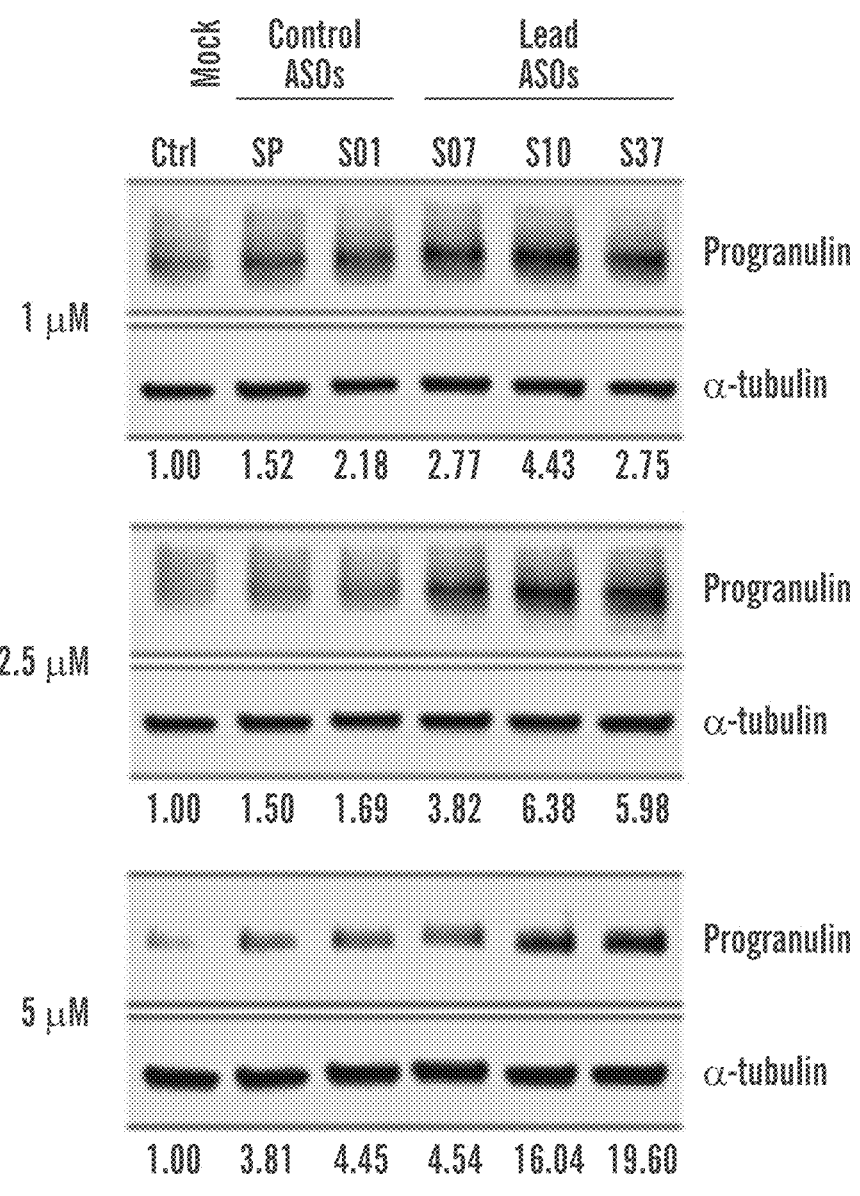
FIG. 20C shows the intracellular progranulin protein level (by Western blot with cell lysate) of a neuroblastoma cell line (BE(2)-M17) after 6 days of gymnotic transfection (natural uptake). Numbers at the bottom of the blots show progranulin levels, normalized by loading controls (α-tubulin). SP, Spinraza/nusinersen; S01, nontargeting oligonucleotide.
Figure 20D:
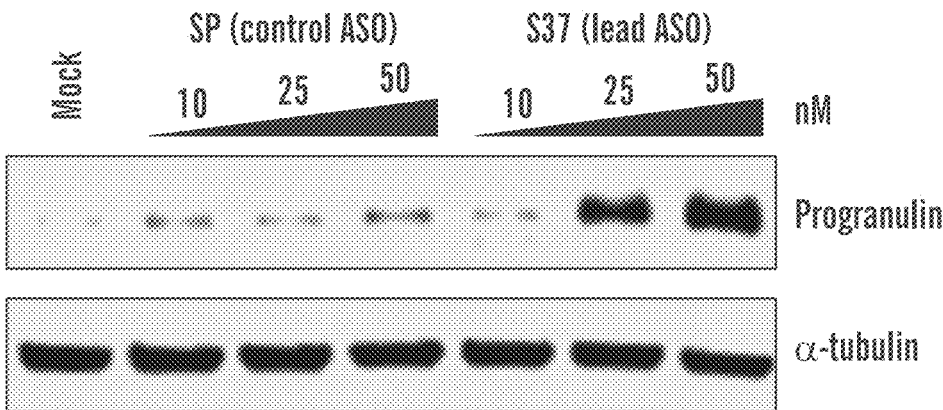
FIG. 20D shows the intracellular progranulin protein level of BE(2)-M17 48 hours after lipid-based transfection.
Figure 20E:
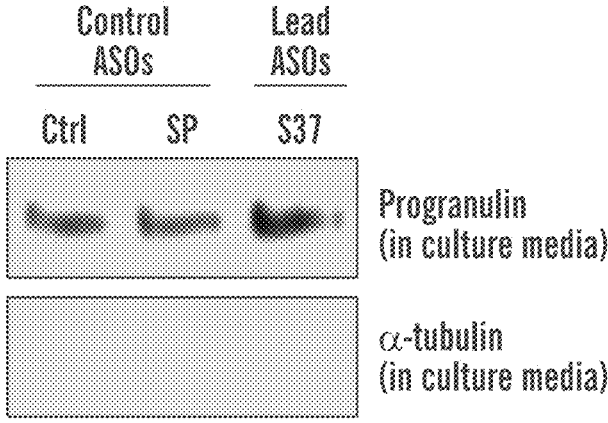
FIG. 20E shows the extracellular progranulin protein level (by Western blot with acetone precipitated culture media) of BE(2)-M17 24 hours after lipid-based transfection. The absence of α-tubulin is expected as it is not a secreted protein.
Figure 21:
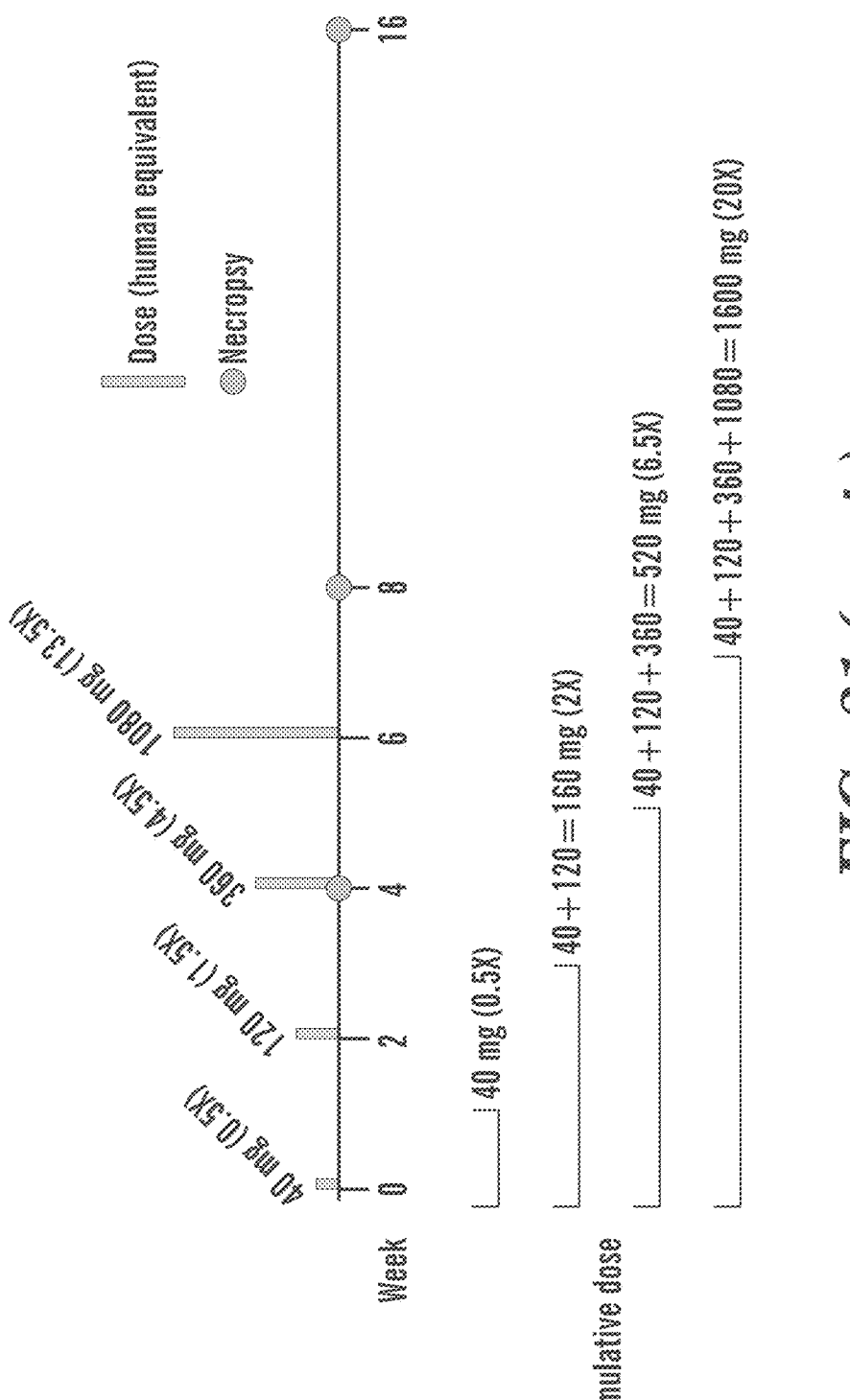
FIG. 21 shows the tested groups and doses for the three lead ASOs (S7, S10, S37).

ASO screening and validation Analysis of the CCLE RNA-seq dataset of 933 cell lines identified HCC1599, a human breast cancer cell line that has a normal human brain-like GRN splicing pattern. We developed RT-PCR-based assays that can specifically measure the levels of productive vs. unproductive splice isoforms of GRN mRNA for both the 5'UTR extension and intron 4 retention. The RT-PCR-based screening of the ASOs identified three lead ASOs (S07, S10, targeting 5'UTR extension; S37, targeting intron 4 retention; FIG. 20B) that significantly promotes the productive isoform levels. Upon treatment of our lead ASOs, reproducible increases in intracellular progranulin levels were observed in HCC1599. The increases were confirmed in BE(2)-M17, a neuroblastoma cell line by both gymnosis (natural uptake, FIG. 20C) and lipid-based transfection (FIG. 20D), where the degree of increase was as high as 20-fold. Secreted progranulin levels were also found to be elevated (FIG. 20E). No signs of toxicity in survival and proliferation of the ASO-treated cells were observed. Sequence alignments of the ASOs to the human genome showed negligible potential for off-target interactions.

Animals Non-naïve cynomolgus monkeys, single sex (14 animals; 12+2 (extra) animals)

Regulatory compliance Non-GLP

Injection Intrathecal (1-2 mL, needle injection, under anesthesia)

Dose formulation Artificial CSF solution

Dose level 0.5× to 20× of a proposed human dose (80 mg)

In-life monitoring Viability (twice daily), detailed clinical observations (weekly), body weights (weekly), clinical pathology (pretest, before necropsy), functional observation battery (pretest, after dose, before necropsy), blood draw for toxicokinetics (pretest, 3 time points after dose)

Tissue collection CSF prior to each injection, tissue (plasma, CSF, full standard and CNS tissue panel) for bioanalysis and histopathology. full pathology reading

REFERENCES

1. Wyss-Coray, T. Ageing, neurodegeneration and brain rejuvenation. *Nature* 539, 180-186 (2016).
2. Kao, A. W., McKay, A., Singh, P. P., Brunet, A. & Huang, E. J. Progranulin, lysosomal regulation and neurodegenerative disease. *Nat. Rev. Neurosci.* 18, 325-333 (2017).
3. Wilke, C. et al. Cerebrospinal Fluid Progranulin, but Not Serum Progranulin, Is Reduced in Frontotemporal Dementia. *Neurodegener. Dis.* 17, 83-88 (2017).
4. Chen, Y. et al. Association of progranulin polymorphism rs5848 with neurodegenerative diseases: a meta-analysis. *J. Neurol.* 262, 814-822 (2015).
5. Lui, H. et al. Progranulin Deficiency Promotes Circuit-Specific Synaptic Pruning by Microglia via Complement Activation. *Cell* 165, 921-935 (2016).

6. Minami, S. S. et al. Progranulin protects against amyloid
   R deposition and toxicity in Alzheimer's disease mouse
   models. *Nat. Med.* 20, 1157-1164 (2014).
7. Van Kampen, J. M., Baranowski, D. & Kay, D. G.
   Progranulin Gene Delivery Protects Dopaminergic Neu-
   rons in a Mouse Model of Parkinson's Disease. *PLoS One*
   9, e97032 (2014).
8. Amado, D. A. et al. AAV-Mediated Progranulin Delivery
   to a Mouse Model of Progranulin Deficiency Causes T
   Cell-Mediated Toxicity. *Mol. Ther.* 27, 465-478 (2019).
9. Alberici, A. et al. Results from a pilot study on amio-
   darone administration in monogenic frontotemporal
   dementia with granulin mutation. *Neurol. Sci.* 35, 1215-
   1219 (2014).
10. Sha, S. J. et al. An 8-week, open-label, dose-finding
    study of nimodipine for the treatment of progranulin
    insufficiency from GRN gene mutations. *Alzheimer's
    Dement. Transl. Res. Clin. Interv.* 3, 507-512 (2017).
11. Arrant, A. E., Onyilo, V. C., Unger, D. E. & Roberson,
    E. D. Progranulin Gene Therapy Improves Lysosomal
    Dysfunction and Microglial Pathology Associated with
    Frontotemporal Dementia and Neuronal Ceroid Lipofus-
    cinosis. *J. Neurosci.* 38, 2341-2358 (2018).

12. Arrant, A. E., Filiano, A. J., Unger, D. E., Young, A. H.
    & Roberson, E. D. Restoring neuronal progranulin
    reverses deficits in a mouse model of frontotemporal
    dementia. *Brain* 140, 1447-1465 (2017).
13. Finkel, R. S. et al. Treatment of infantile-onset spinal
    muscular atrophy with nusinersen: a phase 2, open-label,
    dose-escalation study. *Lancet* 388, 3017-3026 (2016).
14. Finkel, R. S. et al. Nusinersen versus Sham Control in
    Infantile-Onset Spinal Muscular Atrophy. *N. Engl. J.
    Med.* 377, 1723-1732 (2017).
15. Mercuri, E. et al. Nusinersen versus Sham Control in
    Later-Onset Spinal Muscular Atrophy. *N. Engl. J. Med.*
    378, 625-635 (2018).
16. Kordasiewicz, H. B. et al. Sustained Therapeutic Rever-
    sal of Huntington's Disease by Transient Repression of
    Huntingtin Synthesis. *Neuron* 74, 1031-1044 (2012).
17. van Roon-Mom, W. M. C., Roos, R. A. C. & de Bot, S.
    T. Dose-Dependent Lowering of Mutant Huntingtin
    Using Antisense Oligonucleotides in Huntington Disease
    Patients. *Nucleic Acid Ther.* 28, 59-62 (2018).
18. Kim, J. et al. Patient-Customized Oligonucleotide
    Therapy for a Rare Genetic Disease. 1-9 (2019).

What is claimed:

1. An antisense oligonucleotide (ASO) comprising an oligonucleotide of 20 or more linked nucleotides or modified nucleotides in length, wherein the oligonucleotide comprises a nucleobase sequence targeting a Progranulin (GRN) mRNA to increase GRN expression or activity, wherein the oligonucleotide has at least 80% sequence identity to the nucleotide sequence of SEQ ID NO: 12.

2. The ASO of claim 1, wherein the oligonucleotide comprises at least one modified nucleotide.

3. The ASO of claim 1, wherein the ASO:
(a) the nucleobase sequence has homology to a 5' untranslated region (5' UTR) of GRN;
(b) increases GRN expression or activity in the central nervous system;
(c) increases GRN expression or activity in the brain;
(d) modulates the splicing of a pre-mRNA target;
(e) modulates GRN expression in the brain by modulating splicing of a pre-mRNA target;
(f) targets an intron-exon or exon-intron junction of the pre-mRNA target;
(g) targets a splicing enhancer or silencer element in the pre-mRNA target;
(h) increases progranulin expression or activity in the brain by regulating translation efficiency of the pre-mRNA target;
(i) increases progranulin expression or activity in the brain by regulating nuclear export of the pre-mRNA target;
(j) increases progranulin expression or activity in the brain by regulating stability of the pre-mRNA target; or
(k) can be used to treat a disease or disorder selected from Alzheimer's disease, Frontotemporal Dementia, Batten disease, and Parkinson's disease.

4. The ASO of claim 1, wherein the ASO comprises:
(a) at least one modified nucleotide which comprises a modified sugar moiety;
(b) a 2' modification of its sugar moiety;
(c) a 2'-O-methyl, 2'-methoxyethoxy, 2'-O-methoxyethyl, 2'-dimethylaminooxyethoxy, 2'-dimethylaminoethoxyethoxy, 2'-fluoro, or 2'-acetamide modification on every sugar moiety;
(d) a locked nucleic acid (LNA) nucleobase; or
(e) at least one modified linkage.

5. The ASO of claim 1, wherein the linkage of the ASO comprises a phosphodiester, phosphotriester, or phosphorothioate backbone linkage.

6. The ASO of claim 1, wherein the ASO is a morpholino or peptide nucleic acid.

7. The ASO of claim 1, wherein the ASO comprises at least one modified base which increases binding affinity for the pre-mRNA target, which increases nuclease resistance of the antisense compound, or which decreases immune-stimulation.

8. The ASO of claim 7, wherein the modified base is methyl-C.

9. The ASO of claim 1, wherein the ASO is a mixture of one or more stereopure molecules with a defined sequence.

10. A composition comprising an ASO of claim 1 and a pharmaceutically acceptable carrier.

11. A method of increasing the level of progranulin mRNA in a cell comprising contacting the cell with an ASO of claim 1, such that the level of progranulin mRNA in the cell is increased.

* * * * *